US012611266B2

(12) United States Patent
Draper et al.

(10) Patent No.: US 12,611,266 B2
(45) Date of Patent: Apr. 28, 2026

(54) PATENT INTRODUCER FOR A ROBOTIC SYSTEM

(71) Applicant: Auris Health, Inc., Santa Clara, CA (US)

(72) Inventors: Jeffrey William Draper, San Francisco, CA (US); Ryan Jeffrey Connolly, San Carlos, CA (US); Douglas Bruce Dull, San Jose, CA (US); Marcus Andrew Foley, San Jose, CA (US); Richard August Leparmentier, San Carlos, CA (US)

(73) Assignee: Auris Health, Inc., Santa Clara, CA (US)

( * ) Notice: Subject to any disclaimer, the term of this patent is extended or adjusted under 35 U.S.C. 154(b) by 959 days.

(21) Appl. No.: 16/913,686

(22) Filed: Jun. 26, 2020

(65) Prior Publication Data

US 2020/0405411 A1    Dec. 31, 2020

Related U.S. Application Data

(60) Provisional application No. 62/868,796, filed on Jun. 28, 2019.

(51) Int. Cl.
A61B 1/267        (2006.01)
A61B 1/00        (2006.01)
        (Continued)

(52) U.S. Cl.
CPC .......... A61B 34/30 (2016.02); A61B 1/00149 (2013.01); A61B 1/00154 (2013.01);
        (Continued)

(58) Field of Classification Search
CPC ......... A61B 34/30; A61B 34/37; A61B 50/13; A61B 1/00149; A61B 1/00154;
        (Continued)

(56) References Cited

U.S. PATENT DOCUMENTS 2,556,601 A    6/1951 Schofield
2,566,183 A    8/1951 Forss
        (Continued)

FOREIGN PATENT DOCUMENTS

CN        101161426        4/2008
CN        101443069        5/2009
        (Continued)

OTHER PUBLICATIONS

EP Search Report for U.S. Appl. No. 20/831,853, dated Jun. 2, 2023, 9 pages.
        (Continued)

*Primary Examiner* — Michael J Carey
*Assistant Examiner* — William B Chou
(74) *Attorney, Agent, or Firm* — Paradice & Li LLP

(57)        ABSTRACT

Systems and methods relating to medical technology are disclosed. For example, a medical robotic system can include first and second robotic arms. An introducer can be coupled to the first robotic arm. The introducer can include a first opening, a second opening, and a channel connecting the first opening and the second opening. A flexible elongate medical tool can be coupled to the second robotic arm. The second robotic arm can be configured to drive the flexible elongate medical tool through the introducer coupled to the first robotic arm and into a patient.

37 Claims, 24 Drawing Sheets

(51) Int. Cl.

| | |
|---|---|
| *A61B 34/30* | (2016.01) |
| *A61B 50/13* | (2016.01) |
| *A61B 17/00* | (2006.01) |
| *A61B 34/37* | (2016.01) |
| *A61M 25/01* | (2006.01) |

(52) U.S. Cl.
CPC ............ *A61B 1/2676* (2013.01); *A61B 50/13* (2016.02); *A61B 2017/00477* (2013.01); *A61B 2034/301* (2016.02); *A61B 34/37* (2016.02); *A61M 25/0113* (2013.01)

(58) Field of Classification Search
CPC ............ A61B 1/2676; A61B 2034/301; A61B 2017/00477; A61M 25/0013
See application file for complete search history.

(56) References Cited

U.S. PATENT DOCUMENTS

| | | | |
|---|---|---|---|
| 2,623,175 A | 12/1952 | Finke | |
| 2,730,699 A | 1/1956 | Gratian | |
| 2,884,808 A | 5/1959 | Mueller | |
| 3,294,183 A | 12/1966 | Riley et al. | |
| 3,472,083 A | 10/1969 | Schnepel | |
| 3,513,724 A | 5/1970 | Box | |
| 3,595,074 A | 7/1971 | Johnson | |
| 3,734,207 A | 5/1973 | Fishbein | |
| 3,739,923 A | 6/1973 | Totsuka | |
| 3,763,860 A | 10/1973 | Clarke | |
| 3,784,031 A | 1/1974 | Nitu | |
| 3,790,002 A | 2/1974 | Guilbaud et al. | |
| 3,921,536 A | 11/1975 | Savage | |
| 3,926,386 A | 12/1975 | Stahmann | |
| 4,040,413 A | 8/1977 | Ohshiro | |
| 4,141,245 A | 2/1979 | Brandstetter | |
| 4,198,960 A | 4/1980 | Utsugi | |
| 4,241,884 A | 12/1980 | Lynch | |
| 4,243,034 A | 1/1981 | Brandt | |
| 4,351,493 A | 9/1982 | Sonnek | |
| 4,357,843 A | 11/1982 | Peck et al. | |
| 4,384,493 A | 5/1983 | Grunbaum | |
| 4,470,407 A | 9/1984 | Hussein | |
| 4,507,026 A | 3/1985 | Lund | |
| 4,530,471 A | 7/1985 | Inoue | |
| 4,532,935 A | 8/1985 | Wang et al. | |
| 4,555,960 A | 12/1985 | King | |
| 4,685,458 A | 8/1987 | Leckrone | |
| 4,688,555 A | 8/1987 | Wardle | |
| 4,745,908 A | 5/1988 | Wardle | |
| 4,747,405 A | 5/1988 | Leckrone | |
| 4,784,150 A | 11/1988 | Voorhies et al. | |
| 4,854,301 A | 8/1989 | Nakajima | |
| 4,857,058 A | 8/1989 | Payton | |
| 4,898,574 A | 2/1990 | Uchiyama et al. | |
| 4,907,168 A | 3/1990 | Boggs | |
| 4,945,790 A | 8/1990 | Golden | |
| 4,983,165 A | 1/1991 | Loiterman | |
| 5,029,574 A | 7/1991 | Shimamura et al. | |
| 5,085,659 A | 2/1992 | Rydell | |
| 5,150,452 A | 9/1992 | Pollack et al. | |
| 5,196,023 A | 3/1993 | Martin | |
| 5,207,128 A | 5/1993 | Albright | |
| 5,217,465 A | 6/1993 | Steppe | |
| 5,234,428 A | 8/1993 | Kaufman | |
| 5,256,150 A | 10/1993 | Quiachon et al. | |
| 5,277,085 A | 1/1994 | Tanimura et al. | |
| 5,308,323 A | 5/1994 | Sogawa et al. | |
| 5,318,589 A | 6/1994 | Lichtman | |
| 5,325,848 A | 7/1994 | Adams et al. | |
| 5,342,381 A | 8/1994 | Tidemand | |
| 5,344,395 A | 9/1994 | Whalen et al. | |
| 5,350,101 A | 9/1994 | Godlewski | |
| 5,353,783 A | 10/1994 | Nakao et al. | |
| 5,370,609 A | 12/1994 | Drasler et al. | |
| 5,372,124 A | 12/1994 | Takayama et al. | |
| 5,411,016 A | 5/1995 | Kume | |
| 5,426,687 A | 6/1995 | Goodall et al. | |
| 5,431,649 A | 7/1995 | Mulier et al. | |
| 5,441,485 A | 8/1995 | Peters | |
| 5,449,356 A | 9/1995 | Walbrink | |
| 5,450,843 A | 9/1995 | Moll et al. | |
| 5,472,426 A | 12/1995 | Bonati et al. | |
| 5,496,267 A | 3/1996 | Drasler | |
| 5,501,667 A | 3/1996 | Verduin, Jr. | |
| 5,507,725 A | 4/1996 | Savage et al. | |
| 5,520,684 A | 5/1996 | Imran | |
| 5,524,180 A | 6/1996 | Wang et al. | |
| 5,545,170 A | 8/1996 | Hart | |
| 5,559,294 A | 9/1996 | Hoium et al. | |
| 5,562,239 A | 10/1996 | Boiarski et al. | |
| 5,562,648 A | 10/1996 | Peterson | |
| 5,562,678 A | 10/1996 | Booker | |
| 5,572,999 A | 11/1996 | Funda et al. | |
| 5,573,535 A | 11/1996 | Viklund | |
| 5,613,973 A | 3/1997 | Jackson et al. | |
| 5,645,083 A | 7/1997 | Essig et al. | |
| 5,653,374 A | 8/1997 | Young et al. | |
| 5,658,311 A | 8/1997 | Baden | |
| 5,695,500 A | 12/1997 | Taylor et al. | |
| 5,697,949 A | 12/1997 | Giurtino et al. | |
| 5,709,661 A | 1/1998 | Van Egmond | |
| 5,710,870 A | 1/1998 | Ohm | |
| 5,716,325 A | 2/1998 | Bonutti | |
| 5,737,500 A | 4/1998 | Seraji et al. | |
| 5,767,840 A | 6/1998 | Selker | |
| 5,779,623 A | 7/1998 | Bonnell | |
| 5,788,667 A | 8/1998 | Stoller | |
| 5,792,135 A | 8/1998 | Madhani et al. | |
| 5,792,165 A | 8/1998 | Klieman | |
| 5,797,900 A | 8/1998 | Madhani | |
| 5,798,627 A | 8/1998 | Gilliland | |
| 5,810,770 A | 9/1998 | Chin et al. | |
| 5,842,390 A | 12/1998 | Bouligny | |
| 5,855,583 A | 1/1999 | Wang et al. | |
| 5,893,869 A | 4/1999 | Barnhart | |
| 5,897,491 A | 4/1999 | Kastenbauer et al. | |
| 5,921,968 A | 7/1999 | Lampropoulos et al. | |
| 5,924,175 A | 7/1999 | Lippitt | |
| 5,943,056 A | 8/1999 | Sato | |
| 5,967,934 A | 10/1999 | Ishida et al. | |
| 5,989,230 A | 11/1999 | Frassica | |
| 6,071,281 A | 6/2000 | Burnside et al. | |
| 6,077,219 A | 6/2000 | Viebach | |
| 6,084,371 A | 7/2000 | Kress et al. | |
| 6,093,157 A | 7/2000 | Chandrasekaran | |
| 6,110,171 A | 8/2000 | Rydell | |
| 6,120,476 A | 9/2000 | Fung et al. | |
| 6,120,498 A | 9/2000 | Jani et al. | |
| 6,154,000 A | 11/2000 | Rastegar et al. | |
| 6,156,030 A | 12/2000 | Neev | |
| 6,171,234 B1 | 1/2001 | White et al. | |
| 6,174,318 B1 | 1/2001 | Bates et al. | |
| 6,183,435 B1 | 2/2001 | Bumbalough et al. | |
| 6,185,478 B1 | 2/2001 | Koakutsu et al. | |
| 6,206,903 B1 | 3/2001 | Ramans | |
| 6,236,906 B1 | 5/2001 | Muller | |
| 6,272,371 B1 | 8/2001 | Shlomo | |
| 6,289,579 B1 | 9/2001 | Viza et al. | |
| 6,322,557 B1 | 11/2001 | Nikolaevich | |
| 6,375,635 B1 | 4/2002 | Moutafis | |
| 6,394,998 B1 | 5/2002 | Wallace et al. | |
| 6,401,572 B1 | 6/2002 | Provost | |
| 6,405,078 B1 | 6/2002 | Moaddeb et al. | |
| 6,436,107 B1 | 8/2002 | Wang et al. | |
| 6,440,061 B1 | 8/2002 | Wenner et al. | |
| 6,487,940 B2 | 12/2002 | Hart et al. | |
| 6,491,701 B2 | 12/2002 | Tierney et al. | |
| 6,508,823 B1 | 1/2003 | Gonon | |
| 6,522,906 B1 | 2/2003 | Salisbury et al. | |
| 6,577,891 B1 | 6/2003 | Jaross et al. | |
| 6,676,668 B2 | 1/2004 | Mercereau et al. | |
| 6,685,698 B2 | 2/2004 | Morley et al. | |
| 6,695,818 B2 | 2/2004 | Wollschlager | |

(56)                References Cited

U.S. PATENT DOCUMENTS

| | | | |
|---|---|---|---|
| 6,706,050 B1 | 3/2004 | Giannadakis | |
| 6,726,675 B1 | 4/2004 | Beyar | |
| 6,786,896 B1 | 9/2004 | Madhani et al. | |
| 6,827,712 B2 | 12/2004 | Tovey et al. | |
| 7,044,936 B2 | 5/2006 | Harding | |
| 7,172,580 B2 | 2/2007 | Hruska et al. | |
| 7,248,944 B2 | 7/2007 | Green | |
| 7,276,044 B2 | 10/2007 | Ferry et al. | |
| 7,282,055 B2 | 10/2007 | Tsuruta | |
| 7,559,934 B2 | 7/2009 | Teague et al. | |
| 7,615,042 B2 | 11/2009 | Beyar et al. | |
| 7,635,342 B2 | 12/2009 | Ferry et al. | |
| 7,736,356 B2 | 6/2010 | Cooper et al. | |
| 7,766,856 B2 | 8/2010 | Ferry et al. | |
| 7,882,841 B2 | 2/2011 | Aljuri | |
| 7,938,809 B2 | 5/2011 | Lampropoulos et al. | |
| 7,963,911 B2 | 6/2011 | Turliuc | |
| 7,972,298 B2 | 7/2011 | Wallace et al. | |
| 7,974,674 B2 | 7/2011 | Hauck et al. | |
| 7,987,046 B1 | 7/2011 | Peterman | |
| 7,998,020 B2 | 8/2011 | Kidd et al. | |
| 8,002,713 B2 | 8/2011 | Heske | |
| 8,004,229 B2 | 8/2011 | Nowlin et al. | |
| 8,038,598 B2 | 10/2011 | Khachi | |
| 8,052,636 B2 | 11/2011 | Moll et al. | |
| 8,092,397 B2 | 1/2012 | Wallace et al. | |
| 8,157,308 B2 | 4/2012 | Pedersen | |
| 8,182,415 B2 | 5/2012 | Larkin et al. | |
| 8,187,173 B2 | 5/2012 | Miyoshi | |
| 8,257,303 B2 | 9/2012 | Moll et al. | |
| 8,277,417 B2 | 10/2012 | Fedinec et al. | |
| 8,291,791 B2 | 10/2012 | Light et al. | |
| 8,414,505 B1 | 4/2013 | Weitzner | |
| 8,425,465 B2 | 4/2013 | Nagano | |
| 8,480,595 B2 | 7/2013 | Speeg | |
| 8,523,762 B2 | 9/2013 | Miyamoto et al. | |
| 8,540,748 B2 | 9/2013 | Murphy et al. | |
| 8,541,970 B2 | 9/2013 | Nowlin | |
| 8,671,817 B1 | 3/2014 | Bogusky | |
| 8,720,448 B2 | 5/2014 | Reis et al. | |
| 8,746,252 B2 | 6/2014 | McGrogan et al. | |
| 8,749,190 B2 | 6/2014 | Nowlin et al. | |
| 8,786,241 B2 | 7/2014 | Nowlin et al. | |
| 8,820,603 B2 | 9/2014 | Shelton et al. | |
| 8,821,480 B2 | 9/2014 | Burbank | |
| 8,870,815 B2 | 10/2014 | Bhat et al. | |
| 8,882,660 B2 | 11/2014 | Phee et al. | |
| 8,945,163 B2 | 2/2015 | Voegele et al. | |
| 8,956,280 B2 | 2/2015 | Eversull et al. | |
| 8,961,533 B2 | 2/2015 | Stahler et al. | |
| 8,968,333 B2 | 3/2015 | Yu et al. | |
| 8,992,542 B2 | 3/2015 | Hagag et al. | |
| 9,173,713 B2 | 11/2015 | Hart et al. | |
| 9,179,979 B2 | 11/2015 | Jinno | |
| 9,204,933 B2 | 12/2015 | Reis et al. | |
| 9,259,280 B2 | 2/2016 | Au | |
| 9,259,281 B2 | 2/2016 | Griffiths et al. | |
| 9,259,282 B2 | 2/2016 | Azizian | |
| 9,296,104 B2 | 3/2016 | Swarup et al. | |
| 9,307,969 B2 * | 4/2016 | Novak | A61B 34/20 |
| 9,326,822 B2 | 5/2016 | Lewis et al. | |
| 9,345,456 B2 | 5/2016 | Tsonton et al. | |
| 9,345,544 B2 | 5/2016 | Hourtash et al. | |
| 9,375,284 B2 | 6/2016 | Hourtash | |
| 9,408,669 B2 | 8/2016 | Kokish et al. | |
| 9,415,510 B2 | 8/2016 | Hourtash et al. | |
| 9,446,177 B2 | 9/2016 | Millman et al. | |
| 9,452,018 B2 | 9/2016 | Yu | |
| 9,457,168 B2 | 10/2016 | Moll et al. | |
| 9,460,536 B2 | 10/2016 | Hasegawa et al. | |
| 9,480,534 B2 | 11/2016 | Bowling | |
| 9,498,601 B2 | 11/2016 | Tanner et al. | |
| 9,504,604 B2 | 11/2016 | Alvarez | |
| 9,510,911 B2 | 12/2016 | Hourtash | |
| 9,517,106 B2 | 12/2016 | Hourtash et al. | |
| 9,561,083 B2 | 2/2017 | Yu et al. | |
| 9,566,125 B2 | 2/2017 | Bowling | |
| 9,592,042 B2 | 3/2017 | Titus | |
| 9,597,152 B2 | 3/2017 | Schaeffer | |
| 9,622,827 B2 | 4/2017 | Yu et al. | |
| 9,636,184 B2 | 5/2017 | Lee et al. | |
| 9,636,483 B2 | 5/2017 | Hart et al. | |
| 9,668,814 B2 | 6/2017 | Kokish | |
| 9,675,422 B2 | 6/2017 | Hourtash et al. | |
| 9,687,310 B2 | 6/2017 | Nowlin et al. | |
| 9,713,509 B2 | 7/2017 | Schuh et al. | |
| 9,727,963 B2 | 8/2017 | Mintz et al. | |
| 9,730,757 B2 | 8/2017 | Brudniok | |
| 9,737,371 B2 | 8/2017 | Romo et al. | |
| 9,737,373 B2 | 8/2017 | Schuh | |
| 9,744,335 B2 | 8/2017 | Jiang | |
| 9,757,187 B2 * | 9/2017 | Farritor | A61B 18/1445 |
| 9,763,741 B2 | 9/2017 | Alvarez et al. | |
| 9,788,910 B2 | 10/2017 | Schuh | |
| 9,818,681 B2 | 11/2017 | Machida | |
| 9,844,412 B2 | 12/2017 | Bogusky et al. | |
| 9,867,635 B2 | 1/2018 | Alvarez et al. | |
| 9,918,659 B2 | 3/2018 | Chopra | |
| 9,918,681 B2 | 3/2018 | Wallace et al. | |
| 9,931,025 B1 | 4/2018 | Graetzel et al. | |
| 9,943,962 B2 | 4/2018 | Sattler et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 9,993,614 B2 | 6/2018 | Pacheco | |
| 10,016,900 B1 | 7/2018 | Meyer et al. | |
| 10,022,192 B1 | 7/2018 | Ummalaneni | |
| 10,029,367 B2 | 7/2018 | Hourtash | |
| 10,046,140 B2 | 8/2018 | Kokish et al. | |
| 10,071,479 B2 | 9/2018 | Swarup et al. | |
| 10,080,576 B2 | 9/2018 | Romo et al. | |
| 10,117,713 B2 | 11/2018 | Moctezuma de la Barrera | |
| 10,130,429 B1 | 11/2018 | Weir | |
| 10,136,949 B2 | 11/2018 | Felder et al. | |
| 10,136,959 B2 | 11/2018 | Mintz et al. | |
| 10,143,360 B2 | 12/2018 | Roelle et al. | |
| 10,145,747 B1 | 12/2018 | Lin et al. | |
| 10,149,720 B2 | 12/2018 | Romo | |
| 10,154,822 B2 | 12/2018 | Henderson | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,213,264 B2 | 2/2019 | Tanner et al. | |
| 10,219,868 B2 | 3/2019 | Weir | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,258,285 B2 | 4/2019 | Hauck | |
| 10,258,425 B2 | 4/2019 | Mustufa et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,314,661 B2 | 6/2019 | Bowling | |
| 10,327,855 B2 | 6/2019 | Hourtash et al. | |
| 10,350,017 B2 | 7/2019 | Bowling | |
| 10,350,390 B2 | 7/2019 | Moll et al. | |
| 10,376,322 B2 * | 8/2019 | Frederick | B25J 9/102 |
| 10,383,765 B2 | 8/2019 | Alvarez et al. | |
| 10,398,518 B2 | 9/2019 | Yu et al. | |
| 10,405,939 B2 | 9/2019 | Romo et al. | |
| 10,405,940 B2 | 9/2019 | Romo | |
| 10,426,559 B2 | 10/2019 | Graetzel et al. | |
| 10,426,661 B2 | 10/2019 | Kintz | |
| 10,434,660 B2 | 10/2019 | Meyer | |
| 10,454,347 B2 | 10/2019 | Covington et al. | |
| 10,463,440 B2 | 11/2019 | Bowling | |
| 10,464,209 B2 | 11/2019 | Ho et al. | |
| 10,470,830 B2 | 11/2019 | Hill | |
| 10,478,595 B2 | 11/2019 | Kokish | |
| 10,482,599 B2 | 11/2019 | Mintz et al. | |
| 10,493,239 B2 | 12/2019 | Hart et al. | |

(56) References Cited

U.S. PATENT DOCUMENTS

| | | | |
|---|---|---|---|
| 10,493,241 B2 | 12/2019 | Jiang | |
| 10,500,001 B2 | 12/2019 | Yu et al. | |
| 10,517,692 B2 | 12/2019 | Eyre et al. | |
| 10,524,866 B2 | 1/2020 | Srinivasan | |
| 10,524,867 B2 | 1/2020 | Kokish et al. | |
| 10,539,478 B2 | 1/2020 | Lin | |
| 10,543,047 B2 | 1/2020 | Yu | |
| 10,543,048 B2 | 1/2020 | Noonan et al. | |
| 10,555,778 B2 | 2/2020 | Ummalaneni et al. | |
| 10,556,092 B2 | 2/2020 | Yu et al. | |
| 10,569,052 B2 | 2/2020 | Kokish et al. | |
| 10,631,949 B2 | 4/2020 | Schuh et al. | |
| 10,639,108 B2 | 5/2020 | Romo et al. | |
| 10,639,109 B2 | 5/2020 | Bovay et al. | |
| 10,639,114 B2 | 5/2020 | Schuh | |
| 10,667,871 B2 | 6/2020 | Romo et al. | |
| 10,667,875 B2 | 6/2020 | DeFonzo | |
| 10,682,189 B2 | 6/2020 | Schuh et al. | |
| 10,687,903 B2 | 6/2020 | Lewis et al. | |
| 10,695,536 B2 | 6/2020 | Weitzner et al. | |
| 10,702,347 B2 * | 7/2020 | Farritor | A61B 34/30 |
| 10,702,348 B2 | 7/2020 | Moll et al. | |
| 10,716,461 B2 | 7/2020 | Jenkins | |
| 10,743,751 B2 | 8/2020 | Landey et al. | |
| 10,744,035 B2 | 8/2020 | Alvarez et al. | |
| 10,820,954 B2 | 11/2020 | Marsot et al. | |
| 10,987,174 B2 | 4/2021 | Draper et al. | |
| 11,013,564 B2 * | 5/2021 | Palmowski | B25J 9/102 |
| 2001/0042643 A1 | 11/2001 | Krueger et al. | |
| 2002/0019644 A1 | 2/2002 | Hastings | |
| 2002/0045905 A1 | 4/2002 | Gerbi et al. | |
| 2002/0098938 A1 | 7/2002 | Milbourne et al. | |
| 2002/0100254 A1 | 8/2002 | Dharssi | |
| 2002/0107573 A1 | 8/2002 | Steinberg | |
| 2002/0111608 A1 | 8/2002 | Baerveldt | |
| 2002/0111621 A1 | 8/2002 | Wallace et al. | |
| 2002/0117017 A1 | 8/2002 | Bernhardt et al. | |
| 2002/0133174 A1 | 9/2002 | Charles et al. | |
| 2002/0161355 A1 | 10/2002 | Wollschlager | |
| 2002/0161426 A1 | 10/2002 | Lancea | |
| 2002/0177789 A1 | 11/2002 | Ferry et al. | |
| 2003/0004455 A1 | 1/2003 | Kadziauskas | |
| 2003/0040681 A1 | 2/2003 | Ng et al. | |
| 2003/0056561 A1 | 3/2003 | Butscher et al. | |
| 2003/0065358 A1 | 4/2003 | Frecker | |
| 2003/0100892 A1 | 5/2003 | Morley et al. | |
| 2003/0109780 A1 | 6/2003 | Coste-Maniere et al. | |
| 2003/0109877 A1 | 6/2003 | Morley | |
| 2003/0109889 A1 | 6/2003 | Mercereau | |
| 2003/0158545 A1 | 8/2003 | Hovda et al. | |
| 2003/0167623 A1 | 9/2003 | Lorenz | |
| 2003/0208189 A1 | 11/2003 | Payman | |
| 2003/0212308 A1 | 11/2003 | Bendall | |
| 2004/0015053 A1 | 1/2004 | Bieger | |
| 2004/0143253 A1 | 7/2004 | Vanney | |
| 2004/0152972 A1 | 8/2004 | Hunter | |
| 2004/0153093 A1 | 8/2004 | Donovan | |
| 2004/0158261 A1 | 8/2004 | Vu | |
| 2004/0186349 A1 | 9/2004 | Ewers | |
| 2004/0193146 A1 | 9/2004 | Lee et al. | |
| 2004/0210116 A1 | 10/2004 | Nakao | |
| 2004/0243147 A1 | 12/2004 | Lipow | |
| 2004/0253079 A1 | 12/2004 | Sanchez | |
| 2004/0254566 A1 | 12/2004 | Plicchi | |
| 2005/0004579 A1 | 1/2005 | Schneider et al. | |
| 2005/0033270 A1 | 2/2005 | Ramans et al. | |
| 2005/0054900 A1 | 3/2005 | Mawn | |
| 2005/0159645 A1 | 7/2005 | Bertolero | |
| 2005/0177026 A1 | 8/2005 | Hoeg et al. | |
| 2005/0183532 A1 | 8/2005 | Najaf et al. | |
| 2005/0222554 A1 | 10/2005 | Wallace et al. | |
| 2005/0240178 A1 | 10/2005 | Morley et al. | |
| 2005/0261705 A1 | 11/2005 | Gist | |
| 2006/0015133 A1 | 1/2006 | Grayzel | |
| 2006/0041245 A1 | 2/2006 | Ferry | |
| 2006/0058813 A1 | 3/2006 | Teague | |
| 2006/0111692 A1 | 5/2006 | Hlavka et al. | |
| 2006/0116693 A1 | 6/2006 | Weisenburgh | |
| 2006/0135963 A1 | 6/2006 | Kick | |
| 2006/0142657 A1 | 6/2006 | Quaid | |
| 2006/0146010 A1 | 7/2006 | Schneider | |
| 2006/0156875 A1 | 7/2006 | McRury et al. | |
| 2006/0161136 A1 | 7/2006 | Anderson et al. | |
| 2006/0161137 A1 | 7/2006 | Orban et al. | |
| 2006/0189891 A1 | 8/2006 | Waxman et al. | |
| 2006/0201688 A1 | 9/2006 | Jenner et al. | |
| 2006/0229587 A1 | 10/2006 | Beyar et al. | |
| 2006/0237205 A1 | 10/2006 | Sia et al. | |
| 2007/0000498 A1 | 1/2007 | Glynn et al. | |
| 2007/0013336 A1 | 1/2007 | Nowlin et al. | |
| 2007/0016164 A1 | 1/2007 | Dudney et al. | |
| 2007/0027443 A1 | 2/2007 | Rose | |
| 2007/0027534 A1 | 2/2007 | Bergheim | |
| 2007/0032906 A1 | 2/2007 | Sutherland et al. | |
| 2007/0060879 A1 | 3/2007 | Weitzner et al. | |
| 2007/0100201 A1 | 5/2007 | Komiya et al. | |
| 2007/0100254 A1 | 5/2007 | Murakami | |
| 2007/0106304 A1 | 5/2007 | Hammack | |
| 2007/0112355 A1 | 5/2007 | Salahieh | |
| 2007/0117655 A1 | 5/2007 | Kasashima et al. | |
| 2007/0119274 A1 | 5/2007 | Devengenzo et al. | |
| 2007/0123855 A1 | 5/2007 | Morley et al. | |
| 2007/0135803 A1 | 6/2007 | Belson | |
| 2007/0149946 A1 | 6/2007 | Viswanathan | |
| 2007/0185485 A1 | 8/2007 | Hauck et al. | |
| 2007/0191177 A1 | 8/2007 | Nagai et al. | |
| 2007/0208375 A1 | 9/2007 | Nishizawa | |
| 2007/0213668 A1 | 9/2007 | Spitz | |
| 2007/0239028 A1 | 10/2007 | Houser | |
| 2007/0239178 A1 | 10/2007 | Weitzner et al. | |
| 2007/0245175 A1 | 10/2007 | Zheng et al. | |
| 2007/0250111 A1 | 10/2007 | Lu | |
| 2007/0299427 A1 | 12/2007 | Yeung et al. | |
| 2008/0015566 A1 | 1/2008 | Livneh | |
| 2008/0021440 A1 | 1/2008 | Solomon | |
| 2008/0033467 A1 | 2/2008 | Miyamoto et al. | |
| 2008/0039255 A1 | 2/2008 | Jinno et al. | |
| 2008/0045981 A1 | 2/2008 | Margolin et al. | |
| 2008/0046122 A1 | 2/2008 | Manzo et al. | |
| 2008/0065103 A1 | 3/2008 | Cooper et al. | |
| 2008/0065111 A1 | 3/2008 | Blumenkranz | |
| 2008/0065112 A1 | 3/2008 | Tovey et al. | |
| 2008/0125698 A1 | 5/2008 | Greg et al. | |
| 2008/0125720 A1 | 5/2008 | Kim et al. | |
| 2008/0147011 A1 | 6/2008 | Urmey | |
| 2008/0177285 A1 | 7/2008 | Brock et al. | |
| 2008/0187101 A1 | 8/2008 | Gertner | |
| 2008/0196533 A1 | 8/2008 | Bergamasco | |
| 2008/0214925 A1 | 9/2008 | Wilson et al. | |
| 2008/0228104 A1 | 9/2008 | Uber et al. | |
| 2008/0243064 A1 | 10/2008 | Stahler et al. | |
| 2008/0249536 A1 | 10/2008 | Stahler et al. | |
| 2008/0253108 A1 | 10/2008 | Yu et al. | |
| 2008/0262301 A1 | 10/2008 | Gibbons et al. | |
| 2008/0287963 A1 | 11/2008 | Rogers et al. | |
| 2008/0302200 A1 | 12/2008 | Tobey | |
| 2009/0005768 A1 | 1/2009 | Sharareh | |
| 2009/0012507 A1 | 1/2009 | Culbertson et al. | |
| 2009/0030446 A1 | 1/2009 | Measamer | |
| 2009/0036900 A1 | 2/2009 | Moll | |
| 2009/0043305 A1 | 2/2009 | Brodbeck | |
| 2009/0082634 A1 | 3/2009 | Kathrani et al. | |
| 2009/0082722 A1 | 3/2009 | Munger et al. | |
| 2009/0088774 A1 | 4/2009 | Swarup et al. | |
| 2009/0098971 A1 | 4/2009 | Ho et al. | |
| 2009/0105645 A1 | 4/2009 | Kidd et al. | |
| 2009/0105723 A1 | 4/2009 | Dillinger | |
| 2009/0131885 A1 | 5/2009 | Akahoshi | |
| 2009/0161827 A1 | 6/2009 | Gertner et al. | |
| 2009/0163948 A1 | 6/2009 | Sunaoshi | |
| 2009/0171371 A1 | 7/2009 | Nixon | |
| 2009/0192524 A1 | 7/2009 | Ltkowitz | |
| 2009/0227998 A1 | 9/2009 | Aljuri | |
| 2009/0247944 A1 | 10/2009 | Kirschenman et al. | |

(56) References Cited

U.S. PATENT DOCUMENTS

| | | |
|---|---|---|
| 2009/0248039 A1 | 10/2009 | Cooper et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0016853 A1 | 1/2010 | Burbank |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0081965 A1 | 4/2010 | Mugan et al. |
| 2010/0082017 A1 | 4/2010 | Zickler |
| 2010/0082041 A1 | 4/2010 | Prisco |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0210923 A1 | 8/2010 | Li et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0228264 A1* | 9/2010 | Robinson .......... A61B 18/1206 |
| | | 606/130 |
| 2010/0248177 A1 | 9/2010 | Mangelberger et al. |
| 2010/0249506 A1 | 9/2010 | Prisco et al. |
| 2010/0268211 A1 | 10/2010 | Manwaring et al. |
| 2010/0274078 A1 | 10/2010 | Kim et al. |
| 2010/0312141 A1 | 12/2010 | Keast et al. |
| 2010/0331858 A1 | 12/2010 | Simaan et al. |
| 2010/0332033 A1 | 12/2010 | Diolaiti |
| 2011/0009863 A1 | 1/2011 | Stanislaw |
| 2011/0015483 A1 | 1/2011 | Barbagli |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028790 A1 | 2/2011 | Farr et al. |
| 2011/0028991 A1 | 2/2011 | Ikeda et al. |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0160713 A1 | 6/2011 | Neuberger |
| 2011/0160745 A1 | 6/2011 | Fielding |
| 2011/0167611 A1 | 7/2011 | Williams |
| 2011/0184391 A1 | 7/2011 | Aljuri |
| 2011/0208211 A1 | 8/2011 | Whitfield et al. |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0238083 A1 | 9/2011 | Moll et al. |
| 2011/0257641 A1 | 10/2011 | Hastings et al. |
| 2011/0261183 A1 | 10/2011 | Ma et al. |
| 2011/0276085 A1 | 11/2011 | Krzyzanowski |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2011/0313343 A1 | 12/2011 | Milutinovic et al. |
| 2012/0004576 A1 | 1/2012 | Govari et al. |
| 2012/0048759 A1 | 3/2012 | Disch et al. |
| 2012/0069167 A1 | 3/2012 | Liu et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0132018 A1 | 5/2012 | Tang |
| 2012/0136419 A1 | 5/2012 | Zarembo et al. |
| 2012/0138586 A1 | 6/2012 | Webster et al. |
| 2012/0138660 A1 | 6/2012 | Shelton, IV et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0209315 A1 | 8/2012 | Amat |
| 2012/0232342 A1 | 9/2012 | Reydel |
| 2012/0232476 A1 | 9/2012 | Bhat et al. |
| 2012/0239012 A1 | 9/2012 | Laurent et al. |
| 2012/0253277 A1 | 10/2012 | Tah et al. |
| 2012/0253332 A1 | 10/2012 | Moll |
| 2012/0259320 A1 | 10/2012 | Loesel et al. |
| 2012/0277730 A1 | 11/2012 | Salahieh |
| 2012/0283747 A1 | 11/2012 | Popovic |
| 2012/0296318 A1 | 11/2012 | Wellhofer et al. |
| 2013/0006144 A1 | 1/2013 | Clancy |
| 2013/0018400 A1 | 1/2013 | Milton et al. |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0066335 A1 | 3/2013 | Barwinkel |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144116 A1 | 6/2013 | Cooper et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0204124 A1 | 8/2013 | Duindam |
| 2013/0225997 A1 | 8/2013 | Dillard et al. |
| 2013/0226151 A1 | 8/2013 | Suehara |
| 2013/0226161 A1 | 8/2013 | Hickenbotham |
| 2013/0231678 A1 | 9/2013 | Wenderow |
| 2013/0233908 A1 | 9/2013 | Knodel |
| 2013/0253267 A1 | 9/2013 | Collins |
| 2013/0303876 A1 | 11/2013 | Gelfand et al. |
| 2013/0304084 A1 | 11/2013 | Beira et al. |
| 2013/0310819 A1 | 11/2013 | Neuberger et al. |
| 2013/0317519 A1 | 11/2013 | Romo et al. |
| 2013/0334281 A1 | 12/2013 | Williams |
| 2013/0345519 A1 | 12/2013 | Piskun et al. |
| 2013/0345686 A1 | 12/2013 | Brown |
| 2014/0000411 A1 | 1/2014 | Shelton, IV et al. |
| 2014/0005681 A1 | 1/2014 | Gee et al. |
| 2014/0039517 A1 | 2/2014 | Bowling |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0066944 A1 | 3/2014 | Taylor et al. |
| 2014/0069437 A1 | 3/2014 | Reis et al. |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0163736 A1 | 6/2014 | Azizian |
| 2014/0166023 A1 | 6/2014 | Kishi |
| 2014/0171778 A1 | 6/2014 | Tsusaka |
| 2014/0180063 A1 | 6/2014 | Zhao |
| 2014/0194859 A1 | 7/2014 | Ianchulev |
| 2014/0194905 A1 | 7/2014 | Kappel |
| 2014/0222019 A1 | 8/2014 | Brudnick |
| 2014/0222207 A1 | 8/2014 | Bowling et al. |
| 2014/0243849 A1 | 8/2014 | Saglam et al. |
| 2014/0246473 A1 | 9/2014 | Auld |
| 2014/0257333 A1 | 9/2014 | Blumenkranz |
| 2014/0275956 A1 | 9/2014 | Fan |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |

(56) References Cited

U.S. PATENT DOCUMENTS

| | | |
|---|---|---|
| 2014/0276723 A1 | 9/2014 | Parihar |
| 2014/0276935 A1 | 9/2014 | Yu |
| 2014/0276936 A1 | 9/2014 | Kokish et al. |
| 2014/0276956 A1 | 9/2014 | Crainich |
| 2014/0277334 A1 | 9/2014 | Yu et al. |
| 2014/0309649 A1 | 10/2014 | Alvarez et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2014/0379000 A1 | 12/2014 | Romo et al. |
| 2015/0012134 A1 | 1/2015 | Robinson |
| 2015/0051592 A1 | 2/2015 | Kintz |
| 2015/0073439 A1 | 3/2015 | Dannaher |
| 2015/0080879 A1 | 3/2015 | Trees |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0127045 A1 | 5/2015 | Prestel |
| 2015/0133960 A1 | 5/2015 | Lohmeier |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0164522 A1 | 6/2015 | Budiman |
| 2015/0164594 A1 | 6/2015 | Romo et al. |
| 2015/0164596 A1 | 6/2015 | Romo et al. |
| 2015/0182250 A1 | 7/2015 | Conlon et al. |
| 2015/0190204 A1 | 7/2015 | Popovi |
| 2015/0201917 A1 | 7/2015 | Snow |
| 2015/0202085 A1 | 7/2015 | Lemonis |
| 2015/0223832 A1 | 8/2015 | Swaney et al. |
| 2015/0231364 A1 | 8/2015 | Blanchard |
| 2015/0314110 A1 | 11/2015 | Park |
| 2015/0335480 A1 | 11/2015 | Alvarez et al. |
| 2015/0366629 A1 | 12/2015 | Bowling |
| 2015/0374445 A1 | 12/2015 | Gombert et al. |
| 2015/0374446 A1 | 12/2015 | Malackowski |
| 2016/0000512 A1 | 1/2016 | Gombert et al. |
| 2016/0001038 A1 | 1/2016 | Romo et al. |
| 2016/0022289 A1 | 1/2016 | Wan |
| 2016/0022466 A1 | 1/2016 | Pedtke |
| 2016/0030014 A1 | 2/2016 | McWeeney et al. |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0128781 A1 | 5/2016 | Blohm et al. |
| 2016/0157945 A1 | 6/2016 | Madhani |
| 2016/0158490 A1 | 6/2016 | Leeflang |
| 2016/0166234 A1 | 6/2016 | Zhang |
| 2016/0183841 A1 | 6/2016 | Duindam et al. |
| 2016/0184032 A1 | 6/2016 | Romo et al. |
| 2016/0192860 A1 | 7/2016 | Allenby |
| 2016/0199984 A1 | 7/2016 | Lohmeier et al. |
| 2016/0206389 A1 | 7/2016 | Miller |
| 2016/0213435 A1 | 7/2016 | Hourtash |
| 2016/0235495 A1 | 8/2016 | Wallace et al. |
| 2016/0242858 A1 | 8/2016 | Moctezuma de la Barrera et al. |
| 2016/0249932 A1 | 9/2016 | Rogers et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0302871 A1 | 10/2016 | Gregerson et al. |
| 2016/0303743 A1 | 10/2016 | Rockrohr |
| 2016/0310146 A1 | 10/2016 | Levy et al. |
| 2016/0331358 A1 | 11/2016 | Gordon |
| 2016/0331477 A1 | 11/2016 | Yu et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0367324 A1 | 12/2016 | Sato et al. |
| 2016/0374541 A1 | 12/2016 | Agrawal et al. |
| 2017/0000577 A1 | 1/2017 | Bowling |
| 2017/0007337 A1 | 1/2017 | Dan |
| 2017/0007343 A1 | 1/2017 | Yu |
| 2017/0020615 A1 | 1/2017 | Koenig et al. |
| 2017/0049471 A1 | 2/2017 | Gaffney et al. |
| 2017/0055995 A1 | 3/2017 | Weier |
| 2017/0065227 A1 | 3/2017 | Marrs |
| 2017/0065364 A1 | 3/2017 | Schuh et al. |
| 2017/0065365 A1 | 3/2017 | Schuh |
| 2017/0071584 A1 | 3/2017 | Suigetsu et al. |
| 2017/0084027 A1 | 3/2017 | Mintz et al. |
| 2017/0086934 A1 | 3/2017 | Devengenzo et al. |
| 2017/0095234 A1 | 4/2017 | Prisco et al. |
| 2017/0095295 A1 | 4/2017 | Overmyer |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0135706 A1 | 5/2017 | Frey |
| 2017/0151028 A1 | 6/2017 | Ogawa et al. |
| 2017/0151416 A1 | 6/2017 | Kutikov |
| 2017/0165009 A1 | 6/2017 | Chaplin et al. |
| 2017/0165011 A1 | 6/2017 | Bovay et al. |
| 2017/0172553 A1 | 6/2017 | Chaplin |
| 2017/0172673 A1 | 6/2017 | Yu et al. |
| 2017/0172680 A1 | 6/2017 | Bowling |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0258534 A1 | 9/2017 | Hourtash |
| 2017/0265923 A1 | 9/2017 | Privitera |
| 2017/0265954 A1 | 9/2017 | Burbank |
| 2017/0281049 A1 | 10/2017 | Yamamoto |
| 2017/0290631 A1 | 10/2017 | Lee et al. |
| 2017/0319289 A1 | 11/2017 | Neff et al. |
| 2017/0325932 A1 | 11/2017 | Hoelzle |
| 2017/0333017 A1* | 11/2017 | Gifford ............ A61B 17/3421 |
| 2017/0333147 A1 | 11/2017 | Bernstein |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0049824 A1 | 2/2018 | Harris |
| 2018/0055583 A1 | 3/2018 | Schuh et al. |
| 2018/0056044 A1 | 3/2018 | Choi et al. |
| 2018/0079090 A1 | 3/2018 | Koenig et al. |
| 2018/0080841 A1 | 3/2018 | Cordoba |
| 2018/0104820 A1 | 4/2018 | Troy et al. |
| 2018/0116735 A1 | 5/2018 | Tierney et al. |
| 2018/0140371 A1 | 5/2018 | Hares et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0193049 A1 | 7/2018 | Heck et al. |
| 2018/0206927 A1 | 7/2018 | Prisco et al. |
| 2018/0206931 A1 | 7/2018 | Scheib |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0243048 A1 | 8/2018 | Shan |
| 2018/0250083 A1 | 9/2018 | Schuh et al. |
| 2018/0250085 A1 | 9/2018 | Simi |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1* | 10/2018 | Draper ................. A61B 34/30 |
| 2018/0296285 A1 | 10/2018 | Simi et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |

(56) References Cited

U.S. PATENT DOCUMENTS

| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0015166 A1 | 1/2019 | Mahoney |
| 2019/0069962 A1 | 3/2019 | Tabandeh et al. |
| 2019/0083183 A1 | 3/2019 | Moll et al. |
| 2019/0099231 A1 | 4/2019 | Bruehwiler |
| 2019/0099232 A1 | 4/2019 | Soto et al. |
| 2019/0105776 A1 | 4/2019 | Ho et al. |
| 2019/0105785 A1 | 4/2019 | Meyer et al. |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0117320 A1 | 4/2019 | Shoham et al. |
| 2019/0117324 A1 | 4/2019 | Hibner |
| 2019/0142537 A1 | 5/2019 | Covington et al. |
| 2019/0151148 A1 | 5/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0192249 A1 | 6/2019 | Bowling |
| 2019/0216548 A1 | 7/2019 | Ummalaneni |
| 2019/0216550 A1 | 7/2019 | Eyre et al. |
| 2019/0216576 A1 | 7/2019 | Eyre |
| 2019/0223967 A1 | 7/2019 | Abbott |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0231458 A1 | 8/2019 | DiMaio |
| 2019/0231460 A1 | 8/2019 | DiMaio |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298464 A1 | 10/2019 | Abbott |
| 2019/0298465 A1 | 10/2019 | Chin |
| 2019/0298469 A1 | 10/2019 | Ramstad et al. |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0008874 A1 | 1/2020 | Barbagli et al. |
| 2020/0022767 A1 | 1/2020 | Hill |
| 2020/0030046 A1 | 1/2020 | Bowling |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh et al. |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0129252 A1 | 4/2020 | Kokish |
| 2020/0138531 A1 | 5/2020 | Chaplin |
| 2020/0146769 A1 | 5/2020 | Eyre |
| 2020/0155245 A1 | 5/2020 | Yu |
| 2020/0155801 A1 | 5/2020 | Kokish |
| 2020/0163726 A1 | 5/2020 | Tanner |
| 2020/0170720 A1 | 6/2020 | Ummalaneni |
| 2020/0171660 A1 | 6/2020 | Ho |
| 2020/0188043 A1 | 6/2020 | Yu |
| 2020/0197109 A1 | 6/2020 | Chaplin |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |
| 2020/0383735 A1 | 12/2020 | Lewis et al. |
| 2020/0405317 A1 | 12/2020 | Wallace |
| 2020/0405413 A1 | 12/2020 | Kokish |
| 2020/0405419 A1 | 12/2020 | Mao |
| 2020/0405420 A1 | 12/2020 | Purohit |
| 2020/0405423 A1 | 12/2020 | Schuh |
| 2020/0405424 A1 | 12/2020 | Schuh |
| 2020/0405434 A1 | 12/2020 | Schuh |
| 2020/0406002 A1 | 12/2020 | Romo |
| 2021/0153956 A1 | 5/2021 | Draper et al. |

FOREIGN PATENT DOCUMENTS

| CN | 100515347 | 7/2009 |
| CN | 103037799 | 4/2011 |
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102834043 | 12/2012 |
| CN | 102973317 | 3/2013 |
| CN | 102015759 | 4/2013 |
| CN | 103298414 | 9/2013 |
| CN | 103735313 | 4/2014 |
| CN | 104619281 | 5/2015 |
| CN | 105147393 | 12/2015 |
| CN | 105559850 | 5/2016 |
| CN | 105559886 | 5/2016 |
| CN | 205729413 | 11/2016 |
| CN | 1006170266 A | 11/2016 |
| CN | 107106207 A | 8/2017 |
| DE | 19649082 | 1/1998 |
| DE | 102004020465 | 9/2005 |
| EP | 1 321 106 | 6/2003 |
| EP | 1321106 A1 | 6/2003 |
| EP | 1 442 720 | 8/2004 |

(56)            References Cited

FOREIGN PATENT DOCUMENTS

| EP | 1 849 423 | | 10/2007 |
|----|-----------|---|---------|
| EP | 2 567 670 | | 3/2013 |
| EP | 3 025 630 | | 6/2016 |
| EP | 3606400 | B1 | 3/2022 |
| JP | 07-136173 | | 5/1995 |
| JP | 2005-270464 | | 10/2005 |
| JP | 2009-139187 | | 6/2009 |
| JP | 2010-046384 | | 3/2010 |
| JP | 2014-159071 | | 9/2014 |
| JP | 2015-181495 | | 10/2015 |
| WO | WO 94/14494 | | 7/1994 |
| WO | 9823216 | A1 | 6/1998 |
| WO | WO 02/74178 | | 9/2002 |
| WO | WO 07/146987 | | 12/2007 |
| WO | 2007136984 | A3 | 1/2009 |
| WO | WO 09/092059 | | 7/2009 |
| WO | 2009158164 | A1 | 12/2009 |
| WO | 2009109532 | A9 | 3/2010 |
| WO | 2010093153 | A2 | 8/2010 |
| WO | 2010133733 | A1 | 11/2010 |
| WO | WO 10/133982 | | 11/2010 |
| WO | WO 11/005335 | | 1/2011 |
| WO | 2011037718 | A1 | 3/2011 |
| WO | 2011058530 | A1 | 5/2011 |
| WO | WO 11/161218 | | 12/2011 |
| WO | 2012018816 | A2 | 2/2012 |
| WO | 2012035923 | A1 | 3/2012 |
| WO | WO 12/037506 | | 3/2012 |
| WO | 2012040233 | A3 | 5/2012 |
| WO | WO 13/107468 | | 7/2013 |
| WO | 2013130895 | A1 | 9/2013 |
| WO | 2013154708 | A1 | 10/2013 |
| WO | WO 13/179600 | | 12/2013 |
| WO | 2015052629 | A1 | 4/2015 |
| WO | WO 15/127231 | | 8/2015 |
| WO | 2015142798 | A1 | 9/2015 |
| WO | 2015142812 | A1 | 9/2015 |
| WO | WO 15/153174 | | 10/2015 |
| WO | 2016100181 | A1 | 6/2016 |
| WO | WO 16/137612 | | 9/2016 |
| WO | WO 17/059412 | | 4/2017 |
| WO | WO 17/114855 | | 7/2017 |
| WO | WO 17/151993 | | 9/2017 |
| WO | WO 18/069679 | | 4/2018 |
| WO | 2018187069 | A1 | 10/2018 |
| WO | WO 18/189722 | | 10/2018 |

OTHER PUBLICATIONS

Hernansanz et al, 2015, A multi-robot cooperation strategy for dexterous task oriented teleoperation, 2015, Elsevier, Robotics and Autonomous Systems, 68(205):156-172.

Ramezanifard et al, 2007, A Novel Modeling Approach for Collision Avoidance in Robotic Surgery, 2007 Science Publications, American Journal of Applied Sciences 4(9):693-699.

International search report and written opinion dated Sep. 28, 2020 in application No. PCT/IB2020/056071.

Preliminary Report and Written Opinion for appl No. PCT/IB2020/056071, dated Jan. 6, 2022, 10 pages.

Mayo Clinic, Robotic Surgery, https://www.mayoclinic.org/tests-procedures/robotic-surgery/about/pac-20394974?p=1, downloaded from the internet on Jul. 12, 2018, 2 pp.

CN office action and search report for Appl. No. 201880030342.4, dated May 7, 2021, 22 pages.

JP Office Action for appl No. 2019-554851, dated Jan. 25, 2022, 13 pages.

Advisory Action for U.S. Appl. No. 15/935,955, dated Sep. 3, 2019, 2 pages.

Final Rejection for U.S. Appl. No. 15/935,955, dated Jun. 13, 2019, 21 pages.

EP Examination Report for Appl. No. 22160897.9, dated Nov. 9, 2023, 3 pages.

Non-Final Rejection for U.S. Appl. No. 15/935,955, dated Jan. 24, 2019, 18 pages.

Non-Final Rejection for U.S. Appl. No. 15/935,955, dated Mar. 5, 2020, 11 pages.

Notice of Allowance for U.S. Appl. No. 15/935,955, dated Aug. 21, 2020, 10 pages.

Notice of Allowance for U.S. Appl. No. 15/935,955, dated Dec. 23, 2020, 3 pages.

EP Search Report for Appl. No. 22160897.9, dated Jun. 2, 2022, 7 pages.

JP Office Action for Appl. No. 2019-554851, dated Oct. 18, 2022, 9 pages.

AU Examination Report for Appl. No. 2018250049, dated Jan. 20, 2023, 3 pages.

AU Notice of Acceptance for Appl. No. 2018250049, dated Jun. 16, 2023, 3 pages.

Notice of Allowance from U.S. Appl. No. 17/167,468, dated May 12, 2025, 11 pages.

First Office Action from Chinese Patent Application No. 202080047630.8, dated Apr. 1, 2025, 6 pages.

Second Office Action from Chinese Patent Application No. 202080047630.8, dated Aug. 14, 2025, 10 pages.

Notification to Grant Patent Right for Invention from Chinese Patent Application No. 202080047630.8, dated Feb. 6, 2026, 6 pages.

* cited by examiner

100

110

105

101

115

140

102

100

110

105

175

175

301

101

115

175

140

102

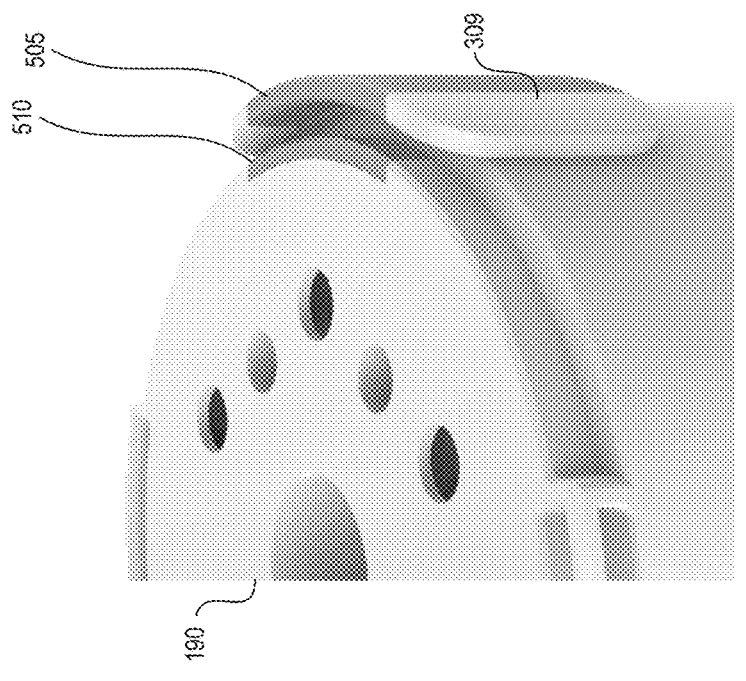
FIG. 7F
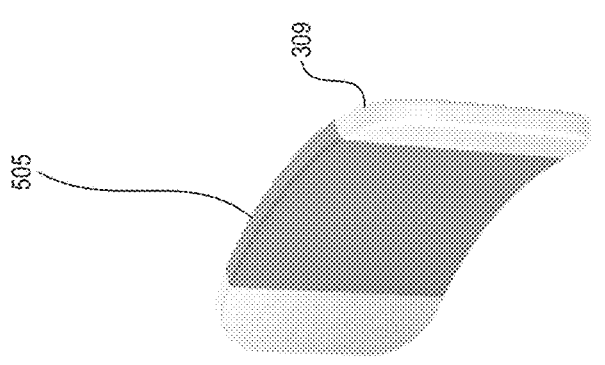
FIG. 7E
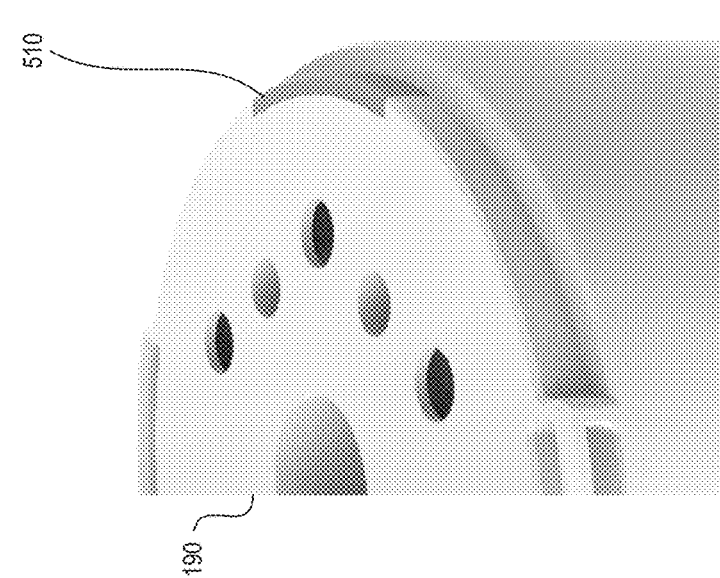

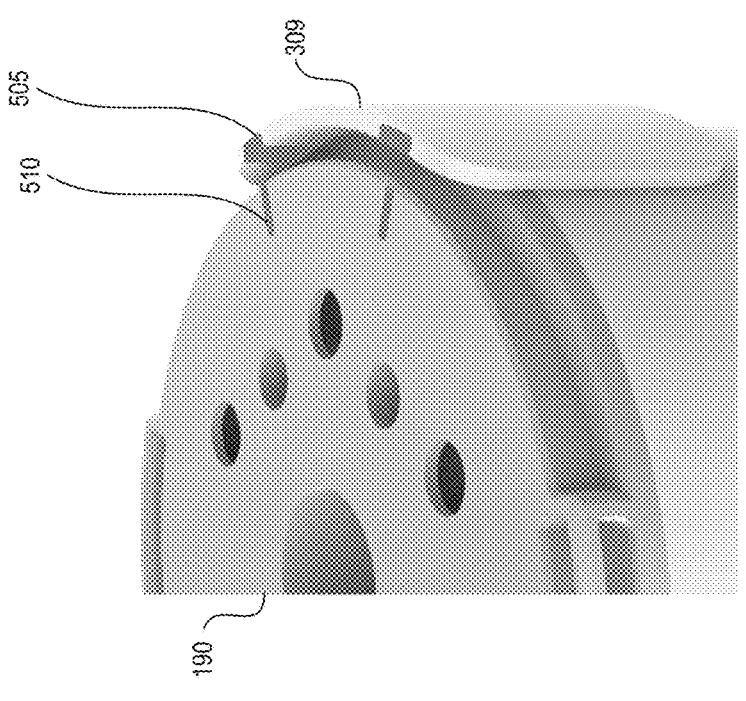
FIG. 7H
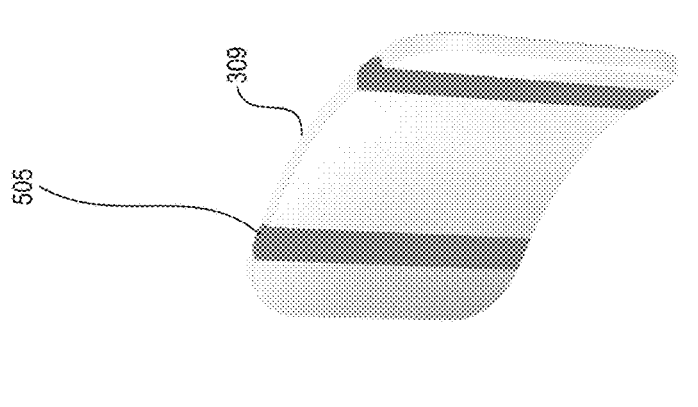
FIG. 7G
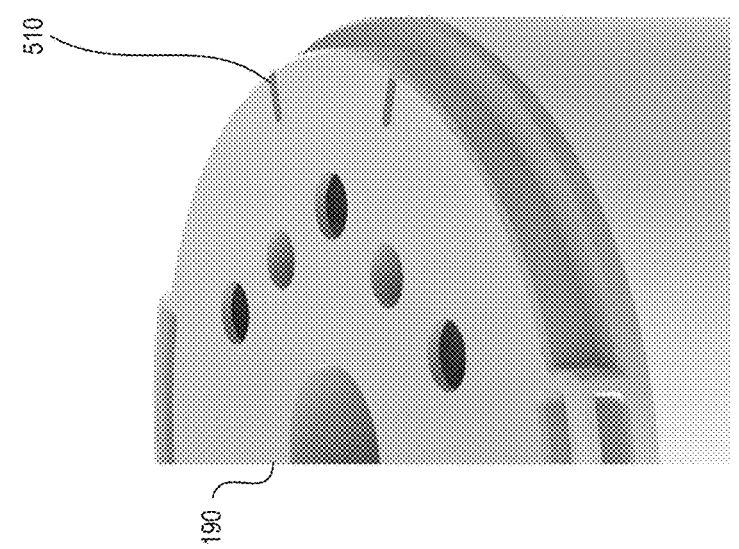

700

701
START

705
INSTALL SURGICAL TUBE IN PATIENT

710
ATTACH THE PATIENT INTRODUCER
HOLDER TO BED RAIL

715
CONNECT PATIENT INTRODUCER TO
PATIENT INTRODUCER HOLDER

720
ATTACH THE PATIENT INTRODUCER TO THE
SURGICAL TUBE

725
END

800

801
START

805
CONNECT UMBILICAL CABLE TO SURGICAL CART

810
POWER ON THE SURGICAL CART

815
SELECT ARM OF THE SURGICAL CART TO BE USED IN ALIGNMENT

820
PLACE THE SELECTED ARM INTO ALIGNMENT POSE

825
END

PATIENT INTRODUCER FOR A ROBOTIC SYSTEM

CROSS REFERENCE TO RELATED APPLICATIONS

This application claims the benefit of priority to U.S. Provisional Application No. 62/868,796 the entire contents of which are incorporated by reference herein. This application is related to U.S. Non-Provisional application Ser. No. 15/935,955, filed Mar. 26, 2018, which claims the benefit of priority to U.S. Provisional Application No. 62/483,279, the entire contents of each of which are incorporated by reference herein.

TECHNICAL FIELD

Disclosed embodiments relate to medical technology, such as, for example, a patient introducer for a robotic system.

BACKGROUND

Medical procedures such as endoscopy (e.g., bronchoscopy) may involve accessing and visualizing the inside of a patient's luminal network (e.g., airways) for diagnostic and/or therapeutic purposes. Surgical robotic systems may be used to control the insertion and/or manipulation of a surgical tool, such as, for example, an endoscope during an endoscopic procedure. The surgical robotic system may comprise at least one robotic arm including a manipulator assembly used to control the positioning of the surgical tool during the procedure. The surgical tool may be introduced into the patient's luminal network via a patient introducer which may receive and guide the surgical tool from the manipulator assembly into the patient's luminal network.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIGS. 7A-7H illustrate embodiments of alignment markings which may be used to aid in rotational alignment of a manipulator assembly with an alignment member in accordance with aspects of this disclosure.

DETAILED DESCRIPTION

Figure 1A:
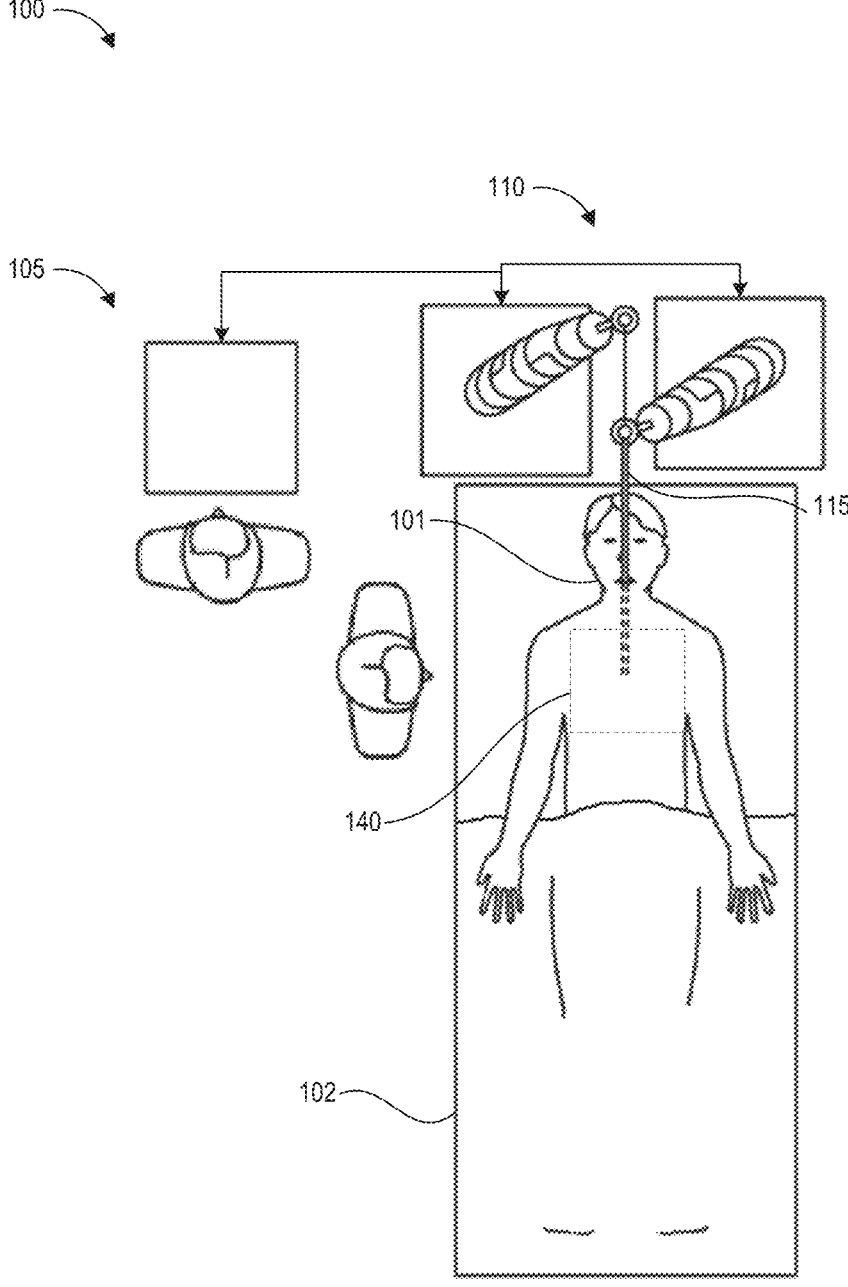
FIG. 1A illustrates an example operating environment including an example surgical robotic system in accordance with aspects of this disclosure.

Embodiments of this disclosure relate to systems and techniques that facilitate the alignment of a patient introducer with a surgical robotic system. A patient introducer may function as a guide for a surgical tool (e.g., an endoscopic tool) and may guide the surgical tool into a port (e.g., an endrotracheal tube) to introduce the endoscopic tool into a patient. As used herein, a "port" may refer to a device that can be installed on a patient to provide access to an internal anatomy by one or more medical tools. For example, a port may be partially insertable into of a lumen of a patient, so that the port is configured to guide a surgical tool into a surgical site. Additional examples of ports include but are not limited to endrotracheal tubes, gastrointestinal tubes, cannulas, cystoscopy sheaths, and the like. Certain embodiments of the patient introducer may guide the surgical tool along a curved path, where the entry and exit points of the patient introducer are formed along the curved path, rather than along a straight line. This curvature of the patient introducer enables arms of a surgical robot to be positioned outside of a straight line extending from the port, providing for more practical and/or convenient placement of a surgical robotic system cart to which the robotic arms are attached. That is, without the curved entry provided by the patient introducer, it may be necessary for the arms of the surgical robotic system to be substantially aligned with an axis of the port for proper control the surgical tool, which may not be practical under certain circumstances.

According to some embodiments, the patient introducer may be mounted to a robotic arm of the robotic system. The robotic arm can be utilized to position the introducer to, for example, align the introducer with respect to the patient, with respect to the port, or with respect to a separate robotic arm that manipulates the medical tool through the introducer and into the patient. Such a robot arm mounting for the patient introducer can reduce a set up time required to initiate a medical procedure, improve usability of the robotic system, enhance positioning accuracy of various system components, or allow for dynamic positioning of the introducer during a procedure.

According to some embodiments, the patient introducer may be releasably attached to a modular attachment interface of the robotic arm to permit the robotic arm to be used for other purposes when not used by the patient introducer. The patient introducer may include an introducer tube attachable to the robotic arm via an instrument base that can attach to the robotic arm without a need for an operative coupling to drive mechanisms on the robotic arm attachment interface. The introducer tube can be movable along the instrument base to different positions or orientations. The instrument base can be permanently fixed to the introducer tube or a detachable adapter. The attachable adapter can permit the introducer tube to be removed from the adapter instrument base to permit the introducer tube to be repositioned on a different mount on the instrument base or to permit other devices to be attached to the adapter instrument base.

Various embodiments incorporating these and other features will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

As used herein, the term "approximately" refers to a range of measurements of a length, thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

Overview of Example Surgical Robotic Systems

The embodiments discussed herein, although described in connection with a bronchoscopy embodiment, may also cover other types of medical or surgical procedures that may be performed by a surgical robotic system, such as cardiology, urology, gastroenterology, laparoscopy, and/or other related or similar surgical procedures including surgical procedures in which a surgical tool is introduced into a patient's body via, for example, a port installed on and/or partially inserted into the patient's body.

FIG. 1A illustrates an example operating environment implementing one or more aspects of the disclosed surgical robotic systems and techniques. The operating environment 100 includes a patient 101, a platform 102 (also referred to as a table or bed) supporting the patient 101, a surgical robotic system 110 (also referred to as a medical robotic system or simply as a robotic system) guiding movement of a surgical tool 115 (e.g., an endoscopic tool, also referred to simply as an endoscope 115), and a command center 105 for controlling operations of the surgical robotic system 110. FIG. 1A also illustrates an outline of a region of a luminal network 140 within the patient 101, shown in more detail in FIG. 1B.

The surgical robotic system 110 can include one or more robotic arms for positioning and guiding movement of the endoscope 115 through the luminal network 140 of the patient 101. Command center 105 can be communicatively coupled to the surgical robotic system 110 for receiving position data and/or providing control signals from a user. As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like. The surgical robotic system 110 is discussed in more detail with respect to FIG. 1C, and the command center 105 is discussed in more detail with respect to FIG. 2.

The endoscope 115 may be a flexible elongate medical tool, such as, for example, a tubular and flexible surgical instrument that, in use, is inserted into the anatomy of a patient to capture images of the anatomy (e.g., body tissue) and/or to provide a working channel for insertion of other medical instruments to a target tissue site. In some implementations, the endoscope 115 can be a bronchoscope. The endoscope 115 can include one or more imaging devices (e.g., cameras or other types of optical sensors) at its distal end. The imaging devices may include one or more optical components such as an optical fiber, fiber array, photosensitive substrate, and/or lens(es) that can be configured for visualization of an internal anatomy of a patient. The optical components can move along with the tip of the endoscope 115 such that movement of the tip of the endoscope 115 results in corresponding changes to the field of view of the images captured by the imaging devices.

Figure 1B:
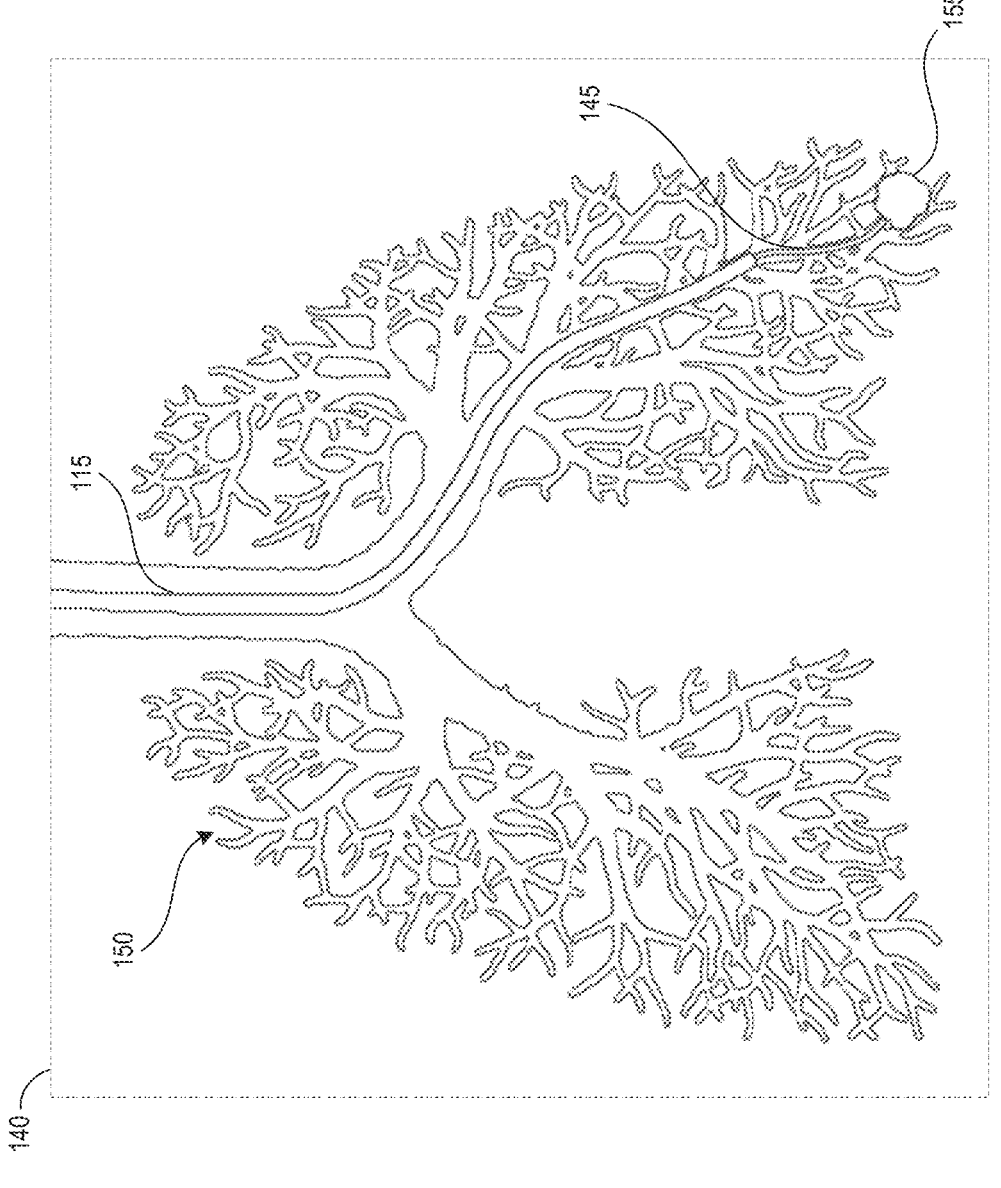
FIG. 1B illustrates an example luminal network that can be navigated in the operating environment of FIG. 1A.

FIG. 1B illustrates an example luminal network that can be navigated in the operating environment of FIG. 1A. The luminal network 140 includes the branched structure of the airways 150 of the patient 101 and a lesion 155 that can be accessed as described herein for diagnosis and/or treatment. As illustrated, the lesion 155 is located at the periphery of the airways 150. In some embodiments, the endoscope 115 has an outer sheath portion 147 with a first diameter that is less than a diameter of branches at the periphery of the airways, and thus the distal end of the outer sheath portion 147 may not able to be positioned through the smaller-diameter airways around the lesion 155. Accordingly, the endoscope 115 can include an inner leader portion 145 having a smaller diameter than the outer sheath portion 147. The inner leader portion 145 can be a steerable elongate tool such as a steerable catheter that extends from an outer sheath portion 147 of the endoscope 115 or from the working channel of the endoscope 115 the remaining distance to the lesion 155. The steerable catheter may have a lumen through which instruments, for example biopsy needles, cytology brushes, and/or tissue sampling forceps, can be passed to the target tissue site of lesion 155. In such implementations, either or both the distal end of the outer sheath portion 147 of the endoscope 115 and the distal end of the inner leader portion 145 can be provided with electro-magnetic (EM) sensors for tracking their position within the airways 150. In some embodiments, each of the outer sheath portion 147 and the inner leader portion 145 of the endoscope 115 can be steered or driven independently via separate robotic arms. The leader portion 145 can be configured with optical components of the endoscope (e.g., as described above), that are configured to provide visualization of an internal anatomy of the patient. In some embodiments, the overall diameter of the endoscope 115 may be small enough to reach the periphery without the steerable catheter, or may be small enough to get close to the periphery (e.g., within 2.5-3 cm) to deploy medical instruments through a non-steerable catheter.

In some embodiments, a 2D display of a 3D luminal network model as described herein, or a cross-section of a 3D model, can resemble FIG. 1B.

Figure 1C:
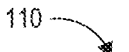
FIG. 1C illustrates an example robotic arm of a robotic surgical system for guiding surgical tool movement through the luminal network of FIG. 1B.
Figure 1C:
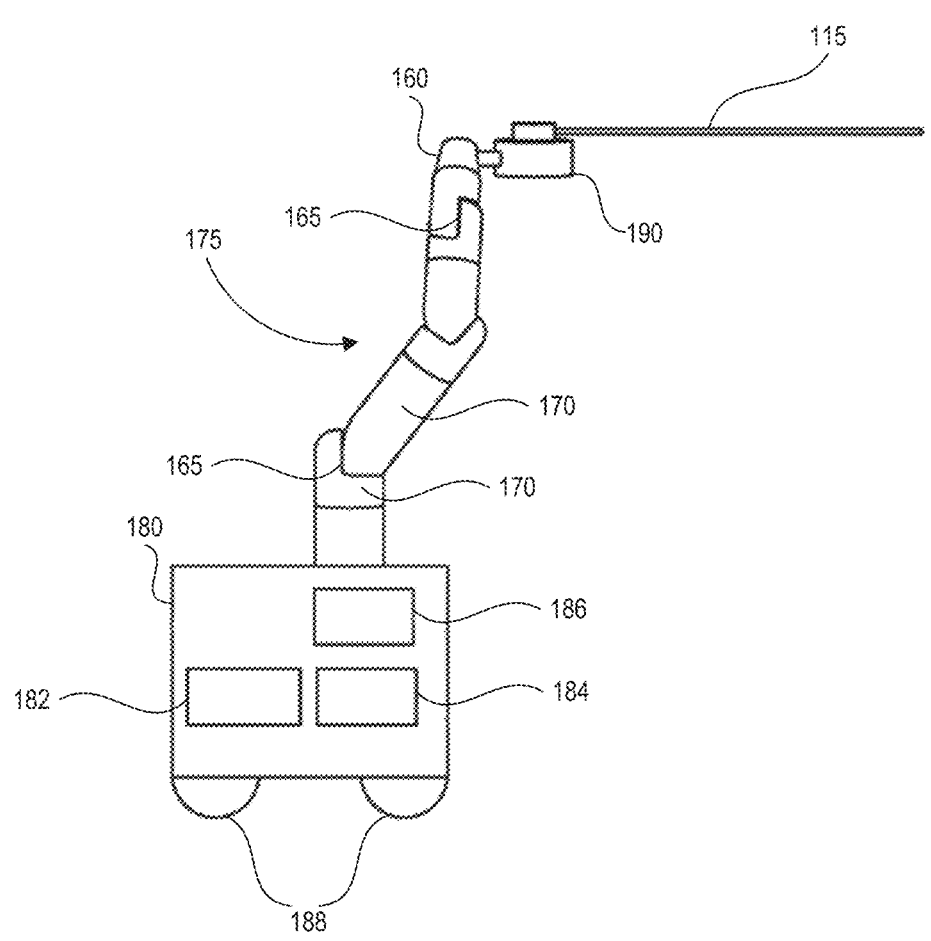

FIG. 1C illustrates an example robotic arm of a surgical robotic system for guiding surgical tool movement through the luminal network of FIG. 1B. The surgical robotic system 110 may include a robot base 180, for example, a surgical robotic system cart (also referred to simply as a cart) coupled to one or more robotic arms, e.g., robotic arm 175 (also referred to simply as an arm). The robot base 180 can provide a support structure that supports robotic arms 175 mounted thereto, such that the robot base 180 can hold the robot arms 175 during use. Although the embodiments discussed herein are described with respect to the specific embodiment of a cart approach (e.g., the robot base is a movable cart, and the robotic arms 175 are positioned on the surgical robotic system cart), other embodiments of this disclosure may also relate to other approaches, such as, for example, a table approach in which the robot base 180 is a table. In a table approach, the patient 101 lies on a table (e.g., the patient is supported by the platform 102) and the robotic arms 175 are also attached to the table.

The robotic arm 175 includes multiple arm segments 170 coupled at joints 165, which provides the robotic arm 175 multiple degrees of freedom. Each joint 165 can be, for example, a rotary joint or prismatic joint that allows relative movement between a set of coupled arm segments. As an example, one implementation of the robotic arm 175 can have seven degrees of freedom corresponding to seven arm segments. In some embodiments, the robotic arm 175 includes set up joints that use a combination of brakes and counter-balances to maintain a position of the robotic arm 175. The counter-balances may include gas springs or coil springs. The brakes, e.g., fail safe brakes, may include mechanical and/or electrical components. Further, the robotic arm 175 may be gravity-assisted passive support type robotic arm.

The robotic arm 175 may include or be otherwise coupled to a manipulator. For example, the robotic arm 175 can be coupled to a manipulator assembly (e.g., an instrument device manipulator (IDM) 190) using a mechanism changer interface (MCI) 160. As used herein, a "manipulator assembly" may refer to an IDM 190 and any other instruments connected or integrated with the IDM 190. For example, a sterile adaptor may be connected to the IDM 190 for certain surgical procedures where sterility is necessary for the manipulator assembly. The sterile adaptor may be part of, for example, a sterile drape that covers one or more component (s) of a surgical robotic system and may facilitate maintaining a sterile interface between the IDM 190 and one or more components of the robotic arm 175 or surgical tool 115, thereby providing a barrier between non-sterile component (s) of the robotic system and a sterile surgical zone or area. The sterile adaptor may cover certain markings on the IDM 190, and thus, in some embodiments, the sterile adaptor may include markings formed thereon. The markings on the sterile adaptor may be located in positions that correspond to the markings on the IDM 190. The IDM 190 can be removed and replaced with a different type of IDM, for example, a first type of IDM configured to manipulate an endoscope or a second type of IDM configured to manipulate a laparoscope. The MCI 160 includes connectors to transfer pneumatic pressure, electrical power, electrical signals, and/or optical signals from the robotic arm 175 to the IDM 190. The MCI 160 can be a set screw or base plate connector. The IDM 190 can manipulate surgical tools or instruments, for example the endoscope 115, using techniques including direct drive, harmonic drive, geared drives, belts and pulleys, magnetic drives, and the like. In certain implementations, the MCI 160 is interchangeable based on the type of IDM 190 and can be customized for a certain type of surgical procedure. The robotic arm 175 can include a joint level torque sensing and a wrist at a distal end.

Robotic arm 175 of the surgical robotic system 110 can manipulate the endoscope 115 using elongate movement members. The elongate movement members may include pull wires, also referred to as pull or push wires, cables, fibers, or flexible shafts. For example, the robotic arm 175 can actuate multiple pull wires coupled to the endoscope 115 to deflect the tip of the endoscope 115. The pull wires may include both metallic and non-metallic materials, for example, stainless steel, Kevlar, tungsten, carbon fiber, and/or the like. The endoscope 115 may exhibit nonlinear behavior in response to forces applied by the elongate movement members. The nonlinear behavior may be based on stiffness and compressibility of the endoscope 115, as well as variability in slack or stiffness between different elongate movement members.

The robot base 180 can be positioned such that the robotic arm 175 has access to perform or assist with a surgical procedure on a patient, while a user such as a physician may control the surgical robotic system 110 from the comfort of the command console 105. In some embodiments, the robot base 180 may be coupled to a surgical operating table or bed for supporting the patient 101. The robot base 180 can be communicatively coupled to the command console 105 shown in FIG. 1A.

The robot base 180 can house functional components, such as power supplies, processing circuits, memories, circuitry, pumping units, fluid reservoirs, and/or other operative components useful for operating the robotic arm(s) or supporting a medical procedure. For example, the robot base 180 can include a source of power 182, pneumatic pressure 186, and/or control and sensor electronics 184—including components such as, e.g., a central processing unit (also referred to simply as a processor), data bus, control circuitry, and/or memory—and related actuators such as motors to move the robotic arm 175. In some embodiments, one or more of such functional components can be included on a separate control tower that may be communicatively or operably coupled to the robot base 180.

The electronics 184 can implement navigation control techniques, safety modes, and/or data filtering techniques. The electronics 184 in the robot base 180 may also process and transmit control signals communicated from the command console 105. In some embodiments, the robot base 180 includes wheels 188 to transport the surgical robotic system 110 and wheel locks/brakes (not shown) for the wheels 188. Mobility of the surgical robotic system 110 helps accommodate space constraints in a surgical operating room as well as facilitate appropriate positioning and movement of surgical equipment in order to align the robot base 180 and/or IDM 190 with the patient. Further, the mobility allows the robotic arm 175 to be aligned with the patient 101 and/or the platform 102 such that the robotic arm 175 does not interfere with the patient, physician, anesthesiologist, or any other equipment during procedures. A user may control the robotic arm 175 using control devices, for example the command console in order to perform various procedures.

Figure 2:
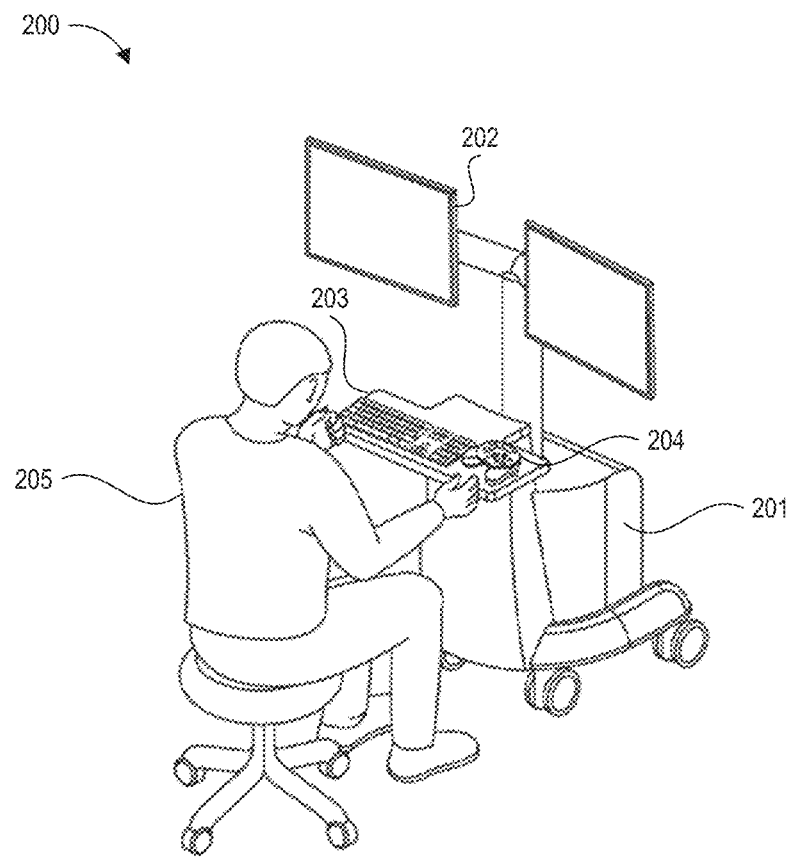
FIG. 2 illustrates an example command console that can be used in the example operating environment of FIG. 1A.

FIG. 2 illustrates an example command console 200 that can be used, for example, as the command console 105 in the example operating environment 100. The command console 200 includes a console base 201, display modules 202, e.g., monitors, and control modules or input devices, e.g., a keyboard 203 and/or a joystick 204. In some embodiments, one or more of the command console 200 functionality may be integrated into a robot base 180 of the surgical robotic system 110 or another system communicatively coupled to the surgical robotic system 110. A user 205, e.g., a physician, may remotely control the surgical robotic system 110 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 115 shown in FIGS.

1A-1C. In some embodiments, both the console base 201 and the robot base 180 perform signal processing for load-balancing. The console base 201 may also process commands and instructions provided by the user 205 through the control modules 203 and 204. In addition to, or as an alternative to, the keyboard 203 and joystick 204 shown in FIG. 2, the control modules may include devices such as one or more computer mice, trackpads, trackballs, control pads, video game controllers, sensors (e.g., motion sensors or cameras) that capture hand gestures and finger gestures, handheld controllers, and/or gimbals.

In some embodiments, the user 205 can control a surgical instrument such as the endoscope 115 using the command console 200 in a velocity mode or position control mode. In velocity mode, the user 205 directly controls pitch and yaw motion of a distal end of the endoscope 115 based on direct manual control using the control modules. For example, movement on the joystick 204 may be mapped to yaw and pitch movement in the distal end of the endoscope 115. The joystick 204 can provide haptic feedback to the user 205. For example, the joystick 204 may vibrate to indicate that the endoscope 115 cannot further translate or rotate in a certain direction. The command console 200 can also provide visual feedback (e.g., pop-up messages) and/or audio feedback (e.g., beeping or other audible alert) to indicate that the endoscope 115 has reached maximum translation or rotation. The haptic and/or visual feedback can also be provided due to the system operating in a safety mode during patient expiration as described in more detail below.

In position control mode, the command console 200 uses a three-dimensional (3D) map of a patient luminal network and input from navigational sensors as described herein to control a surgical tool or instrument, e.g., the endoscope 115. The command console 200 provides control signals to robotic arms 175 of the surgical robotic system 110 to manipulate the endoscope 115 to a target location. Due to the reliance on the 3D map, position control mode may require accurate mapping of the anatomy of the patient 101.

In some embodiments, users 205 can manually manipulate robotic arms 175 of the surgical robotic system 110 without using the command console 200. For example, the IDM 190, robotic arm, and/or another portion of the surgical robotic system 110 may include an admittance button 410 (shown in the examples of FIGS. 4C and 6B) which the user can push to begin manual control of one or more of the robotic arms 175. In one embodiment, while the user continuously pressed the admittance button 410, a corresponding robotic arm 175 may allow the user 205 to manually position the IDM 190 by applying physical force to the IDM 190 and/or the robotic arm 175. As described above, the robotic arm 175 may include brake(s) and/or counter balances used to maintain the position and/or orientation of the robotic arm 175. In certain embodiments, the admittance button 410, when actuated by a user (e.g., when receiving an input from a user), may at least partially disengage the brake to allow for movement of the robotic arm 175 in response to an external force applied thereto. In some embodiments, the robotic arm 175 may include an actuator configured to apply a torque to the robotic arm 175 to maintain the spatial positioning and orientation of the robotic arm 175. The robotic arm 175 may be configured to reduce the torque applied to the robotic arm 175 by the actuator, in response to the admittance button 410 receiving input from a user, to allow for movement of the robotic arm 175 in response to an external force applied thereto.

During setup in a surgical operating room, the users 205 may move the robotic arms 175, endoscopes 115, and other surgical equipment to access a patient. Setup may also involve a step of aligning portion(s) of the surgical robotic system 110 with the patient 101, the platform 102, and/or a patient introducer, as discussed in detail below. The surgical robotic system 110 may rely on force feedback and inertia control from the users 205 to determine appropriate configuration of the robotic arms 175 and equipment.

The displays 202 may include one or more electronic monitors (e.g., LCD displays, LED displays, touch-sensitive displays), virtual reality viewing devices, e.g., goggles or glasses, and/or other display devices. In some embodiments, the display modules 202 are integrated with the control modules, for example, as a tablet device with a touchscreen. In some embodiments, one of the displays 202 can display a 3D model of the patient's luminal network and virtual navigation information (e.g., a virtual representation of the end of the endoscope within the model based on EM sensor position) while the other of the displays 202 can display image information received from the camera or another sensing device at the end of the endoscope 115. In some implementations, the user 205 can both view data and input commands to the surgical robotic system 110 using the integrated displays 202 and control modules. The displays 202 can display 2D renderings of 3D images and/or 3D images using a stereoscopic device, e.g., a visor or goggles. The 3D images provide an "endo view" (i.e., endoscopic view), which is a computer 3D model illustrating the anatomy of a patient. The "endo view" provides a virtual environment of the patient's interior and an expected location of an endoscope 115 inside the patient. A user 205 compares the "endo view" model to actual images captured by a camera to help mentally orient and confirm that the endoscope 115 is in the correct—or approximately correct—location within the patient. The "endo view" provides information about anatomical structures, e.g., the shape of airways, circulatory vessels, or an intestine or colon of the patient, around the distal end of the endoscope 115. The display modules 202 can simultaneously display the 3D model and CT scans of the anatomy the around distal end of the endoscope 115. Further, the display modules 202 may overlay the already determined navigation paths of the endoscope 115 on the 3D model and/or CT scans.

In some embodiments, a model of the endoscope 115 is displayed with the 3D models to help indicate a status of a surgical procedure. For example, the CT scans can identify a lesion in the anatomy where a biopsy may be necessary. During operation, the display modules 202 may show a reference image captured by the endoscope 115 corresponding to the current location of the endoscope 115. The display modules 202 may automatically display different views of the model of the endoscope 115 depending on user settings and a particular surgical procedure. For example, the display modules 202 show an overhead fluoroscopic view of the endoscope 115 during a navigation step as the endoscope 115 approaches an operative region of a patient.

Overview of Patient Introducer Examples

Figure 3A:
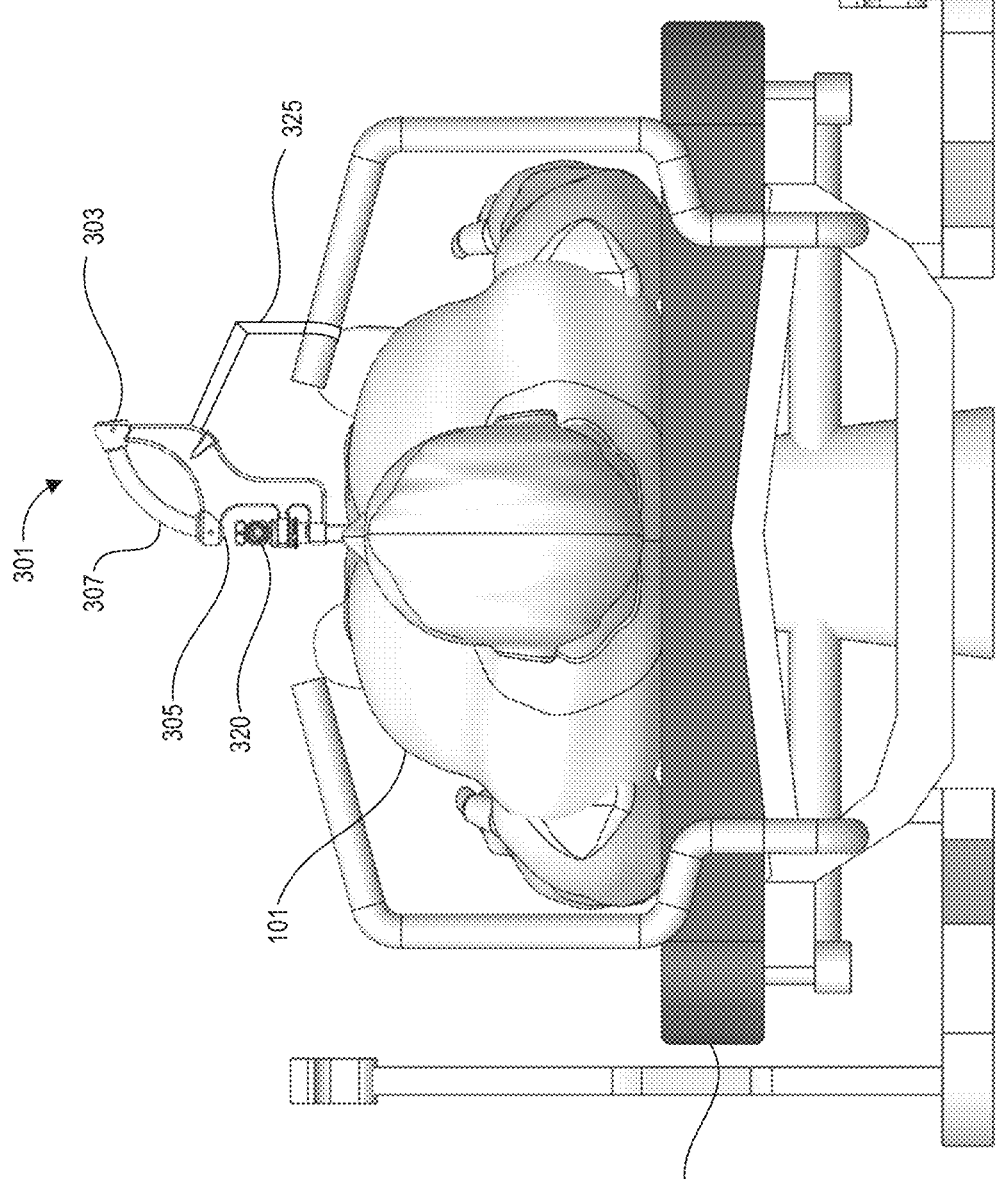
FIG. 3A illustrates an example patient introducer in accordance with one or more aspects of this disclosure.

FIG. 3A illustrates an example patient introducer 301 in accordance with one or more aspects of this disclosure. In the example of FIG. 3A, the patient introducer 301 is attached to a patient 101 via a port 320. In the embodiment illustrated in FIG. 3A, the port 320 may be a surgical tube. The patient introducer 301 may be secured to the platform 102 via a patient introducer holder 325. The patient introducer holder 325 may secure the position of the patient introducer 301 with respect to the platform 102 and may also reduce the force applied to the patient 101 by the patient introducer 301 by supporting at least a portion of the weight of the patient introducer 301. Although the patient introducer holder 325 is illustrated as being on the same side of the platform 102 as the patient introducer 301, in some embodiments, the patient introducer holder 325 may be located on the opposing side of the platform 102, or any other suitable location, such as the head of the platform 102 or from another platform suspended above the patient. During certain procedures, placement of the patient introducer holder 325 on the opposite side of the platform 102 with respect to the patient introducer 301 may be desirable since this placement may introduce fewer restrictions on the motion of the robotic arms 175. For example, the robotic arms 175 may be restricted from moving to the space occupied by the patient introducer holder 325 when the patient introducer holder 325 is located as illustrated in FIG. 3A. However, the described and illustrated placements of the patient introducer holder 325 are merely exemplary and the patient introducer holder 325 may be placed at any location(s) in which the patient introducer 301 is at least partially supported by the patient introducer holder 325.

The patient introducer 301 may include a proximal end 303 and a distal end 305, as well as an introducer tube 307 therebetween. The proximal end 303 of the patient introducer 301 forms a first opening (also referred to as an orifice) which may be configured to receive a surgical tool 115 (e.g., an endoscopic tool) and the distal end 305 of the patient introducer 301 forms a second opening which may be configured to guide the surgical tool 115 into the port 320. The introducer tube 307 connects the proximal and distal ends 303, 305 of the patient introducer 301 and guides the surgical tool 115 from the proximal end 303 to the distal end 305 of the patient introducer 301. A lumen of the introducer tube 307 can provide a channel extending through the introducer that connects the first and second openings at opposing ends of the introducer tube to provide a pathway that guides one or more medical tools therethrough. The introducer tube 307 can be configured with any of a variety of shapes or cross sections to provide guiding channel therethrough. For example, the introducer tube 307 or the channel may have a round, square, rectangular, or other cross-sectional shape. The introducer tube 307 or the channel may extend along a straight path or a curved path containing one or more bends.

Between the first opening formed at the proximal end 303 of the patient introducer 301 and the second opening formed at the distal end 305 of the patient introducer 301, the introducer tube 307 may have a defined curvature to guide the distal end of the surgical tool 115 along the introducer tube 307 as the surgical tool 115 is advanced from the proximal end 303 to the distal end 305 of the introducer tube 307. For example, a curved lumen extending through the introducer tube 307 can provide a curved channel that guides and redirects the surgical tool along a curved pathway through the patient introducer 301. This may enable the surgical robotic system 110 to manipulate the surgical tool 115 from a position that is not in direct axial alignment with the port 320, thereby allowing for greater flexibility in the placement of the cart of the surgical robotic system 110 within the room. That is, without the curvature of the introducer tube 307, the robotic arms may be required to be substantially aligned with a major axis of the surgical tool above the patient's head. Further, the curvature of the introducer tube 307 may allow the robotic arms 175 of the surgical robotic system 110 to be substantially horizontally aligned with the patient introducer 301, which may facilitate manual movement of the robotic arm 175 if needed.

Figure 3B:
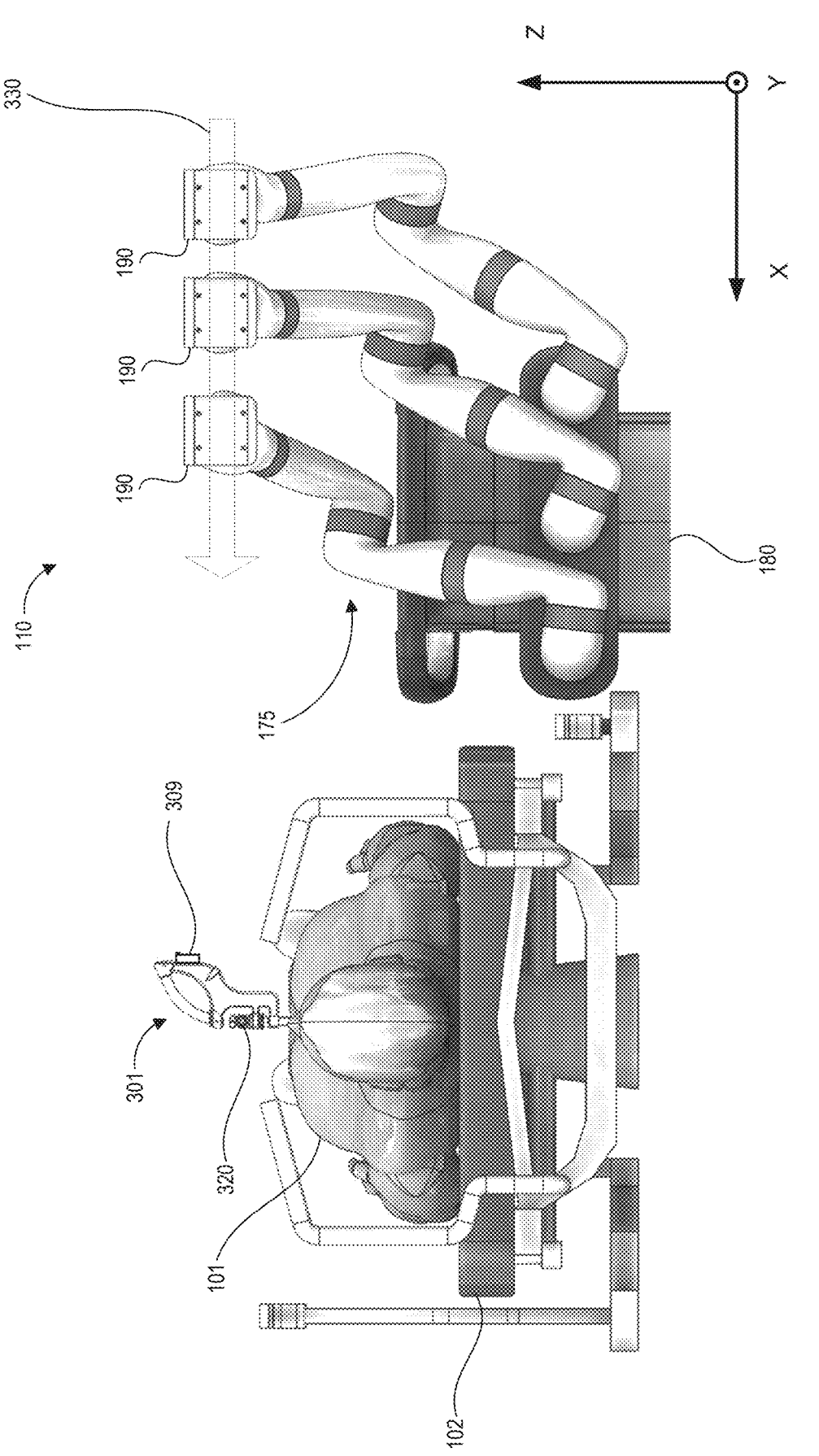
FIG. 3B illustrates an embodiment of a system and approach to aligning a surgical robotic system cart with a patient introducer in accordance with aspects of this disclosure.

FIG. 3B illustrates an example embodiment of a system and approach to aligning a system or robot base 180, configured as a surgical robotic system cart, with a patient introducer 301 in accordance with aspects of this disclosure. In this embodiment, the patient introducer 301 further includes an alignment member 309 which may aid in alignment of the robotic system cart and/or a robotic arm 175 with the patient introducer 301. The robotic arms 175 of the surgical robotic system 110 may be configured to align to form a virtual rail 330, conceptually illustrated in FIG. 3B by a dashed arrow. As used herein, a "virtual rail" refers to a computer-generated axis that can be used to relate components of a robotic system with each other or with one or more objects in an operating environment. For example, any two or more robotic arms may use positional awareness or sensing capabilities of the robotic system to define an axis in three-dimensional space and align or constrain physical components of the robotic system with each other along the axis, without necessarily having a physical rail or physical guide feature between such components. The positional awareness may be determined, for example, by a processor of the system based on an articulation state of each arm. Each joint of a robotic arm may be encoded (e.g., with a rotary encoder that determines a position of motors in the robotic arm) so that a position of the distal end of the robotic arm can be determined based on the encoded articulation state of each joint. The virtual rail 330 may have a major axis which may be aligned with the first opening in the proximal end 303 of the patient introducer 301 (see FIG. 3A). Additionally, the virtual rail may define a volume in space in which the manipulator assemblies (e.g., the IDMs 190) are configured to be arranged during manipulation of the surgical tool 115 (e.g., during a surgical procedure). Accordingly, alignment of the virtual rail 330 defined by the IDMs 190 with the patient introducer 301 may improve operational control of the surgical tool 115 during a surgical procedure as defined above.

As will be discussed in connection with the various embodiments thereof, the alignment member 309 provides a number of advantages to the patient introducer 301 over a patient introducer that does not include an alignment member 309. For example, the physical alignment of an IDM 190 with the alignment member 309 may facilitate increased accuracy and expedited alignment as compared to other alignment techniques. Proper alignment of the patient introducer 301 with the IDM 190 via the use of the alignment member 309 may prevent issues that may arise during the surgical procedure, such as, for example, elevated levels of friction or situations requiring manual assistance during the surgical procedure. Another possible result of misalignment that can be prevented is that the stroke length of the robotic arms 175 may be limited, which can limit the ability of the surgical robotic system 110 in controlling the distal end of the surgical tool 115 throughout the desired range of motion. Without the full range of motion, the surgical tool 115 may be prevented from accessing a target location within a luminal network 140, which may require realignment of the surgical robotic system cart with the patient introducer 301 prior to performing the surgical procedure again.

Furthermore, as mentioned above, the alignment member 309 of the patient introducer 301 may be configured to aid in the alignment of components of the surgical robotic system 110 with the patient introducer 301. In at least one embodiment, the alignment member 309 may be configured to physically contact one of the IDMs 190 and/or may include markings (also referred to as markers) for which complementary markings may be formed on at least one IDM 190 to facilitate the alignment.

Alignment of the IDM 190 with the patient introducer 301, via the use of the alignment member 309 or via any other appropriate alignment technique, may be geometrically defined by the six degrees of freedom of movement for a body within three-dimensional space. That is, if the patient introducer 301 is considered to be a fixed point in space, the alignment of the IDM 190 with the patient introducer 301 can be specified by providing values for the six degrees of freedom of movement of the IDM 190 with respect to the patient introducer 301. These degrees of freedom may include the positions (e.g., forward/backward (the X-axis), left/right (the Y-axis), up/down (the Z-axis) as illustrated in FIG. 3B) and/or the orientation (e.g., pitch (rotation around the Y-axis), yaw (rotation around the Z-axis), and roll (rotation around the X-axis)) of the IDM 190. Although the positional axes (X-axis, Y-axis, and Z-axis) may be defined, located, and/or oriented in various different manners, this disclosure will refer to these axes as illustrated in FIG. 3B throughout the disclosure. Aspects of the present disclosure relate to methods and techniques for placing the IDM 190 into an alignment position/orientation with respect to the patient introducer 301 to align the IDM 190 with the patient introducer 301. The surgical robotic system 110 may record the spatial position and/or orientation of the IDM 190 during alignment so that the surgical robotic system 110 is aware of the spatial position and/or orientation of the patient introducer 301 during a surgical procedure.

Alignment of the IDM 190 with the patient introducer 301 may also be defined by the alignment of one or more axes of the IDM 190 with one or more axes of the patient introducer 301. For example, the patient introducer 301 may define an axis (which may be referred to as a receive axis herein) along which the patient introducer 301 is configured to receive the surgical tool 115. Similarly, the IDM 190 may have an axis defined by the virtual rail 330 (discussed above). In certain embodiments, alignment of the IDM 190 with the patient introducer 301 may be defined when the receive axis of the patient introducer 301 is substantially aligned with the virtual rail 330 of the IDM 190.

Figure 4A:
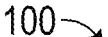
FIG. 4A illustrates an example operating environment including an example surgical robotic system in accordance with aspects of this disclosure.

FIG. 4A illustrates another example of the patient introducer 301 in accordance with one or more aspects of this disclosure. In the example of FIG. 4A, the patient introducer 301 is mounted to a robotic arm 175. Like the patient introducer holder 325 described above with respect to FIGS. 3A-3B, the robotic arm 175 can provide a mechanism to secure the position of the patient introducer 301 with respect to the platform 102. The robotic arm 175 may also reduce the force applied to the patient 101 by supporting at least a portion of the weight of the patient introducer 301.

According to some embodiments, mounting the patient introducer 301 to the robotic arm 175 can provide other benefits associated with particular characteristics or capabilities of a robotic arm as compared to other mounting structures or introducer holders. For example, articulation of the robotic arm 175 can be used to position the patient introducer 301 in the desired location, using automatic, teleoperated, or manual control (e.g., admittance control) to articulate the robotic arm. Such positioning techniques can be useful to flexibly position the patient introducer 301 in three-dimensional space, and upon positioning the introducer in the desired location, joints of the robotic arm 175 can be locked to hold the introducer in the desired location thereafter. In some embodiments, joints of the robotic arm 175 can be locked upon deactivation of an admittance control mode, such as in response to release of an admittance control button. Using articulation of the robotic arm 175 to position the patient introducer 301 can reduce a set up time, improve an ease of set up, improve a positioning accuracy, and/or improve a positioning precision of the patient introducer as compared to other mounting or positioning techniques. Alternatively, or in combination, mounting the patient introducer 301 to one of the robotic arms 175 can facilitate alignment or positioning between the introducer and the medical tool that is introduced therethrough, by allowing another one of the robotic arms 175 to support the medical tool, and by allowing the robotic system to use position sensing capabilities between robotic arms to align the tool and the introducer with each other. Alternatively, or in combination, mounting the patient introducer to a robotic arm can allow the robotic arm to dynamically make intraoperative adjustments to the position or orientation of the patient introducer. Such capabilities may be useful to, for example, reposition the patient introducer during a procedure in case the introducer it is deflected out of a desired position during a procedure (e.g., due to an accidental collision). Alternatively, or in combination, the robotic arm 175 may be provided with a higher degree of stiffness than other mounting structures, thus enhancing a stability of the patient introducer to hold the introducer in the desired position during a procedure in case of accidental collisions that might otherwise deflect the patient introducer out of position.

Figure 4B:
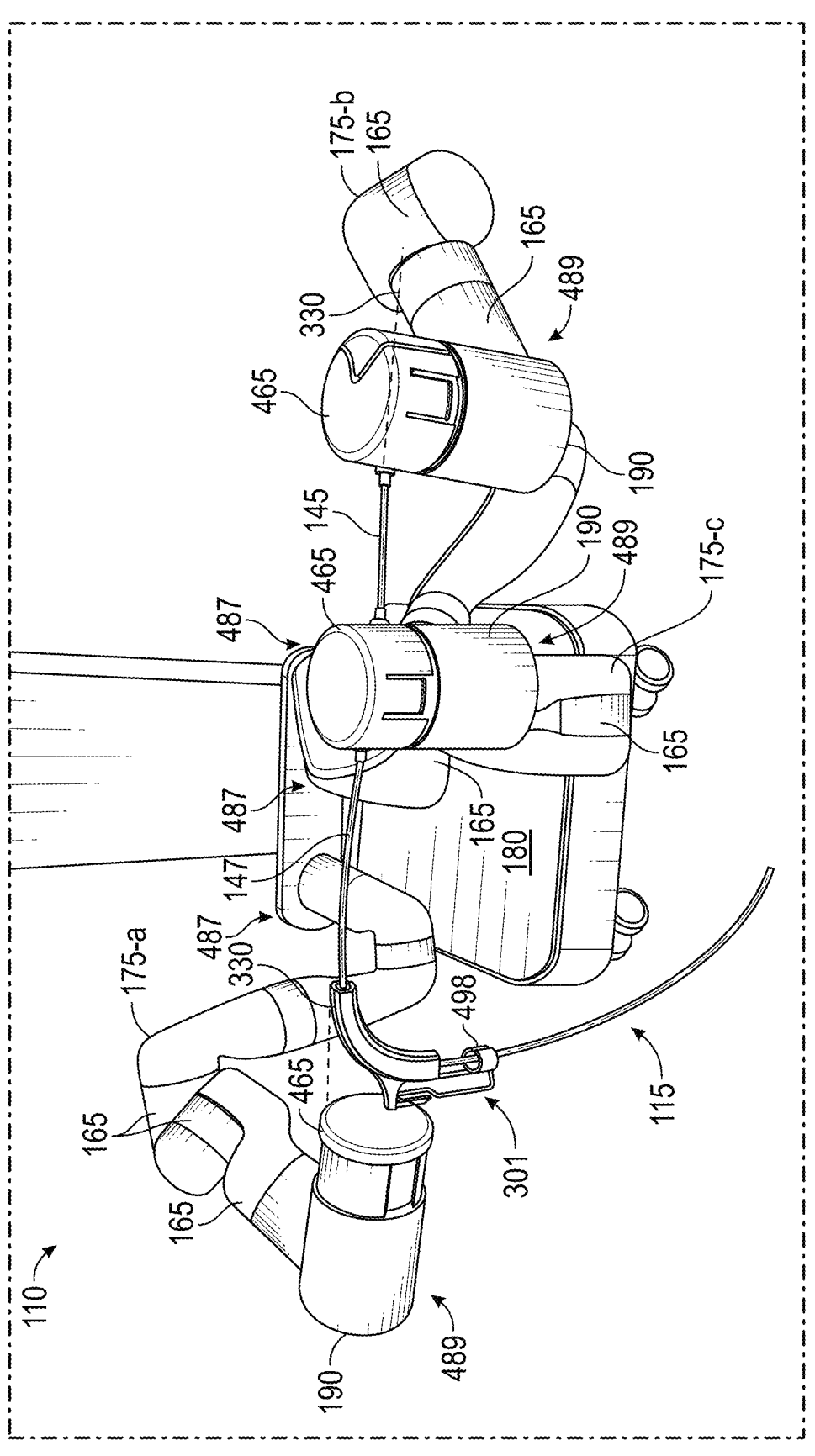
FIGS. 4B-4C illustrate an example surgical robotic system including an example patient introducer mounted to a robotic arm in accordance with aspects of this disclosure.
Figure 4C:
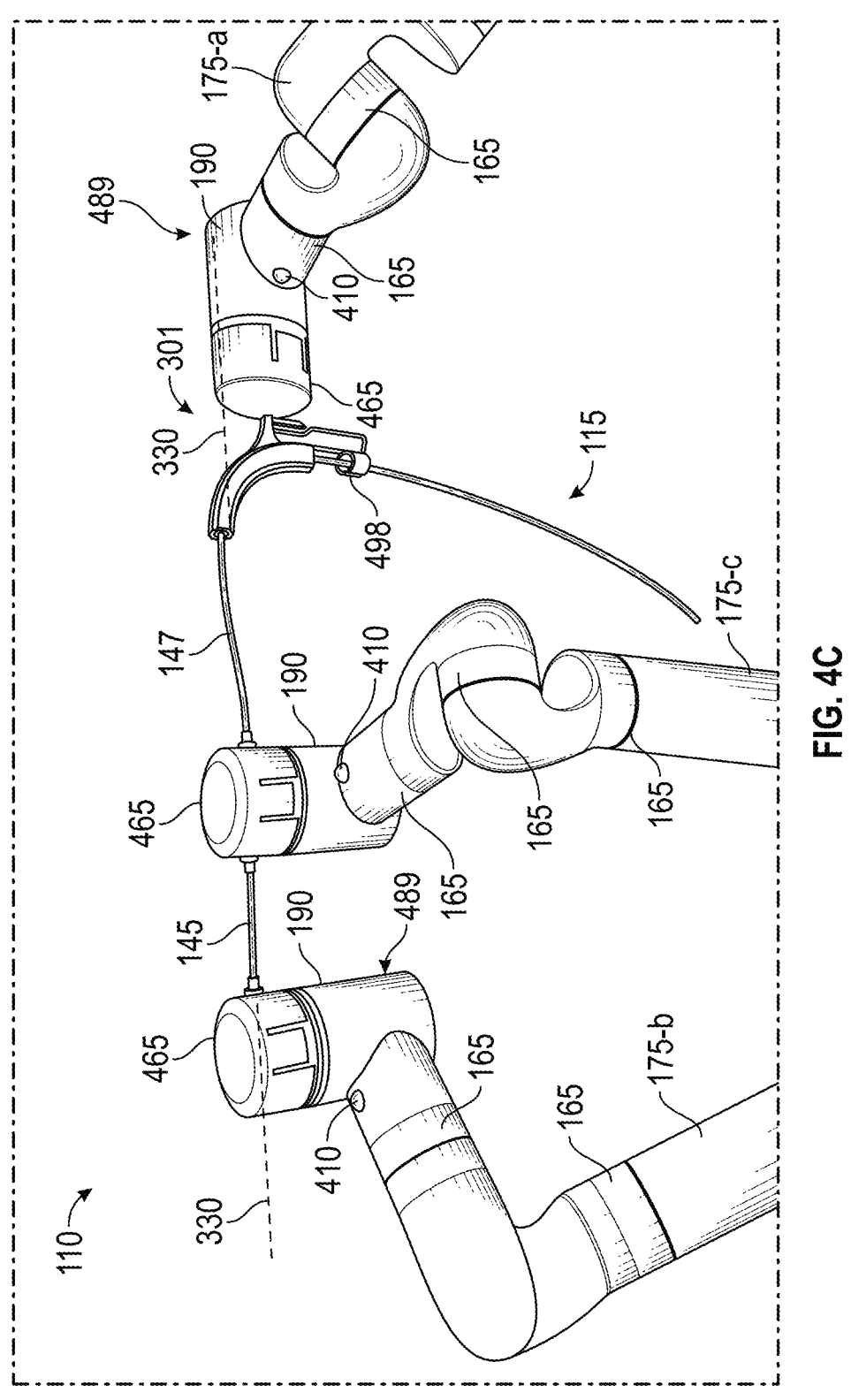

FIGS. 4B-4C are three-dimensional views of the patient introducer 301 in the context of the robotic system 110, in accordance with one or more aspects of this disclosure. FIGS. 4B-4C show an example of an arrangement in which multiple robotic arms 175 are used to support the patient introducer 301 and a medical tool 115 inserted through the patient introducer. FIG. 4B is a front view of the robotic system 110 showing an arrangement of three robotic arms 175, including a first robotic arm 175-*a*, a second robotic arm 175-*b*, and a third robotic arm 175-*c*, attached to robot base 180. FIG. 4C is a rear view showing the arrangement of the three robotic arms.

As seen for example in FIG. 4B, each of the robotic arms 175 can have a proximal end 487 attached to the robot base 180 and a distal end 489 attached to a device manipulated by the corresponding robotic arm. In various embodiments, any medical device to be positioned or manipulated by a robotic arm can be mounted to the distal end 489 of the robotic arm. Examples of medical devices or medical tools include a patient introducer, an endoscope, a camera, a catheter, and a drug or implant delivery device. In the example shown, the patient introducer 301 is mounted to and attached to the distal end 489 of a first robotic arm 175-*a*, and an endoscope 115 is mounted to and attached to the distal ends 489 of each of a second robotic arm 175-*b* and a third robotic arm 175-*c*. The robotic system 110 can be configured to hold the patient introducer 301 in a desired position using the first robotic arm 175-*a*, and drive a flexible medical tool through the patient introducer 301 and into the patient using one or more of the second or third robotic arms 175-*b* or 175-*c*.

In some embodiments, the robotic system 110 can be configured to align the flexible medical tool with an opening of the patient introducer 301 using a virtual rail 330 formed between the first robotic arm 175-*a* and at least one of the second or third robotic arms 175-*b* or 175-*c*. The virtual rail 330 is shown in FIGS. 4B and 4C by a dashed line. The virtual rail 330 can provide a computer-generated linear axis between robotic arms holding the medical tool 115 and the introducer 301, along which axis the robotic system 110 maintains an alignment between the medical tool 115 and the introducer 301. By mounting the patient introducer 301 to one of the robotic arms used to form the virtual rail 330, the virtual rail 330 may more easily align the medical tool 115 with the receive axis of the patient introducer 301 due to intrinsic positional awareness capabilities of both the medical tool 115 and the patient introducer 301 provided by the robotic arms attached thereto. For example, such a mounting of the patient introducer 301 on the robotic arm 175-*a* can avoid a need for the virtual rail 330 to determine a position of external elements that are not part of the robotic system when attempting to align the medical tool 115 therewith, resulting in easier, more accurate, or more automated alignment capabilities. Alternatively, or in combination, the robotic system 110 can use an alignment member 309 (FIG. 3B) or any other appropriate alignment technique to align the medical tool to an introducer attached to the robotic arm 175.

In various embodiments, the patient introducer 301 can be configured to guide the medical tool 115 in any desired direction, based on a fixed shape of the patient introducer 301 or an orientation of the robotic arm 175 holding the introducer. For example as seen in FIGS. 4B-4C, the system can be configured so that at least a portion of the channel of the patient introducer 301 extends in a direction different than a direction of the virtual rail 330 between the robotic arms 175, which allows the patient introducer 301 to redirect the endoscope 115 to enter an opening on the patient at the different direction. Accordingly, the robotic arm(s) holding the endoscope or other tool being introduced into the patient need not be arranged at an excessively high height to introduce the endoscope at the proper angle into a vertically oriented port on the patient. In the illustrated example, a distal portion of the channel of the introducer 301 extends substantially perpendicular to the virtual rail 330 and perpendicular to a proximal portion of the channel defining a receive axis into which the endoscope 115 enters the introducer, causing the endoscope 115 to exit the distal end of the patient introducer 301 at a direction substantially parallel to the virtual rail. Although a particular angle and orientation is shown, it is contemplated that other angles and orientations can be used in various embodiments.

As seen in FIGS. 4B-4C, the robotic system 110 can be configured to drive the endoscope 115 through the patient introducer 301 with second and third robotic arms 175-*b* and 175-*c*, while the first robotic arm 175-*a* holds the patient introducer 301 in place to guide components of the endoscope into the patient (patient not visible in FIGS. 4B-4C). In some embodiments, the second and third robotic arms 175-*b* and 175-*c* can each be configured to drive distinct components of the endoscope 115. For example, the second robotic arm 175-*b* can be configured to drive the inner leader portion 145 through the outer sheath portion 147, through the patient introducer 301, and into the patient. In some embodiments, the second robotic arm 175-*b* can be configured to drive the inner leader portion 145 independently of the outer sheath portion 147. In some embodiments, the third robotic arm 175-*c* can be configured to drive the outer sheath portion 147 through the patient introducer 301 and into the patient, independently of the inner leader portion 145. Although this example uses a pair of robotic arms to drive the endoscope 115, and each arm can be capable of selectively driving a respective portion of the endoscope, it is contemplated that any one or more arms may be used to drive any one or more flexible elongate medical tools through a patient introducer attached to a robotic arm in various embodiments.

In the example shown, the multiple robotic arms 175 are shown arranged in a row. For example, as seen in FIG. 4B, the proximal ends 487 of the three robotic arms 175 can each be coupled to the robot base 180 along a linear row. The first robotic arm 175-*a*, which is attached to the patient introducer 301, is arranged at an end of the row. Such an arrangement can facilitate positioning of the patient introducer 301 over the patient's mouth or aligned with an opening at on the patient's body, while the remaining robotic arms may be free to manipulate the endoscope 115 without crossing over each other, colliding with the patient, or colliding with the robotic arm 175-*a* holding the patient introducer 301. Such an arrangement can be advantageous for particular procedures. However, it is contemplated that various other arrangements of the robotic arms 175 can be utilized, including arrangements in which the multiple robotic arms are not all arranged in a row or arrangements in which the robotic arm 175-*a* having the patient introducer 301 attached thereto is arranged at any other location within a row.

FIG. 4C illustrates examples of admittance controls such as admittance buttons 410 that can be included on the robotic arms 175 (e.g., at the distal ends 489 thereof) to facilitate positioning of the instruments using an admittance control mode. As seen in FIG. 4C, each of the robotic arms 175 can include a corresponding admittance button 410 to permit the corresponding robotic arm to be manually manipulated by a user to a desired position. Operation of the admittance controls, via depression of the admittance button 410 for example, can allow the instruments at the end of each robotic arm to be positioned in three-dimensional space manually. In some embodiments, appropriate assistance or operation from motors of the robotic arm can facilitate articulation of the various arm segments 170 about the joints 165 as the robotic arms are moved manually. Admittance control of the robotic arms can be useful to, for example, position the patient introducer 301 in alignment with an opening on a patient or to a position in which it can be attached to a port on the patient. In the example shown, the patient introducer 301 includes a clip 498, which is configured to releasably attach to the port 320 (FIG. 3A-3B) to ensure proper alignment between the exit opening of the patient introducer and the entrance opening of the port 320 on the patient's body, once the patient introducer 301 is moved into position.

As seen in FIGS. 4B-4C, each of the second and third robotic arms 175-*b* and 175-*c* can operate their attached medical tool components via their respective IDMs 190. Each of the IDMs 190 can be included in or otherwise coupled to the distal end 489 of the corresponding robotic arm 175. Each of the medical tools can be attached to an IDM 190 of a corresponding robotic arm 175 via an instrument base 465, which can be releasably attachable to the robotic arm 175 via an attachment interface. The attachment interface between each tool and robotic arm may be modular attachment interface that permits any of a variety of other medical instruments to be attached in the robotic system 110 as appropriate, allowing the robotic system to be flexibly adapted to a variety of different procedures. The attachment interface can include corresponding and complementary parts on each of the IDM 190 and instrument base 465, with such corresponding and complementary parts being configured to mate together to releasably attach and secure the tool to the robotic arm. For example, each of the IDM 190 and instrument base 465 can include a latch mechanism, clip, magnetic connector, or any other appropriate releasable securement mechanism that forms the attachment interface for mechanically attaching the instruments. The attachment interface can also form an operative connection between the medical tool and the robotic arm (e.g., operative connection to the IDM 190), allowing the robotic arm to actuate components of the medical tool. In some embodiments where an operative connection is formed between the robotic arm and the attached tool, the instrument base 465 can further include an input shaft, gear, track, or other drive transfer mechanisms configured to mate with a drive shaft, gear, sprocket, or other drive mechanisms on the IDM when secured via the attachment interface.

Example Implementations of Robot-Mounted Patient Introducer

Examples of a patient introducer 301 are shown in FIGS. 5A-5D. In each of FIGS. 5A-5D, the patient introducer 301 can be releasably mountable to a robotic arm. FIGS. 5A-5D are various views illustrating examples of the patient introducer 301 in a detached configuration.

As seen in the figures, the patient introducer 301 can include an instrument base 465, and an introducer tube 307 coupled to the instrument base 465. The introducer tube 307 can be a guide member that permits a medical tool (e.g., endoscope 115) to be inserted therethrough, such that the introducer tube 307 guides the medical tool from an opening at one end to an opening at an opposing end thereof. For example, the introducer tube 307 can include a proximal end 303 having a first opening 304 configured to accept insertion of the medical tool, such that the first opening 304 at the proximal end 303 acts as an entrance opening for the tool. The introducer tube 307 can further include a distal end 305 opposite the proximal end 303, with the distal end 305 having a second opening 306 configured to deliver the inserted medical tool, such that the second opening 306 at the distal end 305 acts as an exit opening for the tool inserted into the entrance opening.

A lumen 595 of the introducer tube 307 can extend from the proximal end 303 to the distal end 305 and connect the first and second openings at the proximal and distal ends. The lumen 595 can provide a channel extending through the introducer that guides the medical tool through the introducer to its intended destination. According to some embodiments, for example as seen in FIGS. 5A-5D, the lumen 595 can be configured as a curved lumen, and the channel extending through the introducer can be a curved channel so as to redirect the inserted medical tool to exit the patient introducer at a different direction from which the medical tool enters the patient introducer. In this example, the curved lumen is configured with an approximately 90 degree bend to redirect the guided medical tool to exit at a direction substantially perpendicular to a direction at which the medical tool enters the introducer. When mounted to a robotic arm (for example as seen in FIGS. 4B-4C), a proximal portion of the channel and lumen 595 connected to the entrance opening can extend substantially parallel to the virtual rail 330, while a distal portion of the channel and lumen 595 connected to the exit opening is angled relative to the proximal portion and relative to the virtual rail so that the distal portion extends in a direction substantially perpendicular to the virtual rail 330.

Figure 5A:
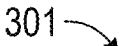
FIGS. 5A-5D each illustrate an example patient introducer in accordance with aspects of this disclosure.
Figure 5A:
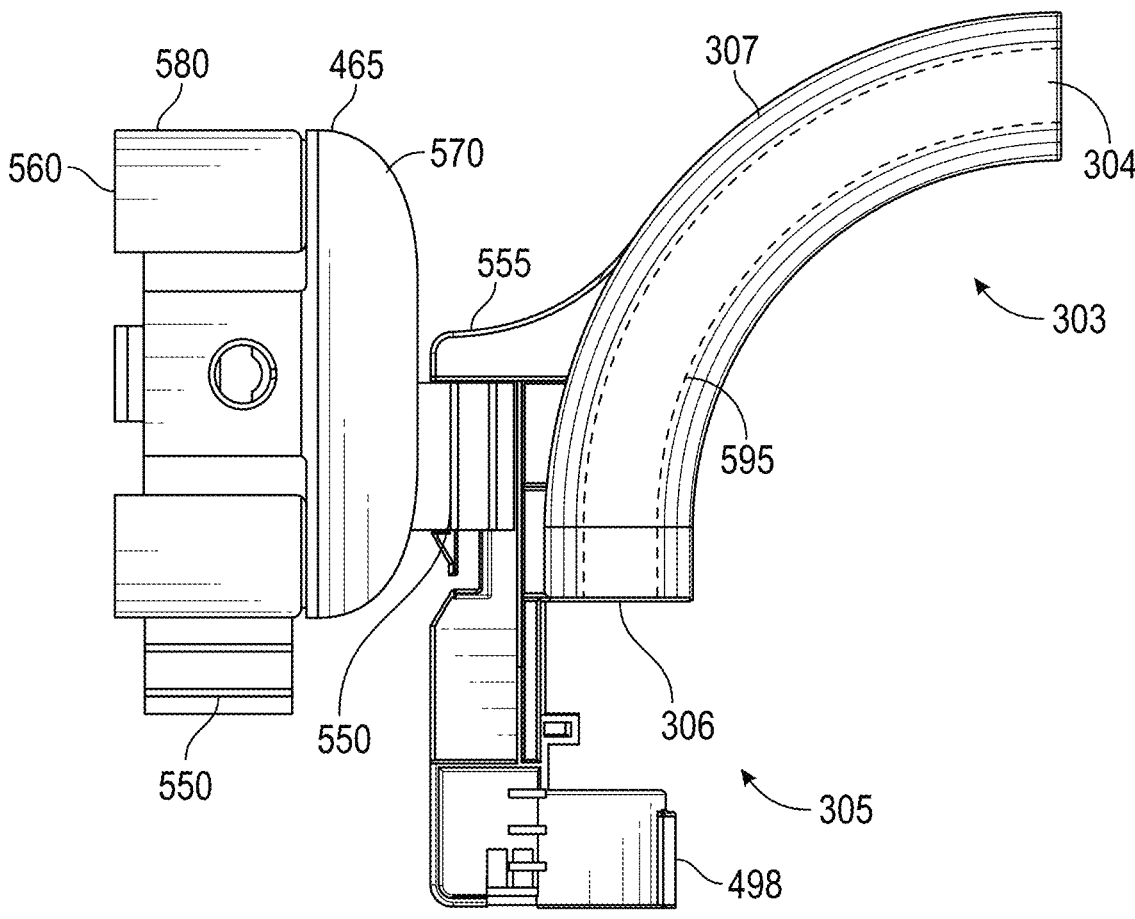

According to some embodiments, for example as seen in FIG. 5A, the patient introducer 301 can include a clip 498 aligned with the exit opening at the distal end 305 of the patient introducer 301. The clip 498 can be configured to attach to a port (e.g., an endrotracheal tube or other surgical tube) installed on the patient, so that the exit opening at the distal end of the introducer tube is aligned with an entrance opening of the port when the clip 498 is attached to the port.

The clip 498 shown in FIG. 5A is configured as a round, substantially C-shaped member that can snap onto the exterior surface of a tubular member of the port on the patient's body. The opening of the C-shaped member is aligned with the second opening 306 at the distal end of the introducer channel to facilitate alignment between the exit opening of the introducer tube and entrance opening of the port when the C-shaped member is clipped to the port. Although the clip 498 is shown as a C-shaped clip, it is contemplated that other types of clips or attachment members can be included with the patient introducer 301 to secure the introducer to the port.

Components of the patient introducer 301 can be integrally formed of a unitary construction or otherwise permanently fixed together. Alternatively, any two or more of the components of the patient introducer 301 can be detachable or movable relative to each other. For example, any two or more of the instrument base 465, the introducer tube 307, or the clip 498 can be provided as separable parts that are detachable and re-attachable to each other in different configurations. Such a detachable configuration can facilitate greater adaptability of the patient introducer for various needs. Additionally or alternatively, such a detachable configuration can facilitate greater efficiency of use based on different components having different useful lives, allowing one component to be replaced without a need for replacing the entire tool.

Figure 5B:
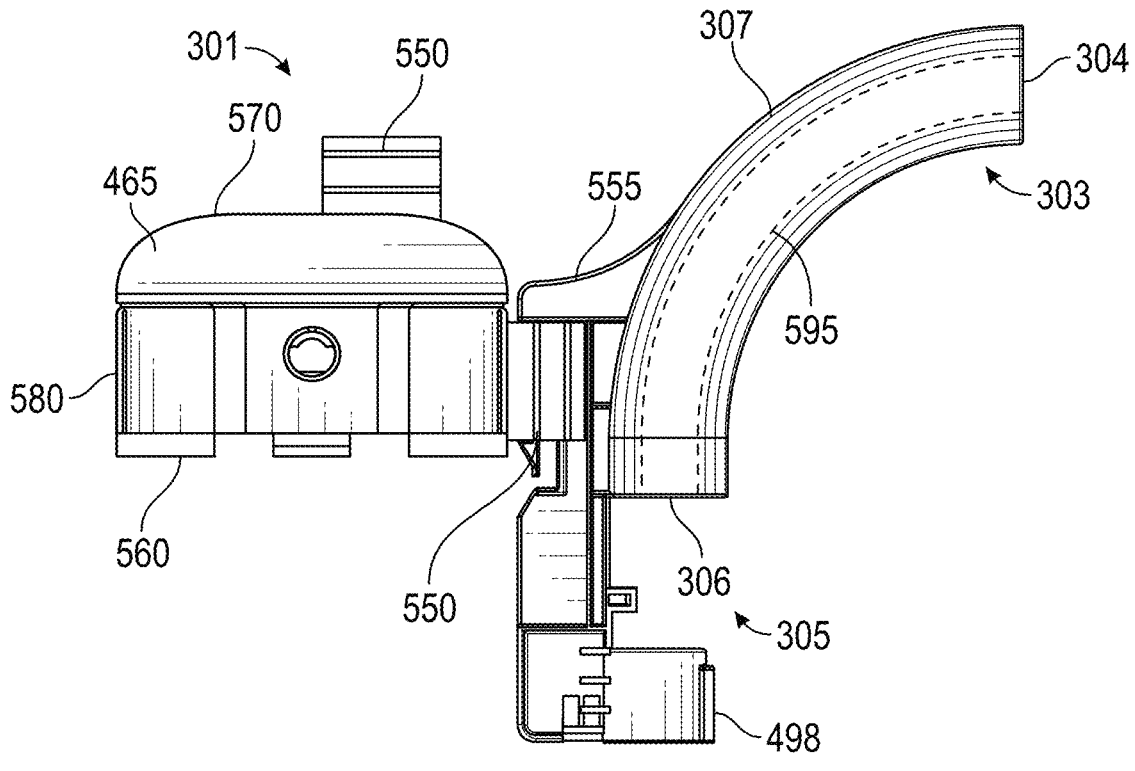
Figure 5C:
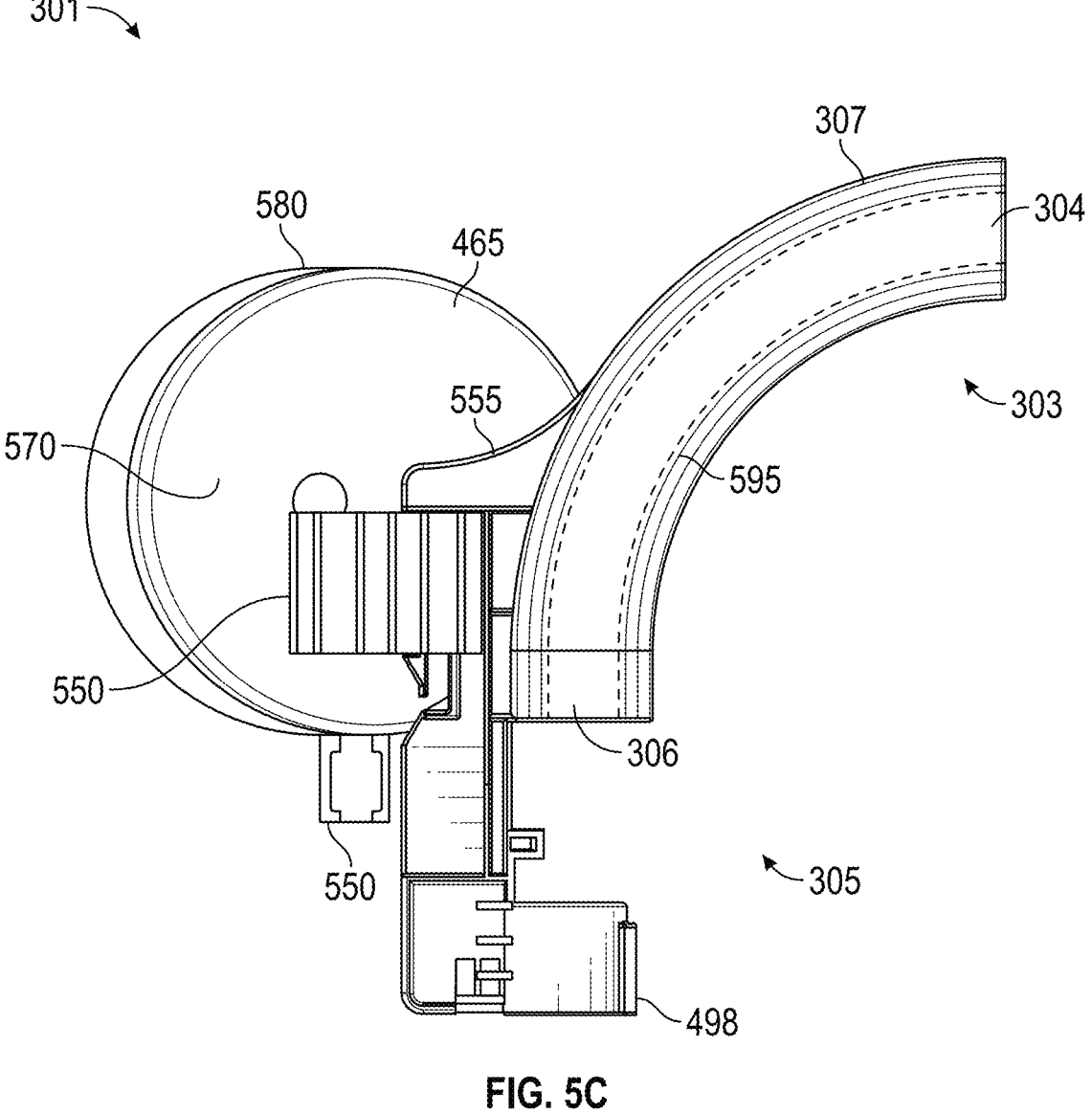

As seen in FIGS. 5A-5C, the patient introducer 301 can include one or more mounts 550. Each of the mounts 550 can be a mounting structure on the instrument base 465 that permits attachment of a detachable component. In the configuration shown in FIGS. 5A-5C, the mounts 550 are configured to attach to the introducer tube 307, which is configured as a detachable part separate from the instrument base 465. The mounts 550 are configured to hold the introducer tube 307 in a desired position and orientation with respect to the instrument base 465. The introducer tube 307 has a complementary engagement member 555 that is configured to mate with one of the mounts 550 on the instrument base to secure the introducer tube 307 in position on the mount. In the mounting mechanism shown, each of the mounts 550 has a slot configured to receive a corresponding tab of the engagement member 555. It is contemplated that, in various embodiments, any of a variety of other mount and engagement member structures can be suitably used for attaching the instrument base 465 and introducer tube 307.

In the example shown, multiple mounts 550 are disposed on different locations along the instrument base 465 to permit the introducer tube 307 to be attached to any one of the mounts 550, based on the desired position of the introducer tube 307 and its corresponding introducer channel relative to the robotic arm in any particular instance of use. In various embodiments, any appropriate number of mounts 550 can be included on the instrument base 465, with each of the mounts differing in at least one of position or orientation with respect to the instrument base 465 to permit the introducer tube 307 to be positioned in different positions or orientations across different instances of use. A greater number of discrete mounts can provide a greater number of possible positions or orientations of the introducer tube 307 for greater adaptability to different procedures or patient positions. Although multiple mounts 550 are shown, in various embodiments, the instrument base 465 can include any appropriate number of mounts. For example, the instrument base 465 can have one mount, two mounts, three mounts, four mounts, five mounts, six mounts, eight mounts, ten mounts, or any suitable number of mounts thereon.

FIGS. 5A-5C are various views illustrating the introducer tube 307 coupled to the instrument base 465 in different positions or orientations. Such positioning flexibility can be useful to, for example, optimize the arrangement of robotic arms and the patient introducer based on considerations such as collision avoidance between the robotic arms, positioning with respect to body parts of the patient for various procedures, or physician preference.

FIG. 5A is a side view illustrating a top-facing configuration for the patient introducer 301. The instrument base 465 can include a first side 560, a second side 570, and a third side 580. The first side 560 can be an attachment side that is configured to mate with a robotic arm. The second side 570 can be an opposite side opposite to the attachment side. The third side 580 can be a lateral side adjoining the first side 560 and second side 570. In FIG. 5A, the introducer tube 307 is attached to the second side 570 so as to position the introducer tube 307 opposite the attachment side. The introducer tube 307 is attached via a mount 550 that is configured to hold the introducer tube 307 in a position in which the entrance opening (first opening 304) of the introducer tube 307 faces an opposite direction from the direction that the attachment side faces.

FIG. 5B is a front view illustrating a lateral-facing configuration for the patient introducer 301. In this example configuration, the introducer tube 307 is attached to the third side 580, which is a lateral side adjoining the attachment side and the opposite side. Also, the mount 550 on the lateral side shown in this example is configured to hold the introducer tube 307 on a position in which the entrance opening of the introducer tube 307 faces a lateral direction with respect to the instrument base 465. In the illustrated example, the entrance opening is configured to face a direction substantially parallel to a plane defined by the attachment side.

FIG. 5C is a top view illustrating another lateral-facing configuration for the patient introducer 301. In this example, the introducer tube 307 is positioned on the second side 570, which is opposite the attachment side. However, the mount 550 to which the introducer tube 307 is mounted is configured to hold the introducer tube 307 in a position in which the entrance opening faces a lateral direction with respect to the instrument base 465.

In FIGS. 5A-5C, different poses (e.g., positions or orientations) of the introducer tube 307 are shown by way of example, and the different poses of the introducer tube 307 are achieved by attaching the introducer tube 307 to a different one of multiple mounts 550 included on the instrument base. Alternatively, or in combination, the instrument base can be provided with a movable mount that can move with respect to the instrument base. For example, a movable mount can be configured to translate or rotate along the instrument base 465 to adapt the position or orientation of the introducer tube 307 for various configurations, such as any of the configurations shown in FIGS. 5A-5C. It is also contemplated that a variety of different poses for the introducer tube 307 with respect to the instrument base 465 are possible. In related aspects, the introducer tube 307 may be attached to the instrument base via a movable mount that permits adjustment of at least one of a relative position or orientation between the introducer tube 307 and the instrument base 465. In further related aspects, the mount may be moveably coupled to the base 465 to permit a change in position of a medical device/tool with respect to the base 465.

Figure 5D:

FIG. 5D is a bottom perspective view illustrating an attachment side 560 for patient introducer 301. The attachment side 560 can include an attachment interface that is configured to mate with a corresponding modular attachment interface of a robotic arm. The attachment interface can include a securement mechanism 538 that is configured to secure the instrument base 465 to the robotic arm, e.g., via securely clipping or latching to the corresponding attachment interface on the IDM. In some embodiments, the patient introducer 301 can be a non-actuatable component that is attached to a robotic arm. The robotic arm may have drive shafts configured to drive actuatable components when an actuatable instrument is coupled thereto (drive shafts 606 of a robotic arm can be seen, for example, in FIG. 6B). Accordingly, the attachment interface of the patient introducer 301 can include one or more openings to accommodate components of the driver or other parts of the robotic arm. In the example shown in FIG. 5D, the attachment interface of the patient introducer, on the attachment side 560 of the instrument base 465, includes multiple drive shaft openings 511 configured to respectively accommodate multiple drive shafts of an IDM of the robotic arm when the instrument base 465 is attached thereto. Accordingly, each of the drive shaft openings 511 can be configured to permit a corresponding drive shaft to extend therethrough. As the introducer may be a non-actuatable component, the instrument base 465 of the introducer can be configured to de-couple or isolate the introducer tube 307 from any operative connection to the drive shafts of the robotic arm when in an attached configuration. For example, the instrument base can be a hollow shell that supports the introducer tube 307 or any other component rigidly coupled thereto without necessarily having any moving parts within the hollow shell that mate with any drive shafts of the robotic arm.

As described above, the instrument base 465 can provide an adapter for attachment of an introducer tube 307. However, it is contemplated that instrument base 465 can be used as an adapter for attachment (e.g., rigid or non-actuatable attachment) of any appropriate medical tool desired to be mounted to a robotic arm. For example, an instrument base 465 configured as described above, with one or more drive shaft openings 538, mounts 550, hollow instrument base, and/or an attachment interface forming non-operative accommodation of drive shaft(s), can be used as an adapter for coupling any tool to the robotic arm in situations where it is desirable to use positioning or mounting capabilities of the robotic arm for the tool without needing to actuate moving parts of the tool. Such an adapter can provide a cost effective and flexible solution for set up for a variety of procedures.

FIG. 5D also shows an example of an alignment member 309 that can be included in the patient introducer 301, in accordance with some embodiments. As further described herein, the alignment member 309 can be utilized to align a medical tool with respect to the patient introducer 301.

Example Implementations of the Alignment Member

Figure 6A:
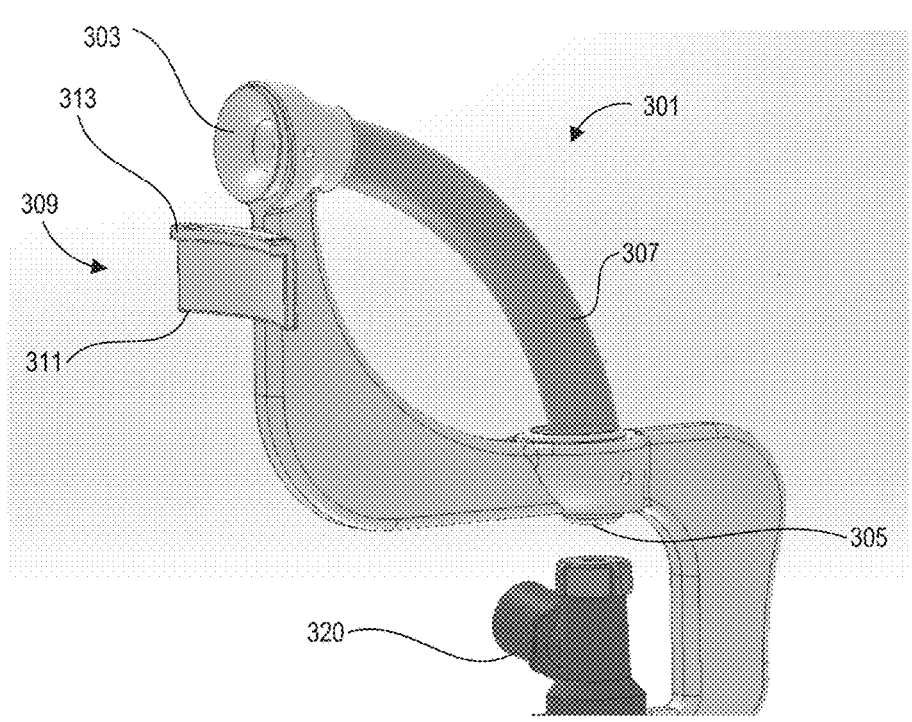
FIGS. 6A and 6B illustrate an embodiment of an alignment member for use during an alignment procedure in accordance with aspects of this disclosure.
Figure 6B:
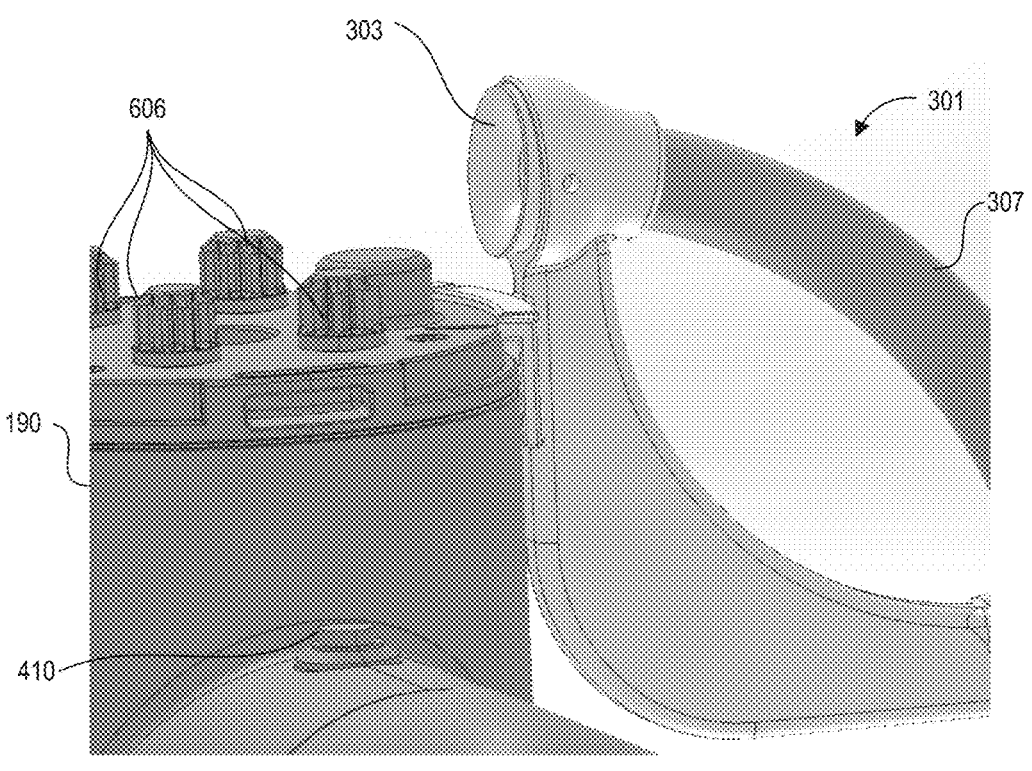

FIGS. 6A-B and 7A-H illustrate different embodiments of the alignment member 309 and IDM 190 in accordance with aspects of this disclosure. FIGS. 6A and 6B respectively illustrate an embodiment of the alignment member 309 on its own and the alignment member 309 in contact with an IDM 190 during an alignment procedure.

Some examples of alignment are described herein with respect to a patient introducer 301 mounted to patient introducer holder 325 (FIGS. 3A-3B). However, it is contemplated that any of the alignment systems or methods described herein may be used in connection with a patient introducer mounted to a robotic arm (e.g., as described above with respect to FIGS. 4A-4C).

With reference to FIGS. 6A and 6B, the patient introducer 301 includes an alignment member 309 attached to the body or supporting structure of the patient introducer 301. The alignment member 309 may be positioned proximal to the proximal end 303 of the introducer tube 307. This location for the alignment member 309 may facilitate alignment of the opening defined in the proximal end 303 with an IDM 190 via physical contact between the alignment member 309 and the IDM 190. However, in other embodiments, the alignment member 309 may be attached to the patient introducer 301 at other locations or may be attached to the patient introducer holder 325. For example, when the distance between the alignment member 309 and the opening defined in the proximal end 303 of the introducer tube 307 is known, the surgical robotic system 110 may be able to accurately calculate the positioning of the IDM 190 with respect to the opening defined by the proximal end 303 of the patient introducer 301 in response to an alignment of the IDM 190 with the alignment member 309.

The alignment member 309 may include physical features, markings and/or other alignment components to aid in alignment with the IDM 190. In one implementation, the alignment member 309 may include a first curved surface 311 and an elongated protrusion 313. The shape defined by the first curved surface 311 and the elongated protrusion 313 may form a complementary shape to an external surface of the IDM 190. As such, the IDM 190 may be at least partially aligned with the alignment member 309 by bringing the IDM 190 into close physical contact with (e.g., interfacing with) the alignment member 309, as shown in FIG. 6B. For example, after an external curved surface of the IDM 190 contacts the first curved surface 311 and an upper surface of the IDM 190 contacts the elongated protrusion 313, the positioning of the IDM 190 in space with respect to the alignment member 309 may be defined by restricting further movement of the IDM 190 past the first curved surface 311 and the elongated protrusion 313. Additionally, as shown in FIG. 6B, the upper surface of the IDM 190 which contacts the elongated protrusion 313 may not be the highest surface defined by the IDM 190, but may be defined by a recess. In other embodiments, the upper surface of the IDM 190 which contacts the elongated protrusion 313 may be defined by a protrusion in the upper surface of the IDM 190 or may be flush with the remainder of the upper surface. Similarly, the external curved surface of the IDM 190 which contacts the first curved surface 311 may be flush with the external surface of the IDM, formed as a recess, or formed as a protrusion. Additional exemplary embodiments will be discussed in detail below.

While the first curved surface 311 of the alignment member 309 remains in contact with the external curved surface of the IDM 190 (e.g., a majority of the first curved surface 311 is in contact or in close contact with the external curved surface), the alignment of the alignment member 309 with the IDM 190 is restricted in four degrees of freedom (e.g., in the X and Y-axes as well as in the pitch and roll orientations). The elongated protrusion 313 may be used to restrict orientation of the alignment member 309 with the IDM 190 in the Z-axis degree of freedom.

The physical contact between the IDM 190 and the alignment member 309 may be sufficient to define the spatial positioning of the IDM 190 with respect to the alignment member 309; however, in some embodiments, the physical contact may not be sufficient for complete rotational alignment therebetween in each of the rotational degrees of freedom (e.g., in the yaw orientation). For example, in the FIG. 6B embodiment, the IDM 190 may be free to rotate around the Z-axis while maintaining contact with the alignment member 309. Accordingly, in some embodiments, the alignment member 309 and/or the IDM 190 may further comprise alignment markings to define the rotational alignment of the IDM 190 with the alignment member 309. FIG. 6B also illustrates examples of drive shafts 606 that can be included on the IDM 190 of the robotic arm 175 to actuate instruments attached thereto.

Figure 7B:
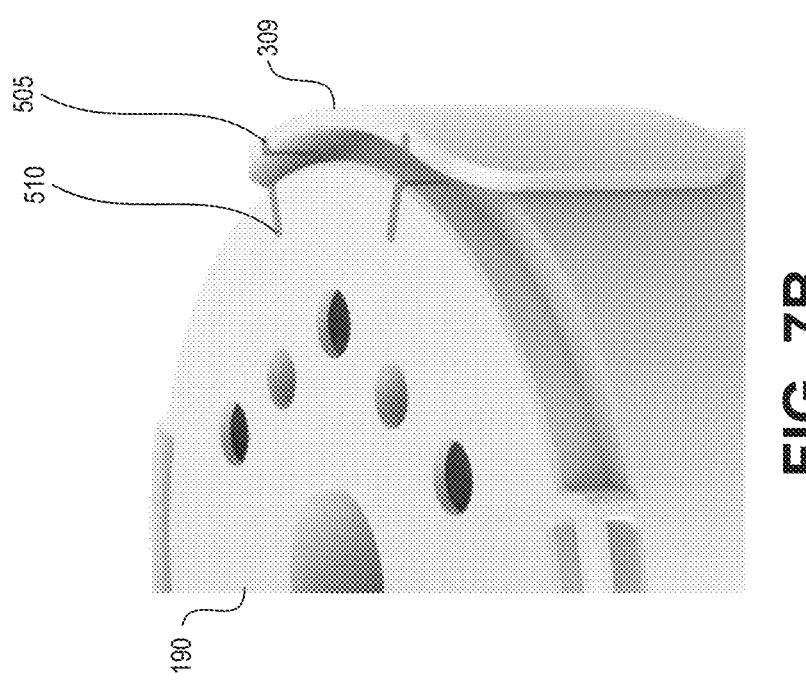
Figure 7A:
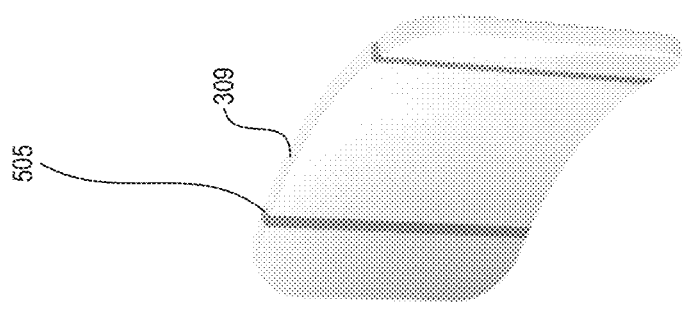
Figure 7A:
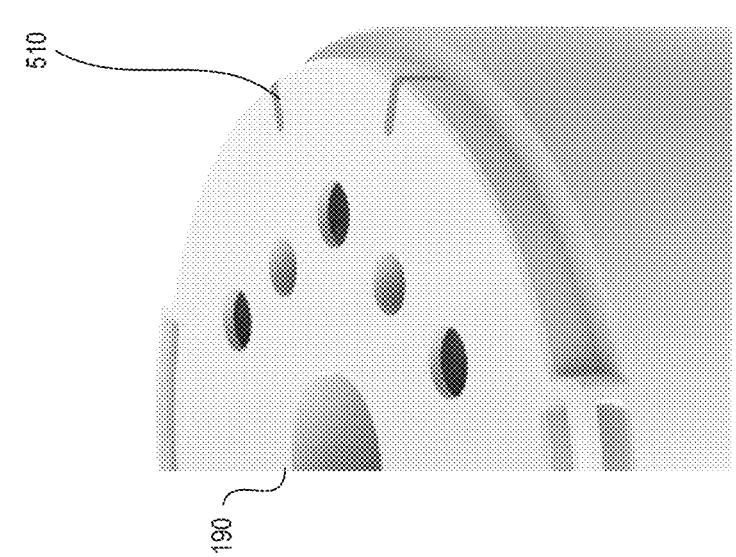

FIGS. 7A-7H illustrate a number of embodiments of alignment markings which may be used to aid in rotational alignment of a manipulator assembly (e.g., the IDM 190) with the alignment member 309. In the embodiment of FIGS. 7A and 7B, the alignment member 309 includes a first set of alignment markings 505 and the IDM 190 includes a second set of alignment markings 510 corresponding to the first set of alignment markings 505. After the alignment member 309 has been brought into contact with the IDM 190 (as in FIG. 7B), the IDM 190 and the alignment member 309 can be rotationally aligned, with respect to rotation about the Z-axis (e.g., the yaw of the IDM 190), by aligning the first and second sets of alignment markings 505 and 510. In the embodiment of FIGS. 7A and 7B, the first and second sets of alignment markings 505 and 510 may be formed as bands. The alignment bands may be embodied by various different shapes, sizes, dimensions, tolerances, etc. in order to aid in the yaw orientation alignment of the IDM 190 with the alignment member 309. Certain embodiments of the bands are illustrated in FIGS. 7A, 7B, and 7E-H; however, the design of the bands is not limited thereto and the bands may have any shape, size, dimension, tolerance, etc. for alignment in the yaw orientation.

Figure 7D:
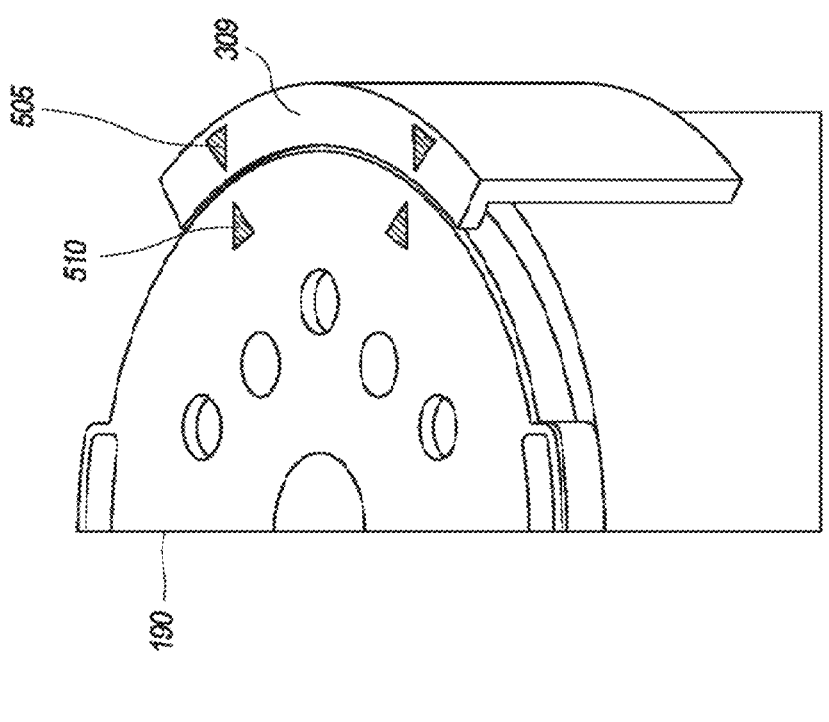
Figure 7D:
Figure 7C:
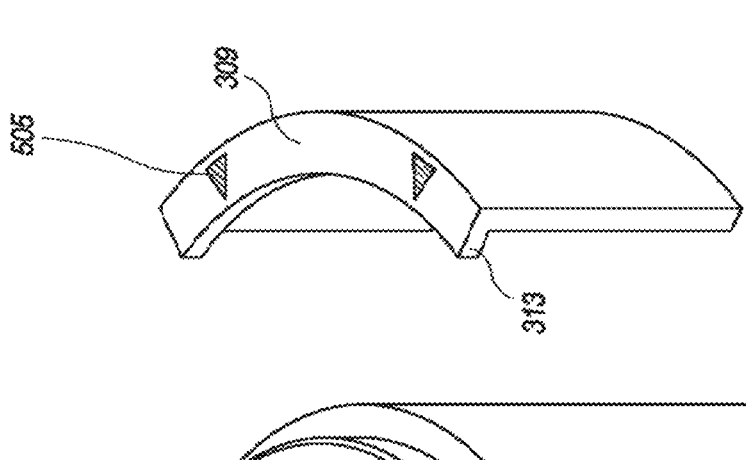
Figure 7C:
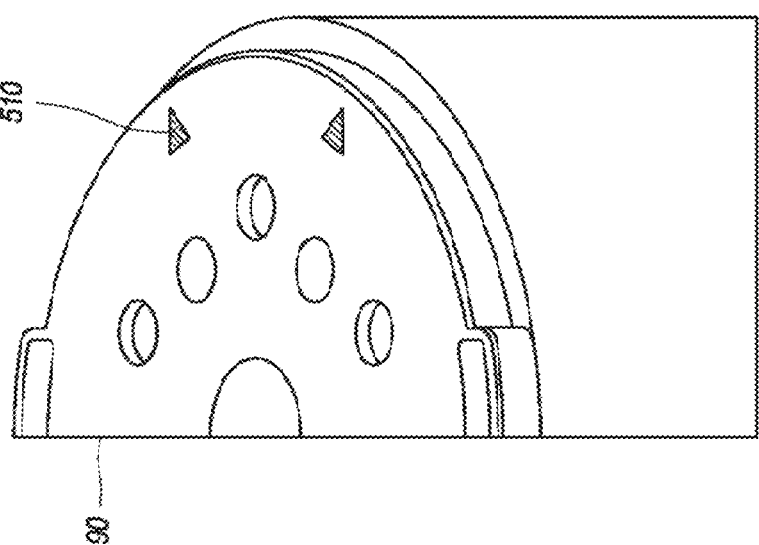

In the embodiment of FIGS. 7C and 7D, the first and second sets of alignment markings 505 and 510 may be formed as opposing triangles. In this embodiment, the points of the triangles may be matched up to confirm that rotational alignment between the IDM 190 and the alignment member 309 is complete. As shown in FIGS. 7C and 7D, the alignment markings 505 may be formed on the elongated protrusion 313.

Another embodiment, as illustrated in FIGS. 7E and 7F, includes a single first alignment marking 505 and a single second alignment marking 510. In this embodiment, the first and second alignment markings 505 and 510 form wider bands than in the embodiment of FIGS. 7A and 7B. Here, rotational alignment between the IDM 190 and the alignment member 309 may be achieved when the ends of the bands are substantially aligned with each other. In yet another embodiment, as shown in FIGS. 7G and 7H, the first alignment markings 505 may be wider than the second alignment markings 510. In this embodiment, the IDM 190 may be rotationally aligned with the alignment member 309 when the second alignment markings 510 are within the widths defined by the bands of the first alignment markings. Here, the difference in widths between the first and second alignment markings 505 and 510 may correspond to a tolerance range for rotational alignment with respect to rotation around the Z-axis. The tolerance range defined by the widths of the alignment markings 505 and 510 may ensure that the surgical robotic system is able to fully manipulate the surgical tool at any position defined within the tolerance range. Additionally, in other embodiments, the second alignment markings 510 formed on the IDM 190 may be wider than the first alignment markings 505. Although the tolerance range has been discussed in connection with the embodiment where the tolerance range is defined by the widths of the alignment markings 505 on the alignment member 309, the indication of the tolerance range may vary and differ across difference embodiments and markings. For example, the tolerance range may be defined by the first alignment markings 505 on the alignment member 309, by the second alignment markings 510 on the IDM 190, and/or by a combination thereof etc. Furthermore, the indication of the tolerance range may be located on the patient introducer 301, the IDM 190, a sterile adaptor, etc.

The first alignment markings 505 and the second alignment markings 510 may also be positioned on the alignment member 309 and the IDM 190 at locations which enable a user of the robotic surgical system to visually confirm rotational alignment from a number of different vantage points. For example, as shown in FIG. 6B, the IDM 190 may have a number of components which protrude from the upper surface of the IDM 190. These protrusions, and/or other objects such as the patient introducer itself, may block the view of one or more of the first and second alignment markings 505 and 510 depending on where the user is standing. Accordingly, the first and second alignment markings 505 and 510 may be placed at different locations on the alignment member 309 and the IDM 190 such that at least one of each of the first and second alignment markings 505 and 510 is viewable by the user when viewed from one of a plurality of vantage points. This may enable the user to visually confirm the rotational alignment of the IDM 190 and the alignment member 309 without requiring the user to move in order to see the first and second alignment markings 505 and 510.

Additionally, when the manipulator assembly includes an additional component attached to the IDM 190, such as a sterile adaptor, a third set of alignment markings (not illustrated) may be formed on the additional component so that the additional component can be aligned with the alignment member. The third markings may be formed on the additional component in a manner similar to the second markings 510 illustrated in FIGS. 7A-7H. In these embodiments, the sterile adaptor may include at least a portion with a surface that complements the shape of the alignment member 309. The sterile adaptor may be an adaptor configured to be physically attached to the IDM 190 for surgical procedures which require the interface between the IDM 190 and the robotic arm 175 to be sterile. In certain embodiments, the sterile adaptor may have an exterior surface and/or surgical tool interface that is substantially the same as or similar to that of the interface between the IDM 190 and the surgical tool 115.

Additional Alignment Techniques

In certain aspects of this disclosure, additional alignment techniques may be employed in place of or in addition to the physical alignment embodiments discussed in connection with FIGS. 6A-B and 7A-H. These techniques may assist in the manual or automatic alignment of the IDM 190 with the patient introducer 301.

In one example, a radio-frequency identification (RFID) reader and RFID tag may be used to aid in alignment. The patient introducer 301 may include an RFID tag positioned on the alignment member 309 or another location on the patient introducer 301. The IDM 190 may include an RFID reader configured to read a wireless signal transmitted from the RFID tag. In other embodiments, the positions of the RFID tag and RFID reader may be exchanged.

The RFID tag may be a passive device which collects energy emitted from the RFID reader and may transmit an RFID signal using the power collected from the RFID reader. By detecting the signal transmitted from the RFID tag, the RFID reader may be able to determine the position of the RFID reader with respect to the RFID tag. Additionally, as the RFID reader moves closer to the RFID tag, the signal detected by the RFID reader may become stronger. Accordingly, when the RFID reader finds a maximum (or peak) in the strength of the signal received from the RFID tag, the RFID reader may be able to infer that the RFID tag is at a closest possible position to the RFID reader. The strength of the received RFID signal may be displayed to a user, for example, via display modules 202, in order to aid in the manual alignment of the IDM 190 with the patient introducer 301. Alternatively, the RFID signal may be used as an input by a processor of the surgical robotic system for the automatic alignment of the IDM 190 with the patient introducer 301.

In another example, the surgical robotic system 110 may include a laser tracking system to aid in alignment. For example, the IDM 190 may include a laser emitter (also referred to simply as a laser) and a laser light sensor, while a laser reflector is positioned on the patient introducer 301 (e.g., on the alignment member 309). The laser, laser reflector, and laser light sensor may be positioned such that laser light is reflected onto the sensor when the IDM 190 is properly aligned with the patient introducer 301. As such, the positioning of the laser and laser light sensor with respect to the laser reflector enable the surgical robotic system 110 to determine that the IDM 190 has been aligned with the patient introducer 301.

In an alternative embodiment, the IDM 190 includes at least one laser and the patient introducer 301, or the alignment member 309, includes at least one alignment marking corresponding to the laser. The user of the surgical robotic system 110 may then determine that the IDM 190 is aligned with the patient introducer 301 by visually confirming that the laser light falls on the at least one alignment marking. In these embodiments, the placement of the laser, laser reflector, laser light sensor, and the at least one marking may be exchanged between the IDM 190 and the patient introducer 301. In certain embodiments, there may be at least three lasers and three markings/sensors in order to ensure that the alignment between the IDM 190 and patient introducer 301 is defined in all degrees of freedom. In certain embodiments, there may be at least one laser and at least one marking/sensor in order to ensure that the alignment between the IDM 190 and patient introducer 301 is defined in all degrees of freedom.

In another example, the alignment member 309 may include a light-emitting diode (LED) configured to emit light based on a positioning of the LED relative to a photodiode placed on the IDM 190. For example, the photodiode place on the IDM 190 may be able to sense light emitted from the LED in order to determine the alignment of the IDM 190 with respect to the alignment member 309. Additionally, in certain embodiments, the alignment member 309 may include a plurality of LEDs respectively corresponding to a plurality of photodiodes positioned on the IDM 190. When the photodiodes detect light received from the respective LEDs, the IDM 190 may be able to determine that the IDM 190 has been aligned with the alignment member. Further, the LEDs may have different colors while the photodiodes may have corresponding color filters. Thus, only light from a corresponding one of the LEDs may be detected by the photodiodes.

In another example, the alignment of the IDM 190 with the patient introducer 301 may include the use of acoustic reflection. For example, the IDM 190 may include an acoustic emitter and an acoustic sensor, while the patient introducer 301 and/or alignment member 309 includes an acoustic reflector. The IDM 190 may then be positioned based on the signal detected by the acoustic sensor, where a maximum value of the measured signal is indicative of the IDM 190 being aligned with the patient introducer 301.

In another example, a magnetic field sensor may be placed on the IDM 190 with a magnet placed on the patient introducer 301 and/or alignment member 309. The signal measured by the magnetic sensor may be used to determine the positional alignment of the IDM 190 with the patient introducer. The placement of these elements may be exchanged between the IDM 190 and patient introducer 301.

In one implementation, the alignment of the IDM 190 with the patient introducer 301 may further involve the use of an EM generator and an EM sensor or EM sensors. For example, the manipulator assembly may include an EM sensor and an EM generator may be arranged on or adjacent to the platform 102. The surgical robotic system 110 may use the signal detected by the EM sensor to determine the position of the IDM 190 with respect to the EM generator.

In yet further embodiments, the physical shape of the alignment member 309 and the IDM 190 may be altered from the embodiments discussed in connection with FIGS. 6A-B and 7A-H. For example, the alignment of three points on the patient introducer 301 with three corresponding points on the IDM 190 may be sufficient to define alignment therebetween. Thus, in one example, the patient introducer 301 may include three elongated protrusions while the IDM 190 may include three markings corresponding thereto. When the elongated protrusions are in contact with the corresponding markings on the IDM 190, the patient introducer 301 may be aligned with the IDM 190. Alternatively, the elongated protrusions may be formed on the IDM 190, with the markings on the patient introducer 301, or each of the IDM 190 and patient introducer may include three protrusions configured to meet in space with the corresponding protrusions on the opposing element.

Although a number of examples of different sensors which may be used to aid a user in aligning the IDM 190 with the patient introducer 301 and/or for automatic alignment of the IDM 190 with the patient introducer 301 performed by the surgical robotic system 110, other types of sensor may also be used in addition to or in place of the sensors described herein. For example, alignment may be performed using any other sensor modality, including but not limited to vision shape matching using optical sensor(s) (e.g., camera(s)), ultrasound sensor(s), accelerometer(s), capacitive coupling sensor(s), etc.

Another method for physical alignment between the patient introducer 301 and the IDM 190 may be the use of a protrusion and hollow cavity. Thus, when the protrusion is inserted into the hollow cavity, the patient introducer 301 and IDM 190 may be aligned. Since a simple cylindrical protrusion and hollow cavity may not define rotational alignment along the major axis of the protrusion, the protrusion/hollow cavity may be keyed such that only one rotational alignment therebetween will allow the protrusion to be inserted into the cavity.

Example Methods

Example methods of using a medical robotic system are described in connection with flowcharts shown in FIGS. 8-13, and described with reference to the systems and devices shown in FIGS. 1A-7G. For example, some methods for aligning a surgical robotic system cart with a patient introducer are described in connection with FIGS. 8-12. An example method of using a surgical robotic system with a robotic-arm-mounted patient introducer is described in connection with FIG. 13.

Figure 8:
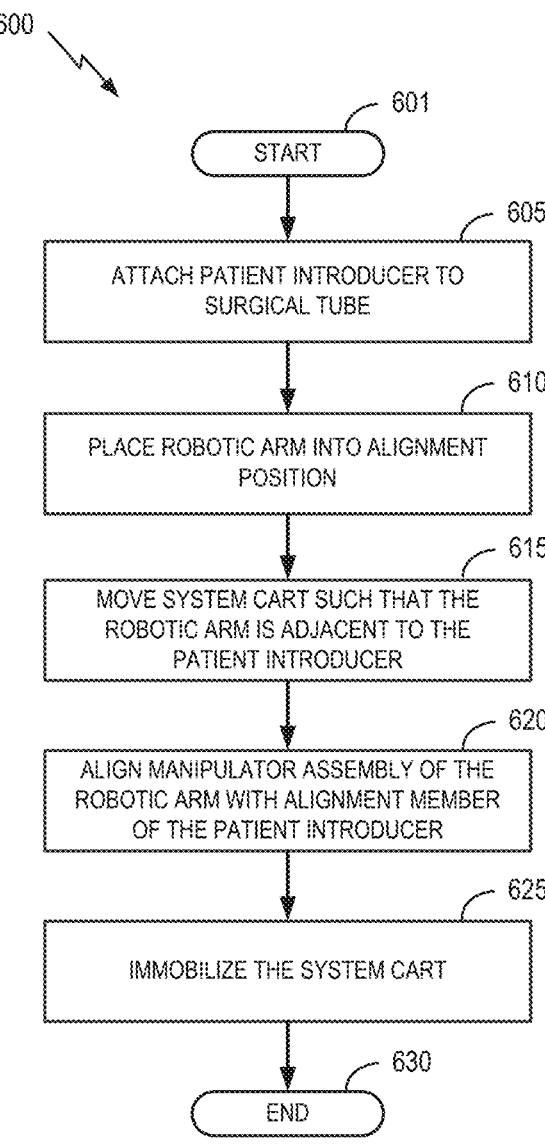
FIG. 8 provides a flowchart illustrating an example methodology of aligning of a surgical robotic system cart with a patient introducer in accordance with aspects of this disclosure.

FIG. 8 provides an overview of the alignment of the system cart with the patient introducer, in accordance with some embodiments. Aspects of each of the methods disclosed hereinafter, e.g., methods 600-1100, can be implemented by a human operator manually manipulating the IDM 190 or other components of a surgical robotic system, the surgical robotic system itself (such as system 110 described above) mechanically manipulating the IDM 190 as directed by a human operator or autonomously, or a combination thereof.

As seen in FIG. 8, method 600 begins at block 601. At block 605, the patient introducer 301 is attached to a port 320. The port 320 may be been previously placed in a patient 101 by medical staff. At block 610, the robotic arm 175 is placed into an alignment pose. This may be performed automatically by the surgical robotic system 110 in response to an input command from the user, or the user may manually guide the robotic arm 175 into the alignment pose. When guided by the user, the surgical robotic system may provide feedback to the user indicative of when the robotic arm 175 is in or within a threshold distance of the alignment position.

At block 615, the user may optionally move the robot base 180 (e.g., in embodiments that utilize a system cart as the robot base) such that the robotic arm 175 is adjacent to the patient introducer 301. This step may be considered a coarse alignment of the system cart with the patient introducer. Since the robotic arms 175 have a limited range of motion, if the system cart is not placed sufficiently close to the patient introducer prior to alignment, the robotic arm 175 may not be able to reach the patient introducer for alignment. Block 620 involves aligning (spatially and/or rotationally) the manipulator assembly (e.g., the IDM 190) of the robotic arm 175 with an alignment member 309 of the patient introducer 301. This step may be done manually by the user, automatically by the surgical robotic system 110, or by a combination of manual and automatic procedures. The surgical robotic system 110 may store the position of the IDM 190 (e.g., an alignment position) in response to the IDM 190 being aligned with the patient introducer 301. The storing of the alignment position of the IDM 190 may be performing in response to the surgical robotic system 110 receiving a confirmation from the user that the IDM 190 is aligned with the patient introducer 301.

In certain embodiments, the patient introducer 301 may be moved into alignment with the IDM 190. For example, the platform 102 supporting the patient 101 may be movable (e.g., having lockable/unlockable wheels) and/or adjustable within the operating environment 100 to facilitate alignment with the IDM 190. Accordingly, the platform 102 may be moved into position such that the patient introducer 301 is aligned with the IDM 190. In some embodiments, alignment of the IDM 190 with the patient introducer 301 may involve moving both the IDM 190 and the patient introducer 301. Once the manipulator assembly 190 has been aligned with the patient introducer 301, at block 625, the user may optionally immobilize the surgical robotic system cart. Alternatively, if the surgical robotic system cart includes automated brakes and/or an actuator for moving the cart, the surgical robotic system 110 may automatically immobilize the system cart. In some embodiments, such as where the robotic arm 175 is not positioned on a system cart (e.g., when the robotic arm 175 is positioned on the table), blocks 615 and 625 may not be performed. The method 600 ends at block 630.

Figure 9:
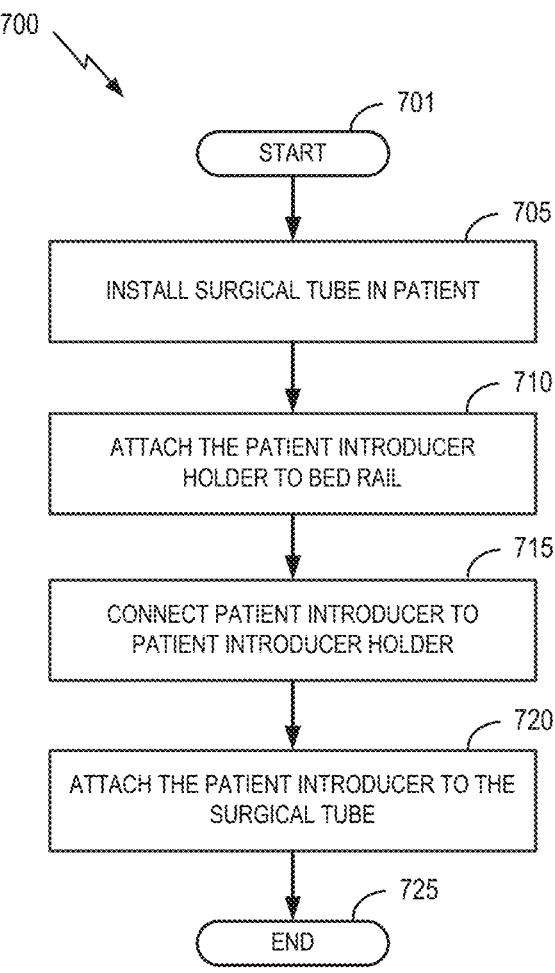
FIGS. 9-12 provide flowcharts illustrating examples of further aspects of the alignment methodology of FIG. 8.

FIG. 9 provides a flowchart illustrating a method 700 providing additional aspects related to block 605 of FIG. 8. The method 700 begins at block 701. At block 705, a port 320 is installed into the patient. Block 705 may be performed by medical staff in preparing for a surgical procedure to be performed by/using the surgical robotic system 110. At block 710, the medical staff may attach and/or secure the patient introducer holder 325 to a bed rail or other secure portion of the platform 102. Examples of the secure portion of platform 102 to which the patient introducer holder 325 may be attached include: a bed frame, a support column, a pad placed underneath the patient 101, etc. This may secure the patient introducer 301, reducing the chance of the patient introducer 301 shifting or otherwise moving out of position during alignment or the surgical procedure. At block 715, the medical staff connects the patient introducer 301 to a patient introducer holder 325. In other embodiments, at block 715, the step of attaching the patient introducer 301 to the patient introducer holder 325 may be replaced with the medical staff connecting the patient introducer 301 to a robotic arm 175. In such embodiments, the step of attaching the patient introducer holder 325 to a secure portion of the platform 102 at block 710 may be omitted.

At block 720, the medical staff attaches the patient introducer 301 to the port 320. This step may be performed simultaneously with block 715, for example, the final position of the secured patient introducer holder 325 or the position of the robotic arm 175 holding the patient introducer 301 may not be set until after the patient introducer 301 has been connected to the port 320. In other embodiments, the patient introducer 301 may be aligned with the port 320 without being directly connected thereto. For example, the patient introducer 301 may be secured or otherwise maintained in position adjacent to and in alignment with the port 320. The method 700 ends at block 725.

Figure 10:
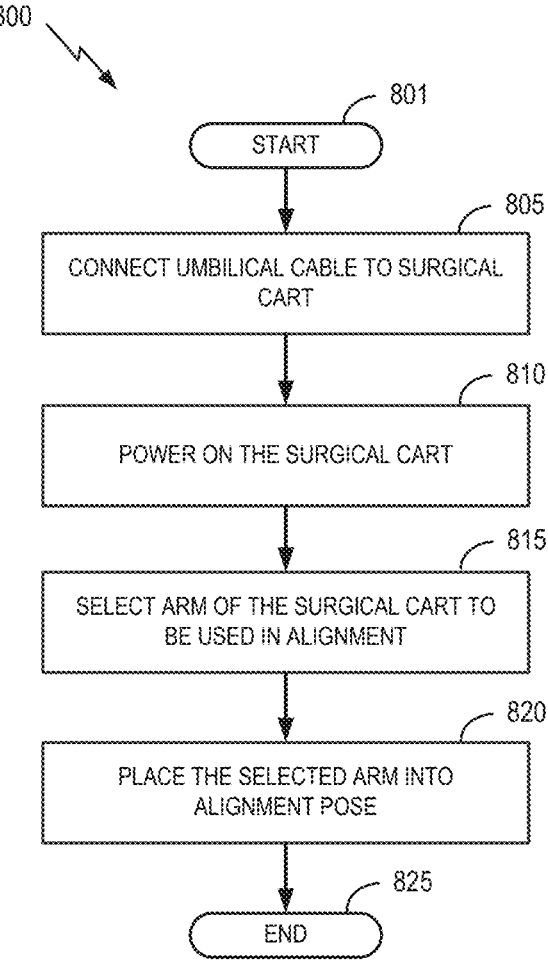

FIG. 10 is a flowchart illustrating a method 800 providing additional aspects related to block 610 of FIG. 8. The method 800 begins at block 801. At block 805, the user connects an umbilical cable to the surgical robotic system cart. The umbilical cable may provide communication and/or power to the surgical robotic system cart. At block 810, the user powers on the robotic surgical system cart. At block 815, the user may select one of a plurality of robotic arms 175 of the robotic surgical system cart to be used in alignment with the patient introducer 301. The selected robotic arm 175 may be the closest arm 175 to the patient 101 and/or bed 102. At block 820, the user places the selected robotic arm 175 into the alignment pose. In other embodiments, the user may input a command to the surgical robotic system 110 to have the surgical robotic system 110 automatically position the robotic arm 175 into the alignment pose. The method 800 ends at block 825.

Figure 11:
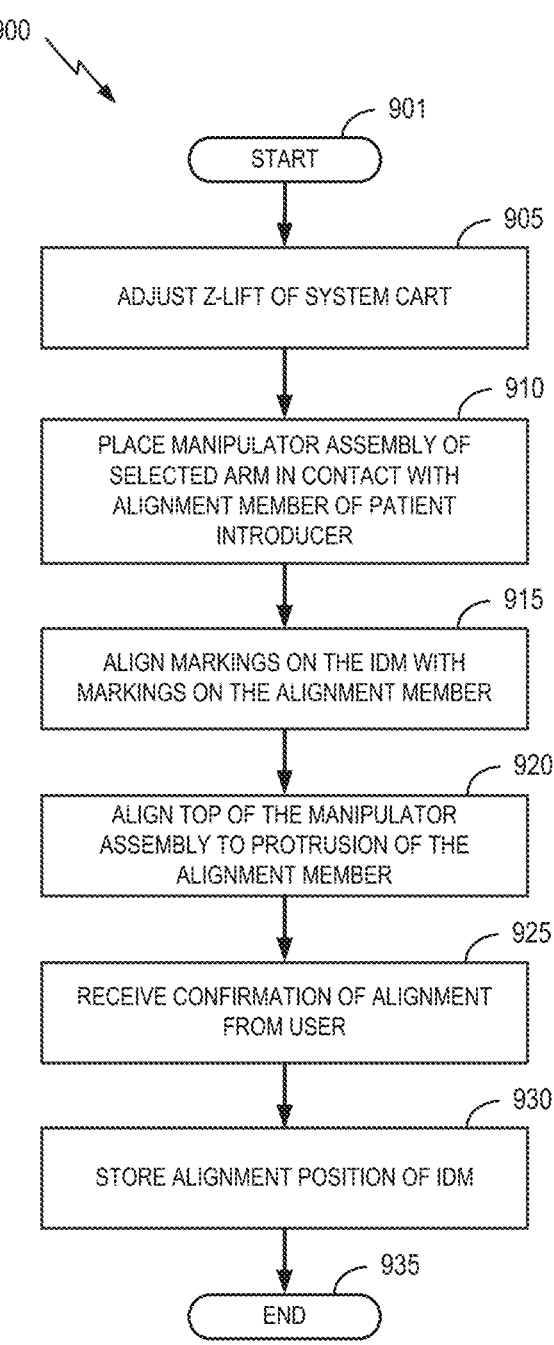

FIG. 11 provides a flowchart for a method 900 providing additional aspects related to block 620 of FIG. 8. The method 900 begins at block 901. At block 905, the user and/or the surgical robotic system 110 adjusts the Z-lift of the surgical robotic system cart. This may involve adjusting the height of the system cart to a level suitable for the height of the platform 102. At block 910, in a manual embodiment, the user places the manipulator assembly (e.g., IDM 190) of the selected robotic arm 175 in contact with the alignment member 309 of the patient introducer 301. The user may be required to press an admittance button to allow for the manual manipulation of the robotic arm 175.

Depending on the embodiment, block 910 may be performed automatically by the surgical robotic system 110 using one or more sensors as inputs for feedback during the alignment. In some embodiments, the alignment of the manipulator assembly with the patient introducer 301 may not involve physical contact therebetween. For example, in embodiments where the IDM 190 includes a laser and laser light sensor, the surgical robotic system 110 may use the detection of laser light emitted from the laser, reflected off of the alignment member 309, and detected at the laser light sensor in automatically determining whether the IDM 190 is aligned with the alignment member 309. In embodiments that include the use of LED(s), the robotic surgical system may determine that the IDM 190 is aligned with the alignment member 309 when photodiode placed on the IDM 190 detects light received from the LED. In embodiments that mount the patient introducer 301 to a robotic arm, the robotic system may determine that the IDM 190 of one of the robotic arms (e.g., second robotic arm 175-b holding endoscope 115) is aligned with another of the robotic arms (e.g., first robotic arm 175-a holding the patient introducer 301) when the multiple robotic arms are aligned along a virtual rail determined based on positional awareness capabilities of the multiple robotic arms. Additionally, any of the alignment features and/or sensors discussed above may also be used in the automatic alignment of the IDM 190 with the patient introducer 301 by the surgical robotic system 110.

At block 915, the user/surgical robotic system aligns the markings on the manipulator assembly with the markings on the alignment member. In the embodiments of FIGS. 7A-7H, this may involve rotating the manipulator assembly 190 with respect to the Z-axis until the markings are aligned. In some embodiments, alignment of the markings on the manipulator assembly with the markings on the alignment member 309 may involve moving the manipulator assembly with respect to the alignment member 309 until the alignment markings of the manipulator assembly are alignment with the alignment markings of the alignment member 309. At block 920, the user/surgical robotic system aligns the top of the manipulator assembly to the elongated protrusion 313 of the alignment member 309. In certain embodiments, block 920 may be performed prior to or currently with block 915.

At block 925, the surgical robotic system 110 receives confirmation from the user that the alignment process has been completed. In other embodiments, the surgical robotic system 110 may automatically confirm that the alignment has been completed, and thus, does not require user input from the user, or the surgical robotic system 110 may perform the alignment automatically, not requiring any user input to confirm or perform alignment. At block 930, the surgical robotic system 110 stores the alignment position and orientation of the IDM 190 (e.g., the six degrees of freedom defining the final position of the IDM 190 after the alignment procedure) in memory. The stored alignment position may be used by the surgical robotic system 110 to calibrate the control and/or movement of the IDM 190 during the following surgical procedure. The method 900 ends at block 925.

Figure 12:
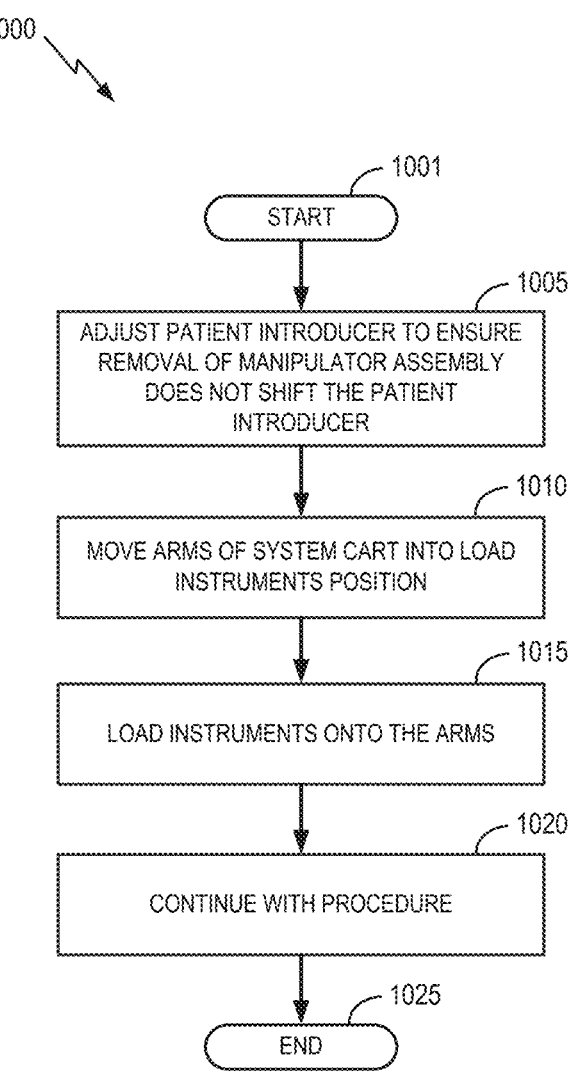

FIG. 12 provides a flowchart for a method 1000 providing additional aspects related to block 625. The method 1000 begins at block 1001. At block 1005, the user adjusts the patient introducer 301 to further secure the position of the patient introducer 301, preventing the patient introducer from shifting after the alignment procedure. For example, the patient introducer 301 may be secured by tightening a clamp (not illustrated) on the patient introducer holder 325.

At block 1010, the user moves the robotic arms 175 into a load instruments position. Block 1010 may also be performed automatically by the surgical robotic system 110. At block 1015, the user loads the instruments to be used during the surgical procedure onto the robotic arms 175. At block 1020, the user continues with the surgical procedure. The method 1000 ends at block 1025.

Figure 13:
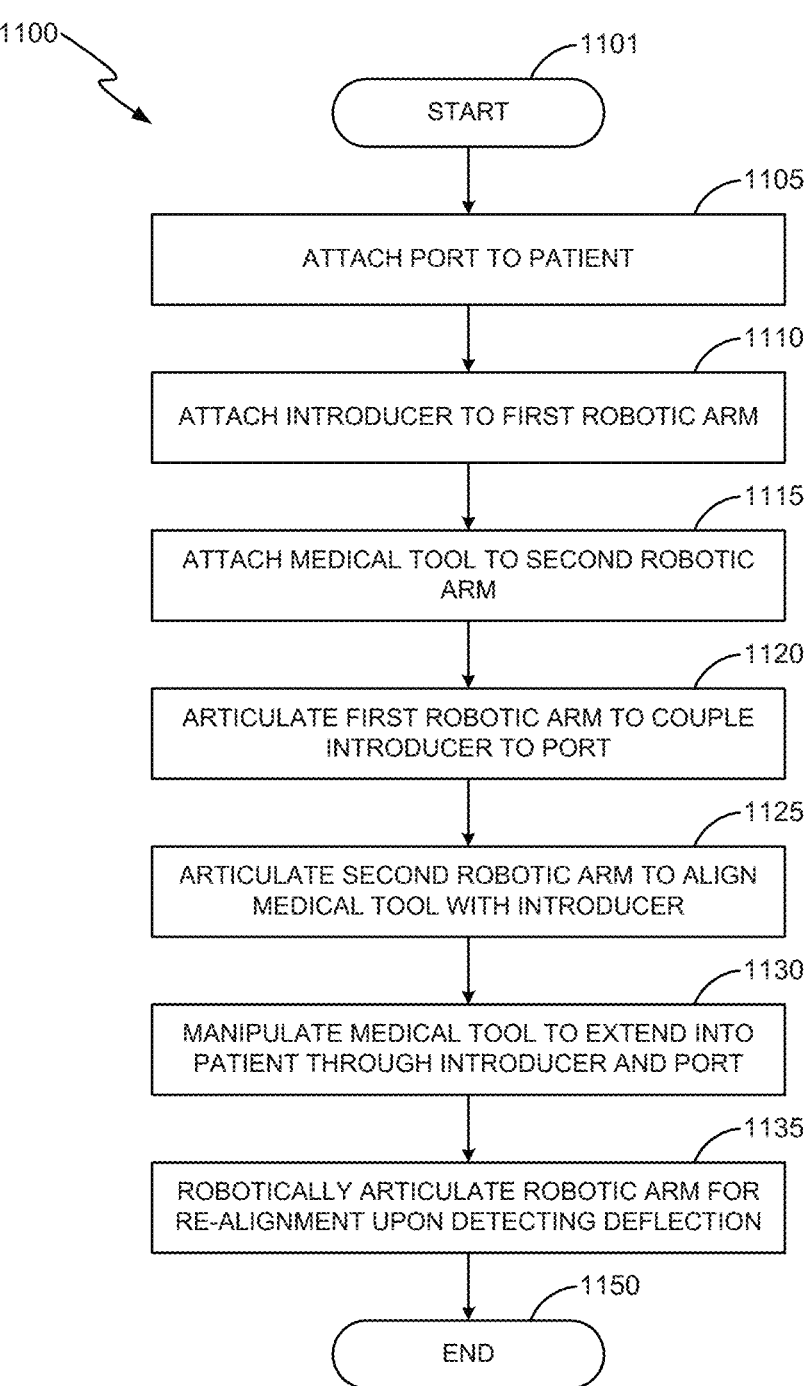
FIG. 13 provides a flowchart illustrating an example method of using a surgical robotic system in accordance with aspects of this disclosure.

FIG. 13 is a flowchart illustrating an example method 1100 of using a medical robotic system 110 in the context of a patient introducer 301 that can be mounted to a robotic arm of the system. The method 1100 encompasses various steps associated with using the robotic system 110, including setting up the system, aligning a medical tool 115 to the patient introducer 301, and performing a medical procedure on a patient using the system upon setup.

The method 1100 can begin at block 1101. At block 1105, port 320 is attached to a patient 101. In some embodiments, the port 320 can be installed in the patient 101 to provide endoluminal access to the patient. For example, the port 320 can be surgical tube, such as an endrotracheal tube, inserted into an entrance to a luminal pathway of the patient 101, such as a mouth providing entrance to airways 150 of a lung of the patient 101.

At block 1110, the patient introducer 301 is attached to a robotic arm 175. For example, the patient introducer 301 can be attached to a first robotic arm 175-a of the robotic system 110 by mounting the instrument base 465 of the patient introducer 301 onto a corresponding attachment interface of an IDM 190 of the first robotic arm 175-a.

At block 1115, one or more medical tools that are configured for insertion through the patient introducer 301 are attached to one or more robotic arms of the robotic system 110. For example, the endoscope 115 can be attached to a second robotic arm 175-b by mounting instrument base 465 of the endoscope 115 onto a corresponding attachment interface of an IDM 190 of the second robotic arm 175-b. In some embodiments, the endoscope 115 employs a leader-sheath arrangement, as further described above. Accordingly, at block 1115, a portion of the medical tool, such as an inner leader portion 145 of the endoscope 115, can be mounted to the second robotic arm 175-b, and another portion of the medical tool, such as outer sheath portion 147 of the endoscope 115, can be mounted to a third robotic arm 175-c.

At block 1120, the robotic arm holding the patient introducer 301 is manipulated to couple the patient introducer 301 to the port 320 on the patient. For example, the first robotic arm 175-a can be articulated, e.g., using an admittance mode or otherwise, to move the patient introducer 301 mounted thereto into close proximity of the port 320 and into a position where the patient introducer 301 can be attached to the port 320 using clip 498. The first robotic arm 175-a can be articulated manually by medical staff via activation of the admittance control mode (e.g., upon depression of admittance button 410), and locked into a desired position in three-dimensional space via deactivation of the admittance control mode (e.g., upon release of the admittance control button 410). Alternatively, or in combination, alignment and/or coupling of the patient introducer 301 to the port 320 can be achieved via movement of the robotic system cart itself.

At block 1125, one or more robotic arms holding other medical tool(s) are articulated to align the other medical tool(s) with the patient introducer 301. For example, the second robotic arm 175-b can be articulated, via automatic robotic controls or otherwise, to align the endoscope 115 with the entrance opening of the patient introducer 301 and facilitate insertion therethrough. In some embodiments, both the second and third robotic arms 175-b and 175-c are articulated to move both inner leader portion 145 and outer sheath portion 147 of the endoscope 115 into alignment with the entrance opening of patient introducer 301.

At block 1130, the robotic arms holding the other medical tool(s) manipulate the other medical tool(s) to extend the other medical tool(s) into the patient 101 through the patient introducer 301. For example, the second robotic arm 175-b can actuate an endoscope 115, via operation of one or more drive shafts 606 of an IDM 190 of the second robotic arm 175-b, to drive the endoscope 115 through the patient introducer 301 and into a luminal pathway of the patient 101. Alternatively, or in combination, the second robotic arm 175-b can drive the endoscope 115 through the patient introducer 301 and into the patient via articulation of the second robotic arm 175-b along a virtual rail 330 formed between the first and second robotic arms 175-a and 175-b. Joints 165 of the first robotic arm 175-a can be locked to hold the patient introducer 301 in a fixed position as the other robotic arms move the endoscope 115 therethrough into and out of the patient. In some bronchoscopy embodiments, the endoscope 115 can be inserted through the entrance of the lumen 595 (e.g., first opening 304 of introducer tube 307), out the exit of the lumen 595 (e.g., second opening 306 of introducer tube 307), through an endrotracheal tube on a mouth of patient 101, though the mouth and into a trachea of the patient, and into airways 150 in a lung of the patient.

At block 1135, the robotic system 110 can monitor a state of the system, during the procedure and after initial insertion of the endoscope 115 into the patient, to allow for dynamic re-alignment during the procedure. For example, the robotic system 110 may use positional awareness capabilities of the robotic arms 175 to monitor a position of the patient introducer 301 and the endoscope 115 relative to each other. Upon detection of a deflection, such as an accidental collision between the first and second robotic arms 175-a and 175-b or an accidental collision between at least one of the first or second robotic arms 175-a or 175-b and a medical staff or other object in the surrounding environment, the robotic system 110 may robotically articulate at least one of the first or second robotic arms 175-a or 175-b to re-align the endoscope 115 and patient introducer 301 and bring the endoscope 115 and the patient introducer 301 back into position. By mounting both the patient introducer 301 and the endoscope 115 inserted therethrough on respective robotic arms, the system may have improved ability to detect deflections or mis-alignments that may arise during the medical procedure. Such improved ability can enhance patient safety or ease use of the robotic system. The method 1100 ends at block 1150.

Implementing Systems and Terminology

Implementations disclosed herein provide systems, methods and apparatus for alignment of a surgical robotic system cart with a patient introducer.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical robotic system comprising:
first and second robotic arms;
an introducer coupled to the first robotic arm, the introducer comprising a first opening, a second opening, a channel connecting the first opening and the second opening, an instrument base having an attachment side configured to releasably attach to a distal end of the first robotic arm, a second side opposite the attachment side, a third side adjoining the attachment side and the second side, a third opening on the attachment side configured to permit a drive shaft of the first robotic arm to extend therethrough, and a bent or bendable introducer tube coupled to the instrument base;
a mount positioned on a side of the instrument base other than the attachment side, the mount including a slot configured to releasably attach to a complementary engagement member of the introducer tube such that the mount holds the introducer tube in a first position with respect to the instrument base; and
a flexible elongate medical tool coupled to the second robotic arm, the flexible elongate medical tool including an outer sheath portion and an inner leader portion, the second robotic arm being configured to drive the inner leader portion into a patient through the outer sheath portion and the introducer independently of the outer sheath portion.

2. The medical robotic system of claim 1, wherein the first robotic arm is configured to align the flexible elongate medical tool with the first opening of the introducer based on a virtual rail between the first and second robotic arms.

3. The medical robotic system of claim 2, wherein:
the virtual rail is configured to extend in a first direction, and
a portion of the channel is configured to extend along a path angled relative to the virtual rail to guide the flexible elongate medical tool out of the second opening of the introducer in a second direction different than the first direction.

4. The medical robotic system of claim 3, wherein:
the channel is a curved lumen,
the portion of the channel is a distal portion of the curved lumen that is connected to the second opening, and
the curved lumen has a proximal portion that is connected to the first opening and configured to align with the virtual rail extending in the first direction.

5. The medical robotic system of claim 1, further comprising a third robotic arm, wherein:
the inner leader portion is a first portion of an endoscope having an optical component for visualization of an internal anatomy of the patient,
the outer sheath portion is a second portion of the endoscope surrounding the inner leader portion,
the third robotic arm is configured to manipulate the outer sheath portion, and
the second robotic arm is configured to drive the inner leader portion.

6. The medical robotic system of claim 5, wherein:
the first, second, and third robotic arms are arranged in a row, and
the first robotic arm having the introducer coupled thereto is arranged at an end of the row.

7. The medical robotic system of claim 1, wherein:
the second robotic arm is configured to drive the flexible elongate medical tool into the patient via a port coupled to the patient,
the introducer further comprises a clip aligned with the second opening, and
the clip is configured to releasably attach to the port.

8. The medical robotic system of claim 1, further comprising a robot base, wherein:
the robot base is a cart having a plurality of wheels or a table having a platform configured to support the patient thereon,
the first robotic arm has a proximal end attached to the robot base and the distal end attached to the introducer, and
the second robotic arm has a proximal end attached to the robot base and a distal end attached to the flexible elongate medical tool.

9. The medical robotic system of claim 1, wherein:
the first opening of the introducer is configured to receive the flexible elongate medical tool, the second opening of the introducer is configured to deliver the flexible elongate medical tool into the patient, and the channel is configured to guide the flexible elongate medical tool along a curved path from the first opening to the second opening.

10. The medical robotic system of claim 1, wherein:

the channel of the introducer is a lumen of the introducer tube, the instrument base is releasably attached to a modular attachment interface of the first robotic arm, and the modular attachment interface of the first robotic arm is configured to releasably attach to a variety of instruments other than the introducer.

11. An introducer for a medical robotic system, the introducer comprising:

a first end forming a first opening configured to receive a flexible elongated medical tool including an outer sheath portion and an inner leader portion;

a second end forming a second opening configured to guide the flexible elongated medical tool into a port;

a bent or bendable introducer tube connecting the first end and the second end, the introducer tube being configured to guide the flexible elongated medical tool from the first end to the second end;

an instrument base having an attachment side configured to releasably attach to a modular attachment interface of a distal end of a first robotic arm coupled to the introducer tube, a second side opposite the attachment side, a third side adjoining the attachment side and the second side, and a third opening on the attachment side configured to permit a drive shaft of the first robotic arm to extend therethrough, the flexible elongated medical tool coupled to a second robotic arm configured to drive the inner leader portion into a patient through the outer sheath portion and the introducer tube independently of the outer sheath portion; and a mount positioned on a side of the instrument base other than the attachment side, the mount including a slot configured to releasably attach to a complementary engagement member of the introducer tube such that the mount holds the introducer tube in a first position with respect to the instrument base.

12. The introducer of claim 11, wherein:

the attachment side is configured to mate with the modular attachment interface of the first robotic arm, and the introducer tube is attached to a side of the instrument base opposite to the attachment side of the instrument base.

13. The introducer of claim 11, wherein the introducer tube is attached to the third side of the instrument base.

14. The introducer of claim 11, wherein the attachment side is configured to mate with the modular attachment interface of the first robotic arm.

15. The introducer of claim 11, wherein the mount is a movable mount, the introducer tube is attached to the instrument base via the movable mount, the movable mount permitting adjustment of at least one of a relative position or orientation between the introducer tube and the instrument base.

16. The introducer of claim 11, wherein the introducer tube is attached to the instrument base via one of a plurality of mounts on the instrument base, the plurality of mounts including the mount, each of the plurality of mounts being configured to hold the introducer tube on the instrument base in a different position or orientation with respect to the instrument base.

17. The introducer of claim 11, wherein the attachment side of the instrument base is configured to mate with the modular attachment interface of the first robotic arm and the attachment side comprises one or more other openings configured to respectively accommodate one or more other drive shafts of the first robotic arm.

18. The introducer of claim 11, wherein the introducer tube includes a curved lumen that is configured with a 90 degree bend.

19. The introducer of claim 11, wherein the introducer tube extends along a curved path containing two or more bends.

20. A method of using a medical robotic system, the method comprising:

mounting a bent or bendable introducer tube of an introducer to a base of the introducer via a mount, the base having an attachment side, a second side opposite the attachment side, a third side adjoining the attachment side and the second side, and an opening on the attachment side configured to permit a drive shaft of a first robotic arm to extend therethrough, the mount positioned on a side of the base other than the attachment side and including a slot configured to releasably attach to a complementary engagement member of the introducer tube such that the mount holds the introducer tube in a first position with respect to the base;

articulating the first robotic arm having the introducer coupled thereto, the introducer coupled to a distal end of the first robotic arm on the attachment side of the base of the introducer;

aligning the introducer with a port coupled to a patient via the articulating of the first robotic arm;

extending a medical tool, using a second robotic arm coupled to the medical tool, through the introducer and into the port while the introducer is aligned with the port, the medical tool including an outer sheath portion and an inner leader portion; and extending the inner leader portion into the patient through the port, the outer sheath portion, and the introducer independently of the outer sheath portion.

21. The method of claim 20, further comprising:

coupling the port to the patient prior to the aligning of the introducer;

coupling the introducer to the distal end of the first robotic arm via a modular attachment interface prior to the articulating of the first robotic arm; and coupling the introducer to the port while the introducer is aligned with the port.

22. The method of claim 20, wherein the articulating of the first robotic arm is actuated manually using an admittance mode of the first robotic arm.

23. The method of claim 20, further comprising:

determining, via a processor, a position of the introducer based on an articulation state of the first robotic arm while the introducer is aligned with the port; and robotically actuating the second robotic arm to align the medical tool to the introducer based on the determined position of the introducer.

24. The method of claim 20, further comprising:

detecting a deflection of at least one of the first robotic arm or the second robotic arm that brings the medical tool out of alignment with the introducer; and robotically actuating at least one of the first robotic arm or the second robotic arm to align the medical tool to the introducer upon the detection of the deflection.

25. The method of claim 20, wherein:

the port is an endotracheal tube inserted through a mouth and into a trachea of the patient, the medical tool is a flexible bronchoscope, and the extending of the medical tool through the port and into the patient includes extending the flexible bronchoscope through the endotracheal tube and into a lung of the patient via the second robotic arm.

26. The method of claim 20, wherein the articulating of the first robotic arm is actuated robotically.

27. An adapter for a medical robotic system, the adapter comprising:

a base having a first side configured to releasably attach to a distal end of a first robotic arm, a second side opposite the first side, and a third side adjoining the first side and the second side;

an opening on the first side of the base, the opening being configured to permit a drive shaft of the first robotic arm to extend therethrough; and a mount positioned on a side of the base other than the first side, the mount including a slot configured to releasably attach to a complementary engagement member of a bent or bendable introducer tube coupled to the first robotic arm such that the mount holds the introducer tube in a first position with respect to the base while an inner leader portion of a medical tool is being driven through an outer sheath portion of the medical tool and through the introducer tube independently of the outer sheath portion.

28. The adapter of claim 27, wherein the base is configured to isolate the introducer tube from any operative coupling to the drive shaft when the first side is attached to the distal end of the first robotic arm.

29. The adapter of claim 27, wherein the mount is positioned on the second side of the base opposite the first side.

30. The adapter of claim 27, wherein the mount is positioned on the third side of the base adjoining the first and second sides.

31. The adapter of claim 27, wherein:

the mount is a first mount positioned on the second side of the base, the adapter further comprises a second mount positioned on the third side of the base, and the second mount is configured to releasably attach to the introducer tube to hold the introducer tube in a different position than the first position with respect to the base.

32. The adapter of claim 27, wherein:

the mount is a first mount, the first mount holds the introducer tube in a first orientation with respect to the base while the medical tool is being driven through the introducer tube, the adapter further comprises a second mount positioned on the base at a different orientation with respect to the first mount, and the second mount is configured to releasably attach to the introducer tube to hold the introducer tube in a different orientation than the first orientation with respect to the base.

33. The adapter of claim 27, wherein the mount is moveably coupled to the base to permit a change in position of at least one of the introducer tube or the medical tool with respect to the base.

34. The adapter of claim 27, wherein the opening is a first opening, the drive shaft is a first drive shaft, and the adapter further comprises a plurality of other openings on the first side of the base, the plurality of other openings being configured to permit a plurality of other drive shafts of the first robotic arm to respectively extend therethrough.

35. The adapter of claim 27, wherein the inner leader portion is driven by a second robotic arm, and wherein the outer sheath portion is driven by a third robotic arm.

36. The adapter of claim 35, wherein the medical tool is aligned with a receive axis of the introducer tube based on at least one virtual rail associated with the first, second, and third robotic arms.

37. The adapter of claim 27, wherein the inner leader portion has a smaller diameter than the outer sheath portion.

* * * * *